US009877478B2

(12) United States Patent
Becher et al.

(10) Patent No.: US 9,877,478 B2
(45) Date of Patent: Jan. 30, 2018

(54) ENCAPSULATION OF HERBICIDES TO REDUCE CROP INJURY

(75) Inventors: David Z. Becher, St. Louis, MO (US); William Abraham, Wildwood, MO (US); S. Douglas Prosch, Ballwin, MO (US); Brett H. Bussler, Webster Groves, MO (US); Amanda C. Herr, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 348 days.

(21) Appl. No.: 12/705,789

(22) Filed: Feb. 15, 2010

(65) Prior Publication Data

US 2010/0248963 A1   Sep. 30, 2010

Related U.S. Application Data

(60) Provisional application No. 61/152,533, filed on Feb. 13, 2009.

(51) Int. Cl.
*A01N 37/26* (2006.01)

(52) U.S. Cl.
CPC .................. *A01N 37/26* (2013.01)

(58) Field of Classification Search
CPC ..... A01N 37/26; A01N 2300/00; A01N 25/28
USPC ........ 504/127, 144, 149, 267, 289, 338, 341
See application file for complete search history.

(56) References Cited

U.S. PATENT DOCUMENTS

| | | |
|---|---|---|
| 3,516,846 A | 6/1970 | Matson |
| 3,516,941 A | 6/1970 | Matson |
| 3,959,464 A | 5/1976 | DeSavigny |
| 4,021,224 A * | 5/1977 | Pallos et al. ................. 504/112 |
| 4,107,292 A | 8/1978 | Nemeth |
| 4,193,889 A | 3/1980 | Baatz et al. |
| 4,280,833 A | 7/1981 | Beestman et al. |
| 4,285,720 A | 8/1981 | Scher |
| 4,356,108 A | 10/1982 | Schwab et al. |
| 4,417,916 A | 11/1983 | Beestman et al. |
| 4,428,983 A | 1/1984 | Nehen et al. |
| 4,480,082 A | 10/1984 | McLean et al. |
| 4,489,017 A | 12/1984 | Alberts et al. |
| 4,563,212 A | 1/1986 | Becher et al. |
| 4,599,271 A | 7/1986 | Chao |
| 4,640,709 A | 2/1987 | Beestman |
| 4,643,764 A | 2/1987 | Scher |
| 4,668,580 A | 5/1987 | Dahm et al. |
| 4,670,246 A | 6/1987 | Dahl et al. |
| 4,681,806 A | 7/1987 | Matkan et al. |
| 4,738,898 A | 4/1988 | Vivant |
| 4,847,152 A | 7/1989 | Jabs et al. |
| 4,859,788 A | 8/1989 | Brindopke et al. |
| 4,889,719 A | 12/1989 | Ohtsubo et al. |
| 4,936,901 A | 6/1990 | Surgant, Sr. et al. |
| 4,938,797 A | 7/1990 | Hasslin et al. |
| 4,956,129 A | 9/1990 | Scher et al. |
| 5,006,161 A | 4/1991 | Hasslin et al. |
| 5,049,182 A | 9/1991 | Scher et al. |
| 5,223,477 A | 6/1993 | Scher et al. |
| 5,310,721 A | 5/1994 | Lo |
| 5,342,556 A | 8/1994 | Traubel et al. |
| 5,354,742 A * | 10/1994 | Deming et al. ............... 514/117 |
| 5,461,027 A | 10/1995 | Bergman |
| 5,583,090 A | 12/1996 | Stern et al. |
| 5,686,384 A | 11/1997 | Hester |
| 5,783,520 A | 7/1998 | Anderson et al. |
| 5,925,464 A | 7/1999 | Mulqueen et al. |
| 5,925,595 A | 7/1999 | Seitz et al. |
| 6,020,066 A | 2/2000 | Weisser et al. |
| 6,133,197 A | 10/2000 | Chen et al. |
| 6,337,130 B1 | 1/2002 | Van Koppenhagen et al. |
| 6,340,653 B1 | 1/2002 | Scher et al. |
| 6,485,736 B1 | 11/2002 | Shirley et al. |
| 6,566,306 B1 | 5/2003 | Wolf et al. |
| 6,653,256 B1 | 11/2003 | Wolf et al. |
| 6,730,635 B2 | 5/2004 | Wolf et al. |
| 6,992,047 B2 | 1/2006 | Asrar et al. |
| 7,056,522 B2 | 6/2006 | Voris et al. |
| 7,199,185 B2 | 4/2007 | Heming et al. |
| 7,381,861 B2 | 6/2008 | Cerny et al. |
| 7,687,434 B2 | 3/2010 | De Billot et al. |
| 7,718,572 B2 | 5/2010 | Igari et al. |
| 7,754,655 B2 | 7/2010 | Wolf et al. |

(Continued)

FOREIGN PATENT DOCUMENTS

| | | |
|---|---|---|
| EP | 0008207 A2 | 2/1980 |
| EP | 0148149 A2 | 7/1985 |

(Continued)

OTHER PUBLICATIONS

Scher, H.B., et al., "Microencapsulation of Pesticides by Interfacial Polymerization Utilizing Isocyanate or Aminoplast Chemistry," 1998, Pesti Sci, 54/4:394-400, XP-000804298.
International Search Report issued in International Application PCT/US2010/024158, dated Sep. 28, 2011, 6 pages.
Parker, D.C. et al., "Fall and Early Preplant Application Timing Effects on Persistence and Efficacy of Acetamide Herbicides," 2005, Weed Technology, 19:6-13.
Wilson, R., "Chapter 20: Encapsulated Acetochlor for Selective Weed Control in Roundup-Ready Sugarbeets," 2010, 2009 Weed Control Report, http://panhandle.unl.edu/c/document_library/get_file?uuid+a97205bc-1618-4ffc-ac2d-45bf5ee801b5&groupId=131817, 3 pages.
2010 Research Progress Report, Mar. 8-11, 2010, Western Society of Weed Science, Waikoloa, Hawaii, http://www.wsweedscience.org/Research Report Archive/2010 WSWS RPR.pdf, 146 pages.

(Continued)

*Primary Examiner* — Johann R Richter
*Assistant Examiner* — Courtney Brown
(74) *Attorney, Agent, or Firm* — Senniger Powers LLP; Erin C. Robert

(57) ABSTRACT

Methods of reducing injury to crop foliage and achieving weed control using encapsulated acetamide herbicides are described. Herbicidal microcapsules comprising herbicide core material and a shell wall encapsulating the core material are also described. The microcapsules provide reduced crop injury through controlled herbicide release.

45 Claims, 44 Drawing Sheets

(56) References Cited

U.S. PATENT DOCUMENTS

| | | | |
|---|---|---|---|
| 2003/0022791 A1* | 1/2003 | Asrar et al. | 504/116.1 |
| 2004/0137031 A1* | 7/2004 | Seitz et al. | 424/408 |
| 2005/0208089 A1 | 9/2005 | Asrar et al. | |
| 2005/0233907 A1 | 10/2005 | Nabors et al. | |
| 2005/0277549 A1 | 12/2005 | Seitz et al. | |
| 2008/0242548 A1 | 10/2008 | Asrar et al. | |
| 2009/0105077 A1 | 4/2009 | Bhatti et al. | |

FOREIGN PATENT DOCUMENTS

| | | | |
|---|---|---|---|
| EP | 0148149 A2 * | 10/1985 | |
| EP | 0252896 A2 | 1/1988 | |
| EP | 0369614 A1 | 5/1990 | |
| EP | 0679333 A2 | 11/1995 | |
| EP | 0780154 A1 | 6/1997 | |
| JP | 09-249505 | 9/1997 | |
| WO | 81/02505 A1 | 9/1981 | |
| WO | 92/13450 A1 | 8/1992 | |
| WO | 00/05951 A1 | 2/2000 | |
| WO | 00/05952 A1 | 2/2000 | |
| WO | 01/10414 A1 | 2/2001 | |
| WO | 01/94001 A2 | 12/2001 | |
| WO | 01/96010 A1 | 12/2001 | |
| WO | 02/082901 A1 | 10/2002 | |
| WO | 2005012488 A2 | 2/2005 | |
| WO | 2005/122759 A1 | 12/2005 | |
| WO | 2009103455 A2 | 8/2009 | |

OTHER PUBLICATIONS

Microencapsulation Technology and Future Trends, Stern et al., 1996, Chapter 7, pp. 93-114.

Zhang, B., et al., "Pesticide Processing Technology," 1996, Central Plains Farmer Press, pp. 64-65 and 74-76, 11 pages.

Han, X., "Pesticide Introduction," 1995, China Agricultural University Press, pp. 37-38, 6 pages.

Specimen Label Degree® Herbicide, Monsanto Company, EPA Reg. No. 524-496, 2012, 8 pages.

Specimen Label Harness® Herbicide by Monsanto, EPA Reg. No. 524-473, 2012, 9 pages.

Translation to English of EP 0780154 A1, Published Jun. 25, 1997, 6 Pages.

* cited by examiner

RR FLEX COTTON INJURY WITH POST-EMERGENT APPLICATIONS OF ACETOCHLOR FORMULATIONS (7 DAT)

RR SOYBEAN INJURY FROM POST-EMERGENT APPLICATIONS OF ACETOCHLOR FORMULATIONS (8 DAT)

LAMBSQUARTER CONTROL WITH PRE-EMERGENT APPLICATIONS OF ACETOCHLOR FORMULATIONS (20 DAT)

YELLOW FOXTAIL CONTROL WITH PRE-EMERGENT APPLICATIONS OF ACETOCHLOR FORMULATIONS (20 DAT)

PERENNIAL RYEGRASS CONTROL WITH PRE-EMERGENT APPLICATIONS OF ACETOCHLOR FORMULATIONS (34 DAT)

COTTON INJURY WITH POST-EMERGENT APPLICATIONS OF ACETOCHLOR FORMULATIONS (14 DAT)

YELLOW FOXTAIL CONTROL WITH PRE-EMERGENT APPLICATIONS OF ACETOCHLOR FORMULATIONS (19 DAT)

BARNYARDGRASS CONTROL WITH PRE-EMERGENT APPLICATIONS OF ACETOCHLOR FORMULATIONS (19 DAT)

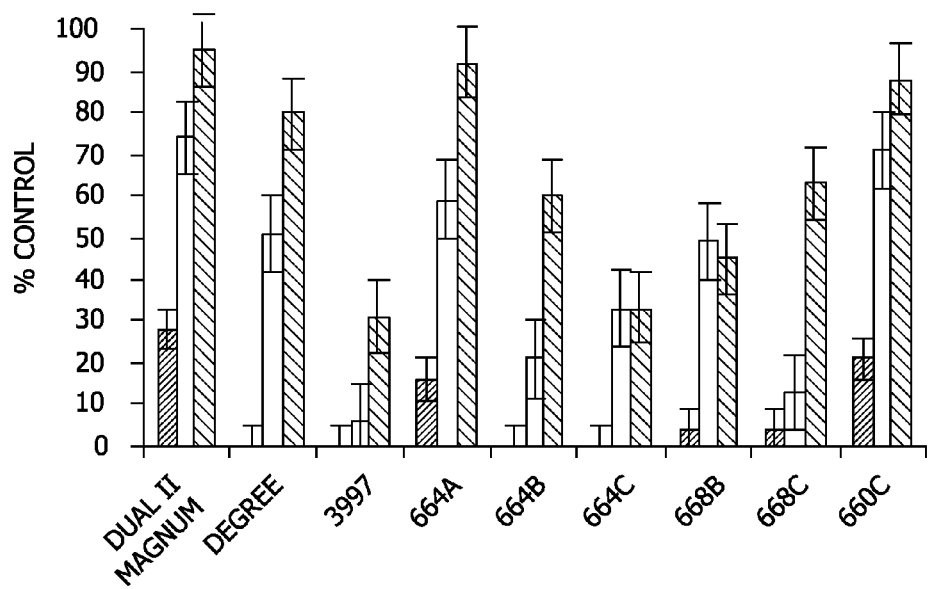
FIG. 75 CRABGRASS CONTROL WITH PRE-EMERGENT APPLICATIONS OF ACETOCHLOR FORMULATIONS (23 DAT)
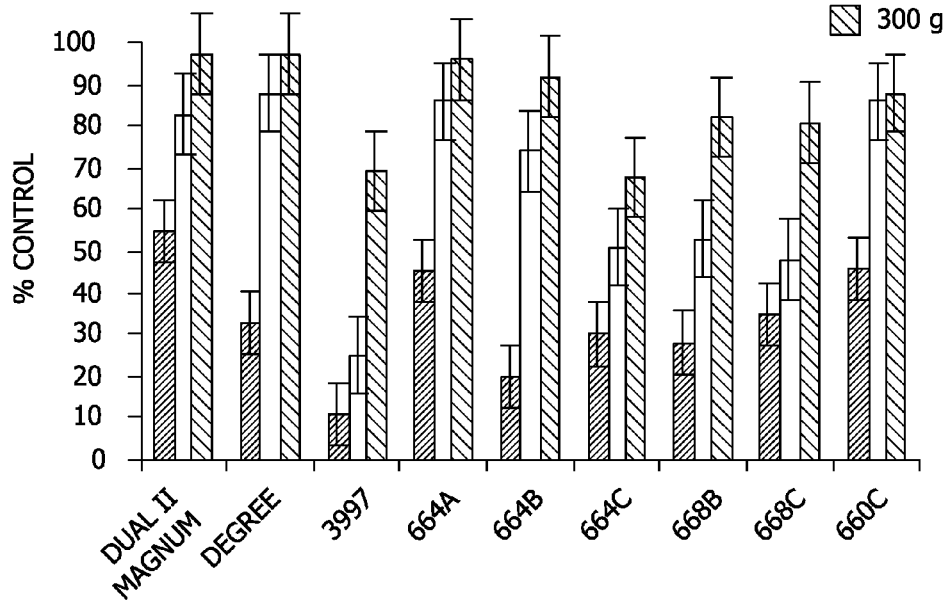
FIG. 76 BARNYARDGRASS CONTROL WITH PRE-EMERGENT APPLICATIONS OF ACETOCHLOR FORMULATIONS (23 DAT)

ENCAPSULATION OF HERBICIDES TO REDUCE CROP INJURY

This application claims benefit of U.S. provisional application Ser. No. 61/152,533 filed Feb. 13, 2009, the entire disclosure of which is incorporated herein by reference.

FIELD OF THE INVENTION

The present invention generally relates to methods of reducing injury to crop foliage and achieving commercial weed control using encapsulated acetamide (e.g., acetanilide) herbicides.

BACKGROUND OF THE INVENTION

The emergence of glyphosate-resistant weeds has generated interest in the use of residual herbicides as tank-mix partners with glyphosate in glyphosate-tolerant (e.g., ROUNDUP READY or RR) crops. Acetamide herbicides, including, for example, acetanilide herbicides, typically do not offer significant post-emergence activity, but as a residual partner would provide control of newly emerging monocots and small-seeded dicot weed species. This would usefully supplement the activity of glyphosate which is effective on emerged weeds, but lacks significant residual activity.

Acetanilide herbicides have traditionally been applied to the soil before planting as pre-emergent herbicides. The application of acetanilide herbicides prior to emergence of the crop, however, has caused many crops to be damaged or killed. In response to this problem, it was proposed to apply commercially available acetanilide herbicide formulations after the emergence of the crop (i.e., post-emergent to the crop), but before the emergence of later germinating weeds (i.e., pre-emergent to the weeds). Application during this time window, however, caused unexpected foliar injury to the crop. The injury was observed with both commercially available conventional acetanilide emulsifiable concentrate (EC) formulations and with commercially available encapsulated acetanilide formulations.

Prior art microencapsulation procedures are generally adequate for producing formulations with good weed control. However, the practitioner of this art has had some difficulty optimizing the release rates to obtain acceptable bioefficacy for a given active while minimizing crop injury to commercially acceptable levels. In particular, commercial encapsulated formulations may show greater systemic crop plant injury over time in the form of leaf crinkling and plant stunting when compared to emulsifiable concentrates.

In microencapsulation technology known in the art, core herbicide is typically released from a microcapsule at least in part by molecular diffusion through the shell wall. Modification of shell wall thickness to increase or decrease herbicide rate has definite limitations.

Thin shell walls are sensitive to premature mechanical rupture during handling or in the field, resulting in immediate release. Poor package stability resulting from shell wall defects can also arise when the core material is in direct contact with the external vehicle. As a result, some core material may crystallize outside the capsule causing problems in spray applications, such as spray nozzle plugging. Further, higher shear encountered in certain application means, such as spray applications, can result in shell wall rupture and herbicide release. The microcapsule thus becomes little more than an emulsion stabilized against coalescence. When delivered to the field, herbicide release is so fast that little crop safety improvement is gained over conventional emulsion concentrate formulations.

If the wall thickness is increased, the bioefficacy quickly drops to a marginal performance level because herbicide release is delayed. There is also a practical limit to the wall thickness in interfacial polymerization. As the polymer precipitates, the reaction becomes diffusion controlled. The reaction rate can drop to such an extent that non-constructive side reactions can predominate.

Various formulation solutions have been attempted to address the release rate limitations. For example, two package or single package blends of microcapsules and dispersions or emulsions of free agricultural actives have been proposed in Scher, U.S. Pat. Nos. 5,223,477 and 5,049,182. Seitz et al., U.S. Pat. No. 5,925,595 and U.S. Publication No. 2004/0137031 A1, teach methods for producing microencapsulated acetochlor. The degree of permeability is regulated by a compositional change in the precursors for the wall. Although the Sietz compositions have proven effective for weed control, unacceptable crop injury has been observed in connection with the use of those compositions when applied to certain commercially important crops.

A need therefore exists for herbicide compositions and methods utilizing acetamide herbicides such as acetamide herbicides whereby simultaneous commercially acceptable weed control and commercially acceptable crop injury can be attained.

SUMMARY OF THE INVENTION

Among the various aspects of the present invention may be noted the provision of encapsulated acetamide herbicide compositions and methods for use thereof. The present invention provides for post-emergence crop and pre-emergence weed application of the encapsulated acetamide herbicides wherein herbicide release rate is controlled in order to give both commercially acceptable weed control and commercially acceptable crop injury.

Briefly, therefore, one embodiment of the present invention is directed to a particulate microencapsulated acetamide herbicide comprising a water-immiscible core material comprising the acetamide herbicide and a microcapsule having a shell wall comprising a polyurea, the microcapsule containing the core material. The shell wall is formed in a polymerization medium by a polymerization reaction between a polyisocyanate component comprising a polyisocyanate or mixture of polyisocyanates and a polyamine component comprising a polyamine or mixture of polyamines to form the polyurea. The ratio of amine molar equivalents contained in the polyamine component to isocyanate molar equivalents contained in the polyisocyanate component is at least 1.1:1 and a population of the microcapsules has a mean particle size of at least about 7 μm.

Another embodiment of the present invention is directed to a particulate microencapsulated acetamide herbicide comprising a water-immiscible core material comprising the acetamide herbicide and a microcapsule having a shell wall comprising a polyurea, the microcapsule containing the core material. The shell wall is formed in a polymerization medium by a polymerization reaction between a polyisocyanate component comprising a polyisocyanate or mixture of polyisocyanates and a polyamine component consisting essentially of a principal polyamine to form the polyurea. A population of the microcapsules has a mean particle size of at least about 7 μm.

Another embodiment of the present invention is directed to a particulate microencapsulated acetamide herbicide comprising a water-immiscible core material comprising the acetamide herbicide and a microcapsule having a shell wall comprising a polyurea, the microcapsule containing the core material. The shell wall is formed in a polymerization medium by a polymerization reaction between a polyisocyanate component comprising a polyisocyanate or mixture of polyisocyanates and a polyamine component comprising a polyamine or mixture of polyamines to form the polyurea. A population of the microcapsules has a mean particle size of at least about 7 µm and the shell wall is of limited permeability. The nature and composition of said shell wall and encapsulated acetamide is such that, when an aqueous slurry consisting of 1% by weight of the encapsulated acetamide herbicide in an aqueous medium consisting of deionized water is subjected to agitation at a rate sufficient to maintain the particles in suspension without mechanical rupturing, the acetamide content of the aqueous medium remains less than 100 ppm after agitation for 6 hours at 25° C., and less than 150 ppm acetamide after agitation for 24 hours at 25° C.

Yet another embodiment of the present invention is directed to a method of controlling weeds in a field of crop plants, the method comprising forming an application mixture comprising the particulate microencapsulated acetamide herbicides of the present invention and applying the application mixture in a herbicidally effective amount post-emergent to the crop plants.

Another embodiment of the present invention is directed to a method of controlling commercially important weeds located in a field of crop plants. The method comprises forming an application mixture comprising a particulate encapsulated acetamide herbicide composition and applying the application mixture in an herbicidally effective amount post-emergent to the crop plants and pre-emergent to the weeds. The particulate acetamide herbicide comprises shell/core particles each having a core comprising acetamide contained within a shell of limited permeability, and the nature and composition of said particulate encapsulated acetamide is such that, when an aqueous slurry consisting of 1% by weight of the encapsulated acetamide herbicide in an aqueous medium consisting of deionized water is subjected to agitation at a rate sufficient to maintain the particles in suspension without mechanical rupturing, the acetamide content of the aqueous medium remains less than 100 ppm after agitation for 6 hours at 25° C., and less than 150 ppm acetamide after agitation for 24 hours at 25° C.

Another embodiment of the present invention is directed to a method of controlling commercially important weeds located in a field of crop plants. The method comprises forming an application mixture comprising a particulate encapsulated acetamide herbicide composition and applying the application mixture in a herbicidally effective amount post-emergent to the crop plants and pre-emergent to the weeds. The rate of crop injury is no more than 20% for the time period of from 1 day to 28 days after applying the application mixture to crop plants in the growth stage range of from crop emergence to the six-leaf growth stage and the rate of weed control is at least 60% for the time period of from application of the application mixture to 12 weeks after application of the application mixture.

Other objects and features will be in part apparent and in part pointed out hereinafter.

BRIEF DESCRIPTION OF THE DRAWINGS

FIG. 75 is a graph depicting control of crabgrass achieved with pre-emergent applications of various microencapsulated acetochlor formulations as described in Example 48.

FIG. 76 is a graph depicting control of barnyard grass achieved with pre-emergent applications of various microencapsulated acetochlor formulations as described in Example 48.

DESCRIPTION OF THE EMBODIMENTS OF THE INVENTION

Figure 1:
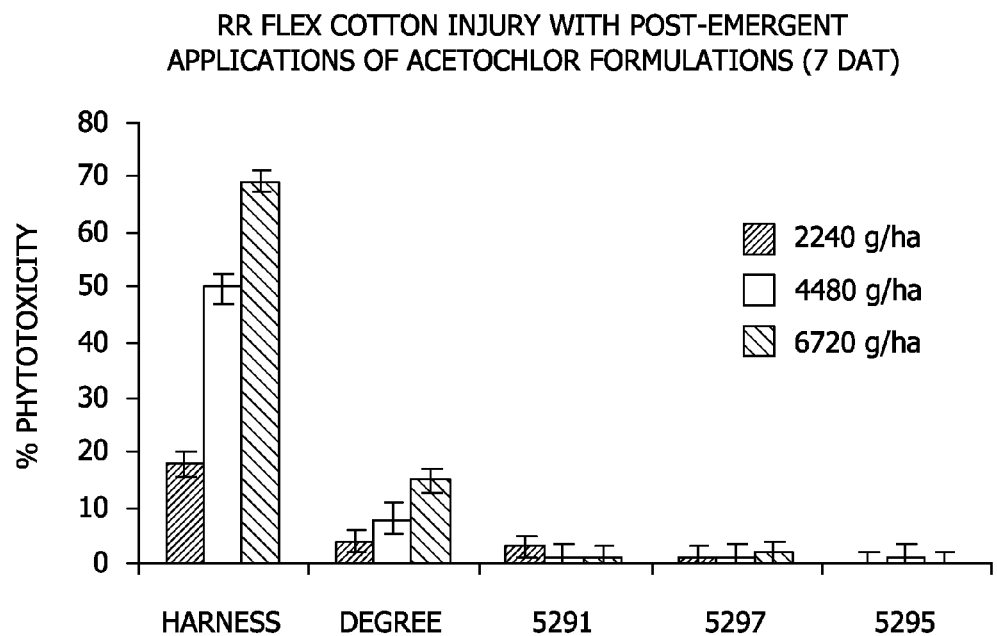
FIG. 1 is a graph depicting cotton injury that occurred with post-emergent applications of various microencapsulated acetochlor formulations as described in Example 2.

In accordance with the present invention, compositions comprising encapsulated herbicides (e.g., particulate microencapsulated herbicides) having a low initial release rate and a sustained long term release, and methods for using such compositions, are provided that provide both commercially acceptable weed control and commercially acceptable crop injury. The compositions are useful for the control of weeds, pre-emergence, when applied to fields post-emergence to the crop plants.

In accordance with the present invention, "weed control" refers to any observable measure of control of plant growth, which can include one or more of the actions of (1) killing, (2) inhibiting growth, reproduction or proliferation, and (3) removing, destroying, or otherwise diminishing the occurrence and activity of plants. Weed control can be measured by any of the various methods known in the art. For example, weed control can be determined as a percentage as compared to untreated plants following a standard procedure wherein a visual assessment of plant mortality and growth reduction is made by one skilled in the art specially trained to make such assessments. In another control measurement method, control is defined as a mean plant weight reduction percentage between treated and untreated plants. In yet another control measurement method, control can be defined as the percentage of plants that fail to emerge following a pre-emergence herbicide application. A "commercially acceptable rate of weed control" varies with the weed species, degree of infestation, environmental conditions, and the associated crop plant. Typically, commercially effective weed control is defined as the destruction (or inhibition) of at least about 60%, 65%, 70%, 75%, 80%, or even at least 85%, or even at least 90%. Although it is generally preferable from a commercial viewpoint that 80-85% or more of the weeds be destroyed, commercially acceptable weed control can occur at much lower destruction or inhibition levels, particularly with some very noxious, herbicide-resistant plants. Advantageously, the herbicidal microcapsules achieve commercially acceptable weed control in the time period of from application of the herbicide microcapsules, for example as contained in an application mixture, to 3 weeks, 4 weeks, 5 weeks, 6 weeks, 7 weeks, 8 weeks, 9 weeks, 10 weeks, 11 weeks, or even 12 weeks after application of the herbicide microcapsules.

Crop damage can be measured by any means known in the art, such as those described above for weed control determination. A "commercially acceptable rate of crop injury" for the present invention likewise varies with the crop plant species. Typically, a commercially acceptable rate of crop injury is defined less than about 20%, 15%, 10% or even less than about 5%. The herbicidal microcapsules of the present invention limit crop injury to a commercially acceptable rate as measured from about 24 hours (about 1 DAT) after application to two weeks (about 14 DAT), from about 24 hours (about 1 DAT) after application to three weeks (about 21 DAT), or from about 24 hours (about 1 DAT) to about four weeks (about 28 DAT).

In some embodiments of the present invention, the compositions of the present invention can be applied post-emergence to crop plants and pre-emergence to weeds in order to simultaneously achieve commercial weed control and a commercially acceptable rate of crop injury. For purposes of the present invention, post-emergence to crop plants includes initial emergence from the soil, i.e., "at cracking". Examples of crop plants include corn, peanuts, potatoes, soybeans, canola, sugarbeets, grain sorghum (milo), field beans and cotton. Crop plants include hybrids, inbreds, and transgenic or genetically modified plants having specific traits or combinations of traits including, without limitation, herbicide tolerance (e.g., resistance to glyphosate, glufosinate, sethoxydim, etc.), *Bacillus thuringiensis* (Bt), high oil, high lysine, high starch, nutritional density, and drought resistance. In some embodiments, the crop plants are resistant to organophosphorus herbicides, ALS inhibitor herbicides, synthetic auxin herbicides and/or acetyl CoA carboxylase inhibitor herbicides, In other embodiments the crop plants are resistant to glyphosate, dicamba, 2,4-D, MCPA, quizalofop, glufosinate and/or diclofop-methyl. In other embodiments, the crop plant is glyphosate and/or dicamba resistant. In some embodiments of the present invention, crop plants are glyphosate and/or glufosinate resistant. Preferred crops include corn, cotton, and soybeans. Particularly preferred crop species are cotton and soybean.

Acetamide herbicides suitable for the practice of the present invention include dimethenamid, napropamide, pronamide and acetanilide herbicides such as acetochlor, alachlor, butachlor, butenachlor, delachlor, diethatyl, dimethachlor, mefenacet, metazochlor, metolachlor, pretilachlor, propachlor, propisochlor, prynachlor, terbuchlor, thenylchlor and xylachlor, mixtures thereof and stereoisomers thereof. Some acetamide herbicides are available in their free forms, as salts, or as derivatized materials, for example, as esters. Any form of the herbicides described herein by name is potentially applicable. For instance, the present invention has utility for both racemic metolachlor and S-metolachlor, and racemic dimethenamid and dimethenamid-P. Preferred acetamide herbicides include dimethenamid and dimethenamid-P and preferred acetanilide herbicides include acetochlor, metolachlor and S-metolachlor.

An additional aspect of the present invention is the use of the encapsulated acetamide formulations as tank mix partners with foliar active herbicides. Examples of foliar active herbicides include, but are not limited to, glyphosate, dicamba, 2,4-D, and/or glufosinate or glufosinate-P. It is well known in the art that the mixing of foliar active herbicides with co-herbicides (such as acetamides) and/or other materials which cause foliar injury can, in some cases, result in antagonism wherein the uptake of the foliar herbicides is reduced thereby resulting in lower herbicidal effectiveness. It is believed that the release rate of the encapsulated acetamides of the present invention is reduced as compared to prior art compositions thereby minimizing antagonism such that the co-herbicide (e.g. glyphosate) is effectively absorbed and translocated within the plant before leaf damage induced by the acetamide herbicide can significantly interfere with absorption and translocation of the co-herbicide. Therefore, in addition to reducing foliar injury on crop plants, the encapsulated acetamide herbicides of this invention should minimize the initial localized foliar injury to previously emerged weeds and thereby allow the foliar active components of the co-herbicide to effectively and efficiently absorb into and translocate through the previously emerged weeds in order to achieve maximum activity in the absence of antagonism between the acetamide and co-herbicide.

In general, the encapsulated herbicides of the present invention are prepared by contacting an aqueous continuous phase containing a polyamine component comprising a polyamine source and a discontinuous oil phase containing the herbicide and a polyisocyanate component comprising a polyisocyanate source. A shell wall is formed in a polymerization reaction between the polyamine source and the isocyanate source at the oil/water interface thereby forming a capsule or microcapsule containing the herbicide. The polyamine source can be a mixture of a principal polyamine and one or more auxiliary polyamines, also termed a polyamine mixture. In some embodiments of the present invention, the polyamine source consists essentially of a principal polyamine. As used herein, a principal polyamine (also referred to as a principal amine) refers to a polyamine consisting essentially of a single polyamine species. The polyisocyanate source can be a polyisocyanate or mixture of polyisocyanates.

In accordance with the present invention and based on experimental evidence, it has been discovered that the objects of the invention can be achieved by encapsulating herbicides, in particular, acetamides, in microcapsules prepared by the selection of one or more certain compositional and process variables including the molar ratio of polyamine to polyisocyanate, the shell wall composition, the weight ratio of core material (herbicide component) to shell wall material, the core material components, the mean microcapsule particle size, process conditions such as mixing shear and time, and combinations thereof. Through the careful selection of these and other factors, aqueous dispersions of microencapsulated herbicides have been developed according to the compositions and methods described herein which, as compared to compositions and methods known in the art, reduce crop foliage injury for post-emergent application to the crop plants to a commercially acceptable level while simultaneously achieving commercially acceptable weed control for pre-emergent application to the weeds. Improved crop safety of the present invention is achieved even in the absence of a safener.

The microcapsule shell of the present invention may preferably comprise a polyurea polymer formed by a reaction between a principal polyamine, and optionally an auxiliary polyamine, having two or more amino groups per molecule and at least one polyisocyanate having two or more isocyanate groups per molecule. Release of the herbicide core material is controlled by the microcapsule shell wall, preferably without the need for mechanical release (microcapsule rupture).

In some embodiments, the microcapsules may be prepared by encapsulating core material in a shell wall formed by reacting polyamine component and a polyisocyanate component in a reaction medium in concentrations such that the reaction medium comprises a molar equivalent excess of amine groups compared to the isocyanate groups. More particularly, the molar concentration of amine groups from the principal polyamine and optional auxiliary polyamine and the molar concentration of isocyanate groups from the at least one polyisocyanate (i.e., one polyisocyanate, a blend of two polyisocyanates, a blend of three polyisocyanates, etc.) in the reaction medium is such that the ratio of the concentration of amine molar equivalents to the concentration of isocyanate molar equivalents is at least 1.1:1. The molar ratio of concentration of amine molar equivalents to concentration of isocyanate molar equivalents may be calculated according to the following equation:

$$\text{Molar Equivalents Ratio} = \frac{\text{amine molar equivalents}}{\text{polyisocyanate molar equivalents}} \quad (1)$$

In the above equation (1), the amine molar equivalents is calculated according to the following equation:

amine molar equivalents=Σ([polyamine]/equivalent weight).

In the above equation (1), the isocyanate molar equivalents is calculated according to the following equation:

isocyanate molar equivalents=Σ([polyisocyanate]/ equivalent weight)      i.

wherein the polyamine concentration and the polyisocyanate concentration refer to the concentration of each in the reaction medium and are each in grams/L. The equivalent weight is generally calculated by dividing the molecular weight in grams/mole by the number of functional groups per molecules and is in grams/mole. For some molecules, such as triethylenetetramine ("TETA") and 4,4'-diisocyanato-dicyclohexyl methane ("DES W"), the equivalent weight is equal to the molecular weight divided by the number of functional groups per molecule. For example, TETA has a molecular weight of 146.23 g/mole and 4 amine groups. Therefore, the equivalent weight is 36.6 g/mol. This calculation is generally correct, but for some materials, the actual equivalent weight may vary from the calculated equivalent weight. In some components, for example, the biuret-containing adduct (i.e., trimer) of hexamethylene-1, 6-diisocyanate, the equivalent weight of the commercially available material differs from the theoretical equivalent weight due to, for example, incomplete reaction. The theoretical equivalent weight of the biuret-containing adduct (i.e., trimer) of hexamethylene-1,6-diisocyanate is 159.5 g/mol. The actual equivalent weight of the trimer of hexamethylene-1,6-diisocyanate ("DES N3200"), the commercially available product, is about 183 g/mol. This actual equivalent weight is used in the calculations above. The actual equivalent weight may be obtained from the manufacturer or by titration with a suitable reactant by methods known in the art. The symbol, Σ, in the amine molar equivalents calculation means that the amine molar equivalents comprises the sum of amine molar equivalents for all polyamines in the reaction medium. Likewise, the symbol, Σ, in the isocyanate molar equivalents calculation means that the isocyanate molar equivalents comprises the sum of isocyanate molar equivalents for all polyisocyanates in the reaction medium.

It is advantageous to select a polyamine component and a polyisocyanate component such that the principal polyamine and optional auxiliary polyamine has an amine functionality of at least 2, i.e., 3, 4, 5 or more, and at least one of the polyisocyanates has an isocyanate functionality of at least 2, i.e., 2.5, 3, 4, 5, or more since high amine and isocyanate functionality increases the percentage of cross-linking occurring between individual polyurea polymers that comprise the shell wall. In some embodiments, the principal polyamine and optional auxiliary polyamine has an amine functionality of greater than 2 and the polyisocyanate is a mixture of polyisocyanates wherein each polyisocyanate has an isocyanate functionality of greater than 2. In other embodiments the principal polyamine and optional auxiliary polyamine comprises a trifunctional polyamine and the polyisocyanate component comprises one or more trifunctional polyisocyanates. In yet other embodiments, the shell wall is formed by the reaction between a polyisocyanate or mixture of polyisocyanates with a minimum average of 2.5 reactive groups per molecule and a principal polyamine and optional auxiliary polyamine with an average of at least three reactive groups per molecule. It is, moreover, advantageous to select concentrations of the polyamine component and the polyisocyanate component such that the polyisocyanate component is substantially completely reacted to form the polyurea polymer. Complete reaction of the polyisocyanate component increases the percentage of cross-linking between polyurea polymers formed in the reaction thereby providing structural stability to the shell wall. These factors, i.e., the ratio of weight of core material components compared to weight of shell wall components, the mean particle sizes of the herbicidal microcapsules, the degree of crosslinking, among other factors, may be selected to affect the release rate profile of the population of herbicidal microcapsules, thereby enabling the preparation of herbicidal microcapsules that balance enhanced crop safety and are still efficacious for weed control.

Preferably, the molar equivalents ratio of amine molar equivalents to isocyanate molar equivalents is at least about 1.15:1 or even at least about 1.20:1. In some embodiments, the molar equivalents ratio is less than about 1.7:1, less than about 1.6:1, less than about 1.5:1, less than about 1.4:1, or even less than about 1.3:1. In some embodiments, the molar equivalents ratio of amine molar equivalents to isocyanate molar equivalents in the polymerization medium is from 1.1:1 to about 1.7:1, from 1.1:1 to about 1.6:1, from 1.1:1 to about 1.5:1, from 1.1:1 to about 1.4:1, from 1.1:1 to about 1.3:1, from about 1.15:1 to about 1.7:1, from about 1.15:1 to about 1.6:1, from about 1.15:1 to about 1.5:1, from about 1.15:1 to about 1.4:1, or from about 1.15:1 to about 1.3:1 Examples of typical ratios include 1.1, 1.15:1, 1.2:1, 1.25:1, 1.3:1, 1.35:1, 1.4:1, 1.45:1 and 1.5:1. The molar equivalents ratio used in the practice of the present invention is greater than that typically employed in prior art compositions wherein a small stoichiometric excess of amine equivalents to isocyanate equivalents of about 1.01:1 to about 1.05:1 is used to ensure that the isocyanate is completely reacted. It is believed, without being bound to any particular theory, that increased excess of amine groups used in the present invention results in a significant number of unreacted amine functional groups thereby providing a shell having a large number of amine functional groups that are not cross-linked. It is believed, that the combination of a completely reacted and cross-linked polyisocyanate component and an amine component having a significant number of unreacted and uncross-linked functional groups may result in a structurally stable shell wall that is more flexible and/or supple and less likely to shear or rupture as compared to shell walls known in the art. It is further believed that unreacted amine groups may reduce the number of fissures or cracks in the shell wall thereby reducing leakage from the core.

In some other embodiments, the concentration of core material in comparison to the concentration of shell wall components in the reaction medium is controlled thereby resulting in a variation of the microcapsule shell wall thickness. Preferably, the reaction medium comprises core material and shell wall components in a concentration (weight) ratio from about 16:1 to about 3:1, such as from about 13:1 to about 8:1, from about 13:1 to about 6:1, from about 12:1 to about 6:1, or from about 10:1 to about 6:1. The ratio is calculated by dividing the core material concentration (grams/L), which consists of the herbicide active and any diluent solvent or solvents, in the reaction medium by the concentration of the shell wall components (grams/L) in the reaction medium. The shell wall components concentrations comprises the concentration of the polyamine component and the concentration of the polyisocyanate component. In general, it has been found that decreasing the ratio of core material to shell wall components tends to reduce, by increase of shell wall thickness, the release rate of the core materials. This tends to decrease both the crop injury and weed control, although the amounts of the effects are not always correlated.

In some embodiments, a diluent, such as a solvent, may be added to change the solubility parameter characteristics of the core material to increase or decrease the release rate of the active from the microcapsule, once release has been initiated. For example, the core material may comprise from 0% to about 35% by weight of a diluent, for example from 0.1 to about 25% by weight, from about 0.5% and about 20% by weight, or from about 1% and 10% by weight. In particular, the core material may comprise 0%, 0.5% 1%, 2%, 3%, 4%, 5%, 6%, 7%, 8%, 10%, 15%, 20%, 25%, 30% or even 35% diluent. In some embodiments, the weight ratio of total core material to diluent can be, for example, from 8 to 1, from 10 to 1, from 15 to 1, or from 20 to 1. In some embodiments, the diluent is a water-insoluble organic solvent having a solubility of less than 10, 5, 1, 0.5 or even 0.1 gram per liter at 25° C. Examples of suitable water-insoluble solvents include paraffinic hydrocarbons. Paraffinic hydrocarbons are preferably predominantly a linear or branched hydrocarbon. Examples include pentadecane and ISOPAR V.

A population of herbicidal microcapsules of the present invention may be prepared having at least one mean transverse dimension (e.g., diameter or mean particle size) of at least about 7 micrometers ("microns" or μm). The particle size may be measured with a laser light scattering particle size analyzer known to those skilled in the art. One example of a particle size analyzer is a Coulter LS Particle Size Analyzer. The microcapsules are essentially spherical such that the mean transverse dimension defined by any point on a surface of the microcapsule to a point on the opposite side of the microcapsule is essentially the diameter of the microcapsule. Preferably, the population of microcapsules has at least one mean transverse dimension, or mean particle size, of at least about 7 μm, more preferably at least about 8 μm, more preferably at least about 9 μm, more preferably at least about 10 μm. In preferred embodiments, the mean particle size of the population of microcapsules is less than about 15 μm, and more preferably less than 12 μm. In view thereof, a population of herbicidal microcapsules of the present invention preferably has a mean particle size of from about 7 pm to about 15 μm, from about 7 μm to about 12 μm, from about 8 μm to about 12 μm, or from about 9 μm to about 12 μm. In particularly preferred embodiments, the range varies from about 9 μm to about 11 μm.

The particle size of the microcapsules of the present invention are larger than that typically employed in the art and is generally achieved by varying the composition, as described above, and by controlling the reaction conditions such as, for example, blending speed, shear forces, mixer design and mixing times. In general, reduced blending speed, shear forces and mixing time favor the preparation of larger microcapsules.

In other embodiments of the present invention, two or more of the above variables can be manipulated in order to achieve the objects of the present invention. Manipulation of the following variable combinations is within the scope of the present invention: (1) (i) the ratio of molar equivalent amine groups to isocyanate groups and (ii) the weight ratio of the core herbicide to the shell wall components; (2)(i) the ratio of molar equivalent amine groups to isocyanate groups and (iii) the weight ratio of the core herbicide to the diluent (e.g., solvent); (3)(i) the ratio of molar equivalent amine groups to isocyanate groups and (iv) the microcapsule particle size; (4) (ii) the weight ratio of the core herbicide to the shell wall components and (iii) the weight ratio of the core herbicide to the diluent; (5) (ii) the weight ratio of the core herbicide to the shell wall components and (iv) the microcapsule particle size; (6) (iii) the weight ratio of the core herbicide to the diluent and (iv) the microcapsule particle size; (7)(i) the ratio of molar equivalent amine groups to isocyanate groups, (ii) the weight ratio of the core herbicide to the shell wall components, and (iii) the weight ratio of the core herbicide to the diluent; (8)(i) the ratio of molar equivalent amine groups to isocyanate groups, (ii) the weight ratio of the core herbicide to the shell wall components, and (iv) the microcapsule particle size; (9)(i) the ratio of molar equivalent amine groups to isocyanate groups, (iii) the weight ratio of the core herbicide to the diluent and (iv) the microcapsule particle size; (10) (ii) the weight ratio of the core herbicide to the shell wall components, (iii) the weight ratio of the core herbicide to the diluent and (iv) the microcapsule particle size; and (11)(i) the ratio of molar equivalent amine groups to isocyanate groups, (ii) the weight ratio of the core herbicide to the shell wall components, (iii) the weight ratio of the core herbicide to the diluent and (iv) the microcapsule particle size.

The release rate of the core material from the microcapsules can be controlled by selecting capsule properties and composition and by selecting process parameters as previously described. Therefore, by appropriate choice of the parameters discussed previously and below, it is possible to create formulations that have acceptable safety when applied as a broadcast spray to a field containing crops after emergence and maintain good weed control for agriculturally useful lengths of time.

The microcapsules of the present invention exhibit a release rate profile that provides a reduced rate of crop injury as compared to microcapsules known in the art. Under one theory, and without being bound to any particular theory, it is believed that increasing the mean particle size of the population of microcapsules decreases the total effective area per unit weight of the microcapsules. Since the diffusional release is proportional to the surface area, this tends, if everything else is held constant, to reduce the release rate. This in turn tends to reduce both the weed control and crop injury. However, it has been surprisingly discovered that the microcapsules of the present invention provide initial crop plant injury upon application that is even less than would be expected based only on a particle size-mediated release rate. It is believed, without being bound to any particular theory, that the combination of increased particle size and the shell characteristics resulting from a large excess of unreacted amine groups significantly reduces the amount of herbicide that the crop plants are initially exposed to upon postemergent application, thereby providing enhanced crop safety and minimized crop plant injury. It is believed that, as compared to prior art microcapsules, the flexible shell of the present invention is resistant to rupturing such that the amount of herbicide that crop plants are initially exposed to upon application of a herbicidal formulation containing the microcapsules is reduced. Additionally or alternatively, it is believed that the shell wall of the microcapsules is characterized by reduced fissuring that decreases leakage and flow of herbicide through the shell wall. In addition, optimizing the weight ratio of the core to the shell and the weight ratio of the core herbicide to the diluent (solvent) may further affect release rate and achieve the objects of the present invention.

The release rate profile for the purposes of estimating the potential for crop injury of the herbicidal active from a population of herbicidal microcapsules of the present invention may be measured in the laboratory using an agitated dissolution test apparatus known in the art, such as a SOTAX AT-7 (SOTAX Corporation; Horsham, Pa. 19044) or a HANSON SR8-PLUS (available from Hitachi). In the dissolution rate method protocol of the present invention, an aqueous slurry consisting of 1% by weight of the encapsulated acetamide herbicide active ingredient in an aqueous medium consisting of deionized water is prepared. For example, a 100 mL aqueous slurry would contain a total of about 1 gram acetamide herbicide. For microcapsules comprising 50% by weight acetamide, the aqueous slurry therefore would contain 2% by weight of the microcapsules. The aqueous slurry is placed a cell of the dissolution test apparatus and agitated at a temperature of 25° C. The aqueous slurry is agitated at a rate sufficient to maintain the microcapsule particles in suspension throughout the test without mechanical rupture of the microcapsule particles. For example, in the case of a SOTAX AT-7 agitated dissolution test apparatus, the agitator is rotated at about 150 RPM. Aliquots are removed periodically to determine the concentration of herbicide, e.g., at 0, 1, 2, 4, 6, and 24 hours. Each aliquot is filtered through a syringe filter (TARGET Cellulose Acetate 0.2 μm, ThermoFisher Scientific) to remove any capsules. The resulting solution is then analyzed for the active by standard analytical methods known in the art, such as, for instance, HPLC.

According to the method described herein for determining the release rate profile and based on experimental evidence, it is believed that good crop safety correlates to an encapsulated acetamide herbicide contained with a shell of limited permeability wherein a concentration of acetamide herbicide (e.g., acetochlor) in the test aliquot at 6 hours is less than about 100 ppm (about 1% of the total acetamide) and a concentration of acetamide in the test aliquot at 24 hours is less than about 150 ppm (1.5% of the total acetamide. Preferably, the concentration of acetamide in the test aliquot at 6 hours is less than about 75 ppm (0.75% of the total acetamide), and the concentration of acetamide in the test aliquot at 24 hours is less than about 125 ppm (1.25% of the total acetamide). More preferably, the concentration of acetamide in the test aliquot at 6 hours is less than about 60 ppm (0.60% of the total acetamide) and less than 100 ppm (1.00% of the total acetamide) for the test aliquot at 24 hours. Even more preferably, the concentration of acetamide in the test aliquot at 6 hours is less than about 50 ppm (0.50% of the total acetamide) and less than about 75 ppm (0.75% of the total acetamide) in the test aliquot at 24 hours. It has been observed that herbicidal microcapsules having release rate profiles with the above-described parameters generally provide both commercially acceptable plant safety and efficacy on weeds. By comparison, a sample of DEGREE Herbicide, a commercially available microencapsulated acetochlor formulation available from Monsanto Company, typically releases from about 125 ppm to about 140 ppm in the aliquot at 6 hours and about 200 ppm (close to saturation) in the aliquot at 24 hours.

Preparation of the encapsulated acetamide herbicides of the present invention is described in more detail below.

Acetamide Encapsulation

The polyurea polymer shells of the present invention include a repeat unit having the general structure (I):

Structure (I)

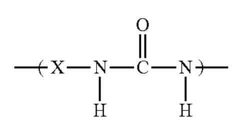

wherein X generally represents some portion, or portions, of the repeat units which, as further defined herein below, may be independently selected from a number of different entities (e.g., different hydrocarbylene linkers, such as aromatic, aliphatic, and cycloaliphatic linking groups, and moieties having combinations of aromatic, aliphatic, and cycloaliphatic linking groups). The shell encapsulates an acetamide-containing core material such that, once initiated, molecular diffusion of the acetamide through the shell wall is preferably the predominant release mechanism (as further described elsewhere herein). Thus, the shell is preferably structurally intact; that is, the shell is preferably not mechanically harmed or chemically eroded so as to allow the acetamide to release by a flow mechanism. Further, the shell is preferably substantially free of defects, such as micropores and fissures, of a size which would allow the core material to be released by flow. Micropores and fissures may form if gas is generated during a microcapsule wall-forming reaction. For example, the hydrolysis of an isocyanate generates carbon dioxide. Accordingly, the microcapsules of the present invention are preferably formed in an interfacial polymerization reaction in which conditions are controlled to minimize the in situ hydrolysis of isocyanate reactants. The reaction variables that may preferably be controlled to minimize isocyanate hydrolysis include, but are not limited to: selection of isocyanate reactants, reaction temperature, and reaction in the presence of an excess of amine molar equivalents over isocyanate molar equivalents.

As used herein, "flow" of the core material from the microcapsule generally refers to a stream of the material that drains or escapes through a structural opening in the shell wall. In contrast, "molecular diffusion" generally refers to a molecule of, for example, an acetanilide, which is absorbed into the shell wall at the interior surface of the wall and desorbed from the shell wall at the exterior surface of the wall.

As described above, the polyurea polymer is preferably the product of a reaction between a polyamine component comprising a principal polyamine (and optional auxiliary polyamine) having two or more amino groups per molecule and a poly isocyanate component comprising at least one polyisocyanate having two or more isocyanate groups per molecule. In some embodiments, the at least one polyisocyanate comprises a blend of two or more polyisocyanates. In some preferred embodiments, the blend of polyisocyanates comprises at least one diisocyanate, i.e., having two isocyanate groups per molecule, and at least one triisocyanate, having three isocyanate groups per molecule. Preferably, neither the principal amine nor the auxiliary amine are the product of a hydrolysis reaction involving any of the polyisocyanates with which they react to form the polyurea polymer. More preferably, the shell wall is substantially free of a reaction product of a polyisocyanate with an amine generated by the hydrolysis of the polyisocyanate. This in situ polymerization of an isocyanate and its derivative amine is less preferred for a variety of reasons described elsewhere herein.

The shell wall of the microcapsules may be considered "semi-permeable," which, as used herein, generally refers to a microcapsule having a half-life that is intermediate between release from a substantially impermeable microcapsule and a microcapsule that essentially allows the immediate release of core material (i.e., a microcapsule having a half-life of less than about 24 hours, about 18 hours, about 12 hours, or even about 6 hours). For example, a "semi-permeable" microcapsule may a half-life that is from about 5 to about 150 days, about 10 to about 125 days, about 25 to about 100 days, or about 50 to about 75 days.

Polyisocyanates

The polyurea polymer shell or wall of the microcapsules may be formed using one or more polyisocyanates, i.e., having two or more isocyanate groups per molecule. In some embodiments, the polyurea shell wall is formed using a blend of at least two polyisocyanates. In a preferred embodiment, the polyurea shell wall is formed in an interfacial polymerization reaction using at least one diisocyanate and at least one triisocyanate.

Polyisocyanates for use in forming the shell wall of the present invention have the following general structure (II):

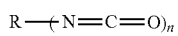

Structure (II)

wherein n is an integer that is at least 2, such as from 2 to five, from 2 to 4, and preferably is 2 or 3; and R is a group linking the 2 or more isocyanate groups together, including any aromatic, aliphatic, or cycloaliphatic groups, or combinations of any of aromatic, aliphatic, or cycloaliphatic groups, which are capable of linking the isocyanate groups together.

A wide variety of aliphatic diisocyanates, cycloaliphatic diisocyanates, and aromatic diisocyanates (wherein X is two in structure (II)) may be employed, for example, diisocyanates containing an aliphatic segment and/or containing a cycloaliphatic ring segment or an aromatic ring segment may be employed in the present invention as well.

General aliphatic diisocyanates include those having the following general structure (III):

Structure (III)

where n is an integer having an mean value of from about 2 to about 18, from about 4 to about 16, or about 6 to about 14. Preferably, n is six, i.e., 1,6-hexamethylene diisocyanate. The molecular weight of 1,6-hexamethylene diisocyanate is about 168.2 g/mol. Since 1,6-hexamethylene diisocyanate comprises 2 isocyanate groups per molecule, its equivalent weight is about 84.1 g/mol. The equivalent weight of the polyisocyanate is generally defined as the molecular weight divided by the number of functional groups per molecule. As noted above, in some polyisocyanates, the actual equivalent weight may differ from the theoretical equivalent weight, some of which are identified herein.

In certain embodiments, the aliphatic diisocyanates include dimers of diisocyanates, for example, a dimer having the following structure (IV):

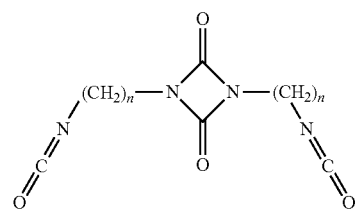

Structure (IV)

where n is an integer having an mean value of from about 2 to about 18, from about 4 to about 16, or about 6 to about 14. Preferably, n is six, i.e., structure (IV) is a dimer of 1,6-hexamethylene diisocyanate (molecular weight 339.39 g/mol; equivalent weight=183 g/mol).

A wide variety of cylcoaliphatic and aromatic diisocyanates may be used as well. In general, aromatic diisocyanates include those diisocynates wherein the R linking group contains an aromatic ring, and a cycloaliphatic diisocyanates include those diisocyanates wherein the R linking group contains a cylcoaliphatic ring. Typically, the R group structure in both aromatic and cycloaliphatic diisocyanates contains more moieties than just an aromatic or cycloaliphatic ring. The nomenclature herein is used to classify diisocyanates.

Certain commercially available aromatic diisocyanates comprise two benzene rings, which may be directly bonded to each other or connected through an aliphatic linking group having from one to about four carbon atoms. One such aromatic diisocyanate is 4,4'-diisocyanato-diphenylmethane (bis(4-isocyanatophenyl)methane (Molecular weight=250.25 g/mol; equivalent weight=125 g/mol) having the following structure (V):

Structure (V)

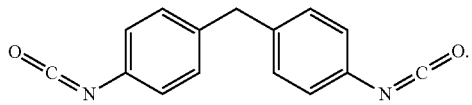

Aromatic diisocyanates having structures similar to structure (V) include 2,4'-diisocyanato-diphenylmethane (Molecular weight=250.25 g/mol; equivalent weight=125 g/mol) and 2,2'-diisocyanato-diphenyl methane (Molecular weight=250.25 g/mol; equivalent weight=125 g/mol).

Other aromatic diisocyanates, wherein the benzene rings are directly bonded to each other include, 4,4'-diisocyanato-1,1'-biphenyl and 4,4'-diisocyanato-3,3'-dimethyl-1,1'-biphenyl (Molecular weight=264.09 g/mol; equivalent weight=132 g/mol), which has the following structure (VI):

Structure (VI)

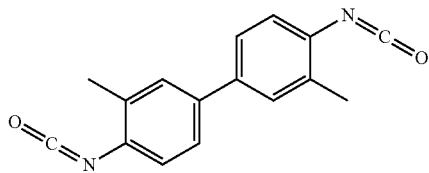

Yet another aromatic diisocyanate is dianisidine diisocyanate (4,4'-diisocyanato-3,3'-dimethoxybiphenyl) (Molecular weight=296 g/mol; equivalent weight=148 g/mol) having the following structure (VII):

Structure (VII)

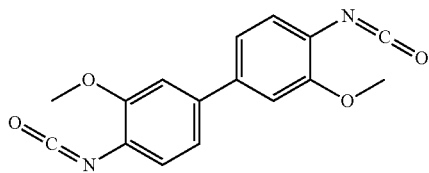

Certain commercially available aromatic diisocyanate comprise a single benzene ring. The isocyanate groups may be directly bonded to the benzene ring or may be linked through aliphatic groups having from one to about four carbon atoms. An aromatic diisocyanate having a single benzene ring is meta-phenylene diisocyanate (1,3-diisocyanatobenzene) (Molecular weight=160.1 g/mol; equivalent weight=80 g/mol) having the structure (VIII):

Structure (VIII)

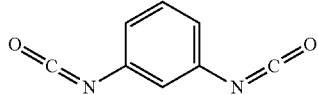

Similar aromatic diisocyanates include para-phenylene diisocyanate (Molecular weight=160.1 g/mol; equivalent weight=80 g/mol), 2,4-toluene diisocyanate (2,4-diisocyanato-1-methylbenzene) (Molecular weight=174.2 g/mol; equivalent weight=85 g/mol), 2,6-toluene diisocyanate (Molecular weight=174.2 g/mol; equivalent weight=85 g/mol), and 2,4,6-triisopropyl-m-phenylene isocyanate. Similar diisocyanates having aliphatic groups linking the isocyanates to the benzene ring include 1,3-xylylene diisocyanate, 1,4-xylylene diisocyanate, tetramethyl-meta-xylylene diisocyanate, tetramethyl-para-xylylene diisocyanate, and meta-tetramethylxylene diisocyanate (1,3-bis(2-isocyanatopropan-2-yl)benzene).

Cycloaliphatic diisocyanate may include one or more cycloaliphatic ring groups having from four to about seven carbon atoms. Typically, the cycloaliphatic ring is a cyclohexane ring. The one or more cyclohexane rings may be bonded directly to each other or through an aliphatic linking group having from one to four carbon atoms. Moreover, the isocyanate groups may be directly bonded to the cycloaliphatic ring or may be linked through an aliphatic group having from one to about four carbon atoms. An example of a cycloaliphatic isocyanate is a 4,4'-diisocyanato-dicyclohexyl methane (bis(4-isocyanatocyclohexyl)methane) such as Desmodur W (Miles) having the structure (IX):

Structure (IX)

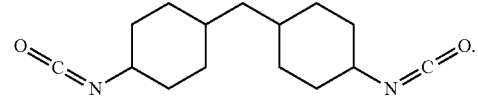

Desmodur W has an approximate molecular weight of 262.35 and an approximate equivalent weight of 131.2 g/mole. Additional cycloaliphatic diisocyanates include 1,3-bis(isocyanatomethyl)cyclohexane and isophorone diisocyanate (5-isocyanato-1-(isocyanatomethyl)-1,3,3-trimethylcyclohexane).

Certain aliphatic triisocyanates include, for example, trifunctional adducts derived from linear aliphatic diisocyanates. The linear aliphatic diisocyanate may have the following structure (III):

$$O=C=N-(CH_2)_n-N=C=O \qquad \text{Structure (III)}$$

where n is an integer having an mean value of from about 2 to about 18, from about 4 to about 16, or about 6 to about 14. A particularly preferred linear aliphatic diisocyanate of structure (III) useful for preparing aliphatic triisocyanates is a trimer of hexamethylene-1,6-diisocyanate. The aliphatic triisocyanates may be derived from the aliphatic isocyanate alone, i.e., dimers, trimers, etc., or they may be derived from a reaction between the aliphatic isocyanate of structure (I), and a coupling reagent such as water or a low molecular weight triol like trimethylolpropane, trimethylolethane, glycerol or hexanetriol.

An exemplary aliphatic triisocyanate, wherein n is 6, is the biuret-containing adducts (i.e., trimers) of hexamethylene-1,6-diisocyanate corresponding to the structure (X):

Structure (X)

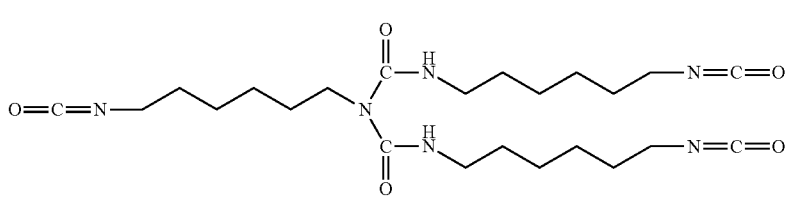

This material is available commercially under the trade name Desmodur N3200 (Miles) or Tolonate HDB (Rhone-Poulenc). Desmodur N3200 has an approximate molecular weight of 478.6 g/mole. The commercially available Desmodur N3200 has an approximate equivalent weight of 191 g/mol (Theoretical equivalent weight is 159 g/mol).

Another aliphatic triisocyanate derived from the aliphatic isocyanate of structure (III) corresponds to the following general structure:

Structure (XI)

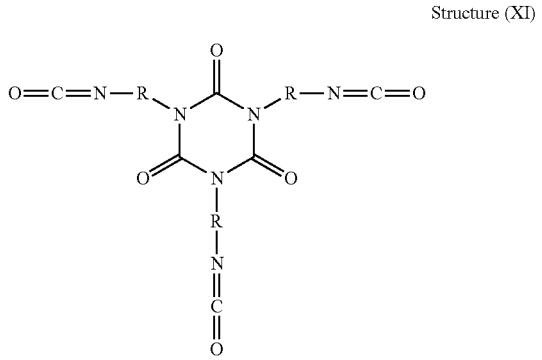

A specific aliphatic triisocyanate of the above structure wherein the R groups are linear hydrocarbons having six carbon atoms (trimers of hexamethylene-1,6-diisocyanate) having the name HDI isocyanurate trimer, which is available commercially under the trade names Desmodur N3300 (Miles) or Tolonate HDT (Rhone-Poulenc). Desmodur N3300 has an approximate molecular weight of 504.6 g/mol, and an equivalent weight of 168.2 g/mol.

Another exemplary aliphatic triisocyanate is the triisocyanate adduct of trimethylolpropane and hexamethylene-1,6-diisocyanate corresponding to the structure (XII):

Structure (XII)

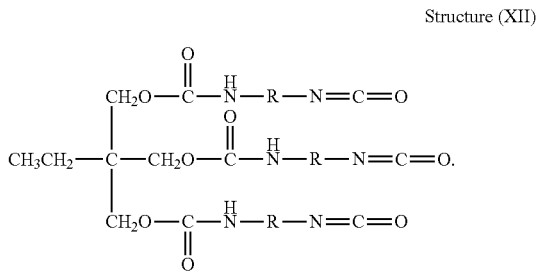

Aromatic triisocyanates containing an aromatic moiety are also useful in the present invention, including for example those which contain or comprise polymethylenepolyphenyl polyisocyanate (CAS #9016-87-9, 4,4'-(4-isocyanato-1,3-phenylene) bis(methylene) s(isocyanatobenzene)) having the structure (XIII):

Structure (XIII)

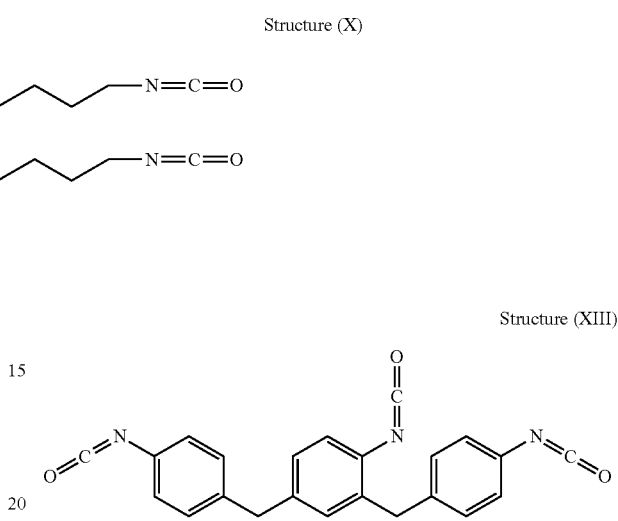

Isocyanates with an aromatic moiety may have a tendency to undergo in situ hydrolysis at a greater rate than aliphatic isocyanates. Since the rate of hydrolysis is decreased at lower temperatures, isocyanate reactants are preferably stored at temperatures no greater than about 50° C., and isocyanate reactants containing an aromatic moiety are preferably stored at temperatures no greater than about 20° C. to about 25° C., and under a dry atmosphere.

Still other polyisocyanates include toluene diisocyanate adducts with trimethylolpropane, xylene diisocyanate and polymethylenepolyphenyl polyisocyanate-terminated polyols.

It is to be noted that selection of the polyisocyanate, or blend of polyisocyanates, to be used may be determined experimentally using means known in the art (see, e.g., U.S. Pat. No. 5,925,595, the entire contents of which are incorporated herein for all relevant purposes). Where a blend of a triisocyanate and a diisocyanate is used, the ratio of the triisocyanate to the diisocyanate, on an isocyanate equivalent basis, is between about 90:10 and about 30:70.

Amines

A. Principal Amines

In some preferred embodiments of the present invention, the polyamine component consists essentially of the principal amine. Similarly stated, in some embodiments, the polyamine component is a principal amine in the absence of one or more auxiliary amines. The polyurea polymers, from which the microcapsule shell wall is prepared or formed, may comprise an amine or polyfunctional amine precursor (e.g., monomer). Among the amines or polyfunctional amines that may be employed to prepare a preferred microcapsule of the present invention are, for example, linear alkylamines or polyalkylamines, having the general structure:

  Structure (XIV)

wherein "X" is selected from the group consisting of $-(CH_2)_a-$ and $-(C_2H_4)-Y-(C_2H_4)-$; "a" is an integer having a value from about 1 to about 8, 2 to about 6, or about 3 to about 5; and, "Y" is selected from the group consisting of $-S-S-$, $-(CH_2)_b-Z-(CH_2)_b-$, and $-Z-(CH_2)_a-Z-$, wherein "b" is an integer having a value from 0 to 4, or from 1 to 3, "a" is as defined above, and "Z" is selected from the group consisting of —N(H)—, —O—, and —S—.

Examples of such amines or polyfunctional amines that may typically be employed in the present invention include substituted and unsubstituted polyethyleneamines, such as (i) amines of the structure $NH_2(CH_2CH_2NH)_mCH_2CH_2NH_2$ where m is 1 to 5, 1 to 3, or 2, (ii) diethylene triamine (molecular weight=103.17 g/mol, equivalent weight=34.4 g/mol) and (iii) triethylene tetramine (molecular weight=146.23 g/mol, equivalent weight=36.6 g/mol), as well as substituted and unsubstituted polypropylenimines. However, it is to be noted that other, similar substituted and unsubstituted polyfunctional amines are also useful, including for example iminobispropylamine, bis(hexamethylene) triamine, cystamine, triethylene glycol diamine (e.g. Jeffamine EDR-148 from Huntsman Corp., Houston, TX) and the alkyl diamines, triamine and tetramine having a main alkyl chain of from about 2 to about 6, or about 2 to about 4, carbons in length (e.g., from ethylene diamine up to hexamethylene diamine, triamine or tetramine, with a few number of carbons typically being preferred and/or tetramines typically being preferred over triamines). The principal polyamine may comprise one or more of any of the above described amines having the general structure (XIV). Among the preferred amines are included, for example, substituted or unsubstituted polyethyleneamine, polypropyleneamine, diethylene triamine and triethylene tetramine.

B. Auxiliary Amines

In some optional embodiments of the present invention, the polyamine component comprises a principal amine and one or more auxiliary amines. Where the polyamine component comprises a principal amine and an auxiliary amine, the permeability of the shell wall, or the release rate of the core material, may be affected, for example, by varying the relative amounts of 2 or more amines used in the shell wall-forming polymerization reaction (see, e.g., U.S. Patent Pub. No. 2004/0137031 A1, the entire contents of which is incorporated by reference herein). Accordingly, in addition to those principal amines set forth above, auxiliary amines, such as a polyalkyleneamine or an epoxy-amine adduct, may be optionally included in combination with the principal amine to provide microcapsules having an altered shell wall permeability or release rate as compared to a shell wall prepared from an amine source consisting essentially of a principal amine, in addition to the permeability imparted thereto upon activation of the microcapsule (e.g., by cleavage of the blocking group from the polymer backbone).

This permeability, or release rate, may change (e.g., increase) as the ratio of the auxiliary amine to a principal amine increases. It is to be noted, however, that alternatively or additionally, as described in greater detail elsewhere herein, the rate of permeability may be further optimized by altering the shell wall composition by, for example, (i) the type of isocyanate employed, (ii) using a blend of isocyanates, (iii) using an amine having the appropriate hydrocarbon chain length between the amino groups, and/or (iv) varying the ratios of the shell wall components and core components, all as determined, for example, experimentally using means standard in the art.

In some embodiments, the permeability-altering or auxiliary amine may be a polyalkyleneamine prepared by reacting an alkylene oxide with a diol or triol to produce a hydroxyl-terminated polyalkylene oxide intermediate, followed by amination of the terminal hydroxyl groups.

Alternatively, the auxiliary amine may be a polyetheramine (alternatively termed a polyoxyalkyleneamine, such as for example polyoxypropylenetri- or diamine, and polyoxyethylenetri- or diamine) having the following structure (XV):

Structure (XV)

wherein: c is a number having a value of 0 or 1; "$R^1$" is selected from the group consisting of hydrogen and $CH_3(CH_2)_d$—; "d" is a number having a value from 0 to about 5; "$R^2$" and "$R^3$" are

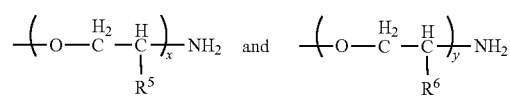

respectively; "$R^4$" is selected from the group consisting of hydrogen and;

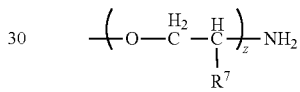

wherein "$R^5$", "$R^6$", and "$R^7$" are independently selected from a group consisting of hydrogen, methyl, and ethyl; and, "x", "y", and "z" are numbers whose total ranges from about to 2 to about 40, or about 5 to about 30, or about 10 to about 20.

In some embodiments, the value of x+y+z is preferably no more than about 20, or more preferably no more than about 15 or even about 10. Examples of useful auxiliary amine compounds having this formula include amines of the Jeffamine ED series (Huntsman Corp., Houston, Tex.). One of such preferred amines is Jeffamine T-403 (Huntsman Corp., Houston, Tex.), which is a compound according to this formula wherein c, g and h are each 0, R1 is $CH_3CH_2$ (i.e., $CH_3(CH_2)d$, where d is 1), $R_5$, $R_6$, and $R_7$ are each a methyl group and the average value of x+y+z is from about 5 and about 6.

The reaction of a polyfunctional amine with an epoxy functional compound has been found to produce epoxy-amine adducts which are also useful as auxiliary amines. Epoxy-amine adducts are generally known in the art. (See, e.g., Lee, Henry and Neville, Kris, Aliphatic Primary Amines and Their Modifications as Epoxy-Resin Curing Agents in Handbook of Epoxy Resins, pp. 7-1 to 7-30, McGraw-Hill Book Company (1967).) Preferably, the adduct has a water solubility as described for amines elsewhere herein. Preferably, the polyfunctional amine which is reacted with an epoxy to form the adduct is an amine as previously set forth above. More preferably, the polyfunctional amine is diethylenetriamine or ethylenediamine. Preferred epoxies include ethylene oxide, propylene oxide, styrene oxide, and cyclohexane oxide. Diglycidyl ether of bisphenol A (CAS #1675-54-3) is a useful adduct precursor when reacted with an amine in an amine to epoxy group ratio preferably of at least about 3 to 1.

It is to be noted, however, that permeability may also be decreased in some instances by the addition of an auxiliary amine. For example, it is known that the selection of certain ring-containing amines as the permeability-altering or auxiliary amine is useful in providing microcapsules with release rates which decrease as the amount of such an amine increases, relative to the other, principal amine(s) therein. Preferably, the auxiliary amine is a compound selected from the group consisting of cycloaliphatic amines and arylalkyl amines. Aromatic amines, or those having the nitrogen of an amine group bonded to a carbon of the aromatic ring, may not be universally suitable. Exemplary, and in some embodiments preferred, cycloaliphatic amines include 4,4'-diaminodicyclohexyl methane, 1,4-cyclohexanebis(methylamine) and isophorone diamine (5-Amino-1,3,3-trimethylcyclohexanemethylamine; molecular weight=170.30 g/mol; equivalent weight=85.2 g/mol). Exemplary, and in some embodiments preferred, arylalkyl amines have the structure of the following structure (XVI):

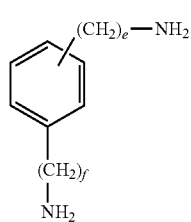

Structure (XVI)

wherein "e" and "f" are integers with values which independently range from about 1 to about 4, or about 2 to about 3. Meta-xylylene diamine, from Mitsubishi Gas Co., Tokyo, JP, is a preferred example of an arylalkyl amine (molecular weight=136.19 g/mol; equivalent weight=68.1 g/mol). Another example is para-xylylenediamine. Alkyl substituted arylalkyl polyamines include 2,3,5,6-tetramethyl-1,4-xylylenediamine and 2,5-dimethyl-1,4-xylylenediamine.

C. Amine Properties

Preferably, the principal amine (and optional auxiliary polyamine) has at least about two amino groups or functionalities, and even more preferably, the amine comprises at least three amino groups. Without being held to any particular theory, it is generally believed that in an interfacial polymerization as described herein, the effective functionality of a polyfunctional amine is typically limited to only slightly higher than about 2 and less than about 4. This is believed to be due to steric factors, which normally prevent significantly more than about 3 amino groups in the polyfunctional amine shell wall precursor from participating in the polymerization reaction.

It is to be further noted that the molecular weight of the amine monomer, which may or may not possess an amine blocking group thereon, is preferably less than about 1000 g/mole, and in some embodiments is more preferably less than about 750 g/mole or even 500 g/mole. For example, the molecular weight of the amine monomer, which may or may not have one or more block amine functionalities therein, may range from about 75 g/mole to less than about 750 g/mole, or from about 100 g/mole to less than about 600 g/mole, or from about 150 g/mole to less than about 500 g/mole. Equivalent weights (the molecular weight divided by the number of amine functional groups) generally range from about 20 g/mole to about 250 g/mole, such as from about 30 g/mole to about 125 g/mole. Without being held to a particular theory, it is generally believed that steric hindrance is a limiting factor here, given that bigger molecules may not be able to diffuse through the early-forming protoshell wall to reach, and react to completion with, the isocyanate monomer in the core during interfacial polymerization.

Core Material Composition

Generally speaking, useful herbicidal core materials include those that are a single phase liquid at temperatures of less than about 80° C. Preferably, the core material is a liquid at temperatures of less than about 65° C. More preferably, the core material is a liquid at temperatures of less than about 50° C. The core material may also comprise solids suspended in a liquid phase. Whether liquid or solids in a liquid phase, the core material preferably has a viscosity such that it flows easily to facilitate transport by pumping and to facilitate the creation of an oil in water emulsion as part of the method for preparation of microcapsules discussed herein. Thus, the core material preferably has a viscosity of less than about 1000 centipoise (cps) (e.g., less than about 900, 800, 700, 600 or even 500 cps) at the temperature at which the emulsion is formed and the polymerization reaction occurs, typically from about 25° C. to about 65° C., typically, from about 40° C. to about 60° C. Preferably, the core material is water-immiscible, a property which promotes encapsulation by interfacial polymerization. Water-immiscibility refers to materials that have a relatively low water solubility at about 25° C., for example, less than about 500 mg/L, preferably less than about 250 mg/L, even more preferably less than about 100 mg/L. Certain core materials have even lower water solubilities, such as acetochlor, which is less than 25 mg/L at 25° C. In some preferred embodiments, the acetamide herbicidal core materials suitable for the practice of the present invention include dimethenamid, napropamide, pronamide and acetanilide herbicides such as acetochlor, alachlor, butachlor, butenachlor, delachlor, diethatyl, dimethachlor, mefenacet, metazochlor, metolachlor, pretilachlor, propachlor, propisochlor, prynachlor, terbuchlor, thenylchlor and xylachlor, mixtures thereof and stereoisomers thereof. Preferred acetamide herbicides include dimethenamid and dimethenamid-P and preferred acetanilide herbicides include acetochlor, metolachlor and S-metolachlor.

The core material may comprise multiple compounds for release (e.g., an acetamide and one or more additives compatible therewith which act to enhance its bioefficacy on weeds and/or reduce crop injury). For example, in some embodiments, the core material optionally comprises a safener. Suitable safeners include, for example, furilazole ((RS)-3-(dichloroacetyl)-5-(2-furanyl)-2,2-dimethyl-1,3-oxazolidine 95%), commercially available from Monsanto Company; AD 67 (4-(dichloroacetyl)-1-oxa-4-azaspiro[4,5]decane); benoxacor (CGA 154281, (RS)-4-dichloroacetyl-3,4-dihydro-3-methyl-2H-1,4-benzoxazine); cloquintocet-mexyl (CGA 184927, (5-chloroquinolin-8-yloxy)acetic acid); cyometrinil (CGA 43089, (Z)-cyanomethoxyimino (phenyl)acetonitrile); cyprosulfamide (N-[4-(cyclopropyl-carbamoyl)phenylsulfonyl]-o-anisamide); dichlormid (DDCA, R25788, N,N-diallyl-2,2-dichloroacetamide); dicyclonon ((RS)-1-dichloroacetyl-3,3,8a-trimethylperhydropyrrolo[1,2-a]pyrimidin-6-one); dietholate (O,O-diethyl O-phenyl phosphorothioate) fenchlorazole-ethyl (HOE 70542, 1-(2,4-dichlorophenyl)-5-trichloromethyl-1H-1,2,4-triazole-3-carboxylic acid); fenclorim (CGA 123407 4, 6-dichloro-2-phenylpyrimidine); flurazole (benzyl 2-chloro-4-trifluoromethyl-1,3-thiazole-5-carboxylate); fluxofenim (CGA 133205, 4'-chloro-2,2,2-trifluoroacetophenone (EZ)-O-1,3-dioxolan-2-ylmethyloxime); isoxadifen (4,5-dihydro- 5,5-diphenyl-1,2-oxazole-3-carboxylic acid); mefenpyr ((RS)-1-(2,4-dichlorophenyl)-5-methyl-2-pyrazoline-3,5-dicarboxylic acid); mephenate (4-chlorophenyl methylcarbamate); MG 191; naphthalic anhydride; oxabetrinil (CGA 92194, (Z)-1,3-dioxolan-2-ylmethoxyimino(phenyl)acetonitrile); and others as are known in the art. It is to be noted that the herbicidal microcapsules, through selection of processing and structural parameters, achieve commercially acceptable crop safety even in the absence of a safener. Therefore, the safener is an optional core material.

It is to be further noted, as previously described, that the core material may optionally comprise a diluent. The diluent may be added to change the solubility parameter characteristics of the core material to increase or decrease the release rate of the active from the microcapsule, once release has been initiated. The preferred diluent content in the core material is as previously described.

The diluent may be selected from essentially any of those known in the art. The compatibility of the diluent with the core material (e.g., the acetamide active) and/or the shell wall may be determined, for example, experimentally using means standard in the art (see, e.g., U.S. Patent Pub. No. 2004/0137031 A1 and U.S. Pat. No. 5,925,595, the entire contents of which are incorporated herein for all relevant purposes). Exemplary diluents include, for example: alkyl-substituted biphenyl compounds (e.g., SureSol 370, commercially available from Koch Co.); normal paraffin oil (e.g., NORPAR 15, commercially available from Exxon); mineral oil (e.g., ORCHEX 629, commercially available from Exxon); isoparaffin oils (e.g., ISOPAR V and ISOPAR L, commercially available from Exxon); aliphatic fluids or oils (e.g., EXXSOL D110 and EXXSOL D130, commercially available from Exxon); alkyl acetates (e.g., EXXATE 1000, formerly commercially available from Exxon); aromatic fluids or oils (A 200, commercially available from Exxon); citrate esters (e.g., Citroflex A4, commercially available from Morflex); and, plasticizing fluids or oils used in, for examples, plastics (typically high boiling point esters).

Preparation of Microcapsules and Dispersions Thereof

In general, an aqueous dispersion of the microcapsules of the present invention may be produced by an interfacial polymerization reaction, either continuously or batchwise, using means generally known in the art. However, preferably a principal amine is polymerized with one or more polyisocyanates at the interface of an oil-in-water emulsion. The discontinuous oil phase (also referred to herein as "internal phase") preferably comprises one or more polyisocyanates and a continuous aqueous phase (also referred to herein as "external phase") comprises the principal amine. The oil phase further comprises a core material that preferably comprises an acetamide herbicide as the active ingredient. In other embodiments, when more than one amine is used (e.g., a principal amine and an auxiliary amine), these amines may be reacted in a ratio such that the microcapsules have a predetermined permeability with respect to the core material, either prior to activation or additionally upon activation.

In this regard it is to be noted that preferably the amine is not the hydrolysis product of the isocyanate. Rather, it is preferred that the reactants are selected from, for example, the amines and polyisocyanates disclosed elsewhere herein.

The oil-in-water emulsion is preferably formed by adding the oil phase to the continuous aqueous phase to which an emulsifying agent has been added (e.g., previously dissolved therein). The emulsifying agent is selected to achieve the desired oil droplet size in the emulsion. The size of the oil droplets in the emulsion is impacted by a number of factors in addition to the emulsifying agent employed and determines the size of microcapsules formed by the process, as described elsewhere herein. The emulsifying agent is preferably a protective colloid. Polymeric dispersants are preferred as protective colloids. Polymeric dispersants provide steric stabilization to an emulsion by adsorbing to the surface of an oil drop and forming a high viscosity layer which prevents drops from coalescing. Polymeric dispersants may be surfactants and are preferred to surfactants which are not polymeric, because polymeric compounds form a stronger interfacial film around the oil drops. If the protective colloid is ionic, the layer formed around each oil drop will also serve to electrostatically prevent drops from coalescing. SOKALAN (BASF), a maleic acid-olefin copolymer, is a preferred protective colloid, as is Invalon and Lomar D (Cognis).

Other protective colloids useful in this invention are gelatin, casein, polyvinyl alcohol, alkylated polyvinyl pyrrolidone polymers, maleic anhydride-methyl vinyl ether copolymers, styrene-maleic anhydride copolymers, maleic acid-butadiene and diisobutylene copolymers, sodium and calcium lignosulfonates, sulfonated naphthalene-formaldehyde condensates, modified starches, and modified cellulosics like hydroxyethyl or hydroxypropyl cellulose, and carboxy methyl cellulose.

To prepare microcapsules of a preferred mean diameter, the selection of a protective colloid and the conditions of the emulsification step are to be given consideration. For example, the quality of the emulsion, and hence the size of the microcapsules produced, is dependent to some extent upon the stirring operation used to impart mechanical energy to the emulsion. Preferably, the emulsification is accomplished with a high shear disperser. Generally, the microcapsules produced by this process have a size roughly approximated by the size of the oil drops from which they formed. Therefore, the emulsion is typically mixed to create oil drops having a mean diameter preferably at least about 5 μm, but typically less than about 15 μm.

The time that the emulsion remains in a high shear mixing zone is preferably limited to only the time required to create an emulsion having the desired droplet size. The longer the emulsion remains in the high shear mixing zone, the greater the degree to which the polyisocyanate will hydrolyze and react in situ. A consequence of in situ reaction is the premature formation of shell walls. Shell walls formed in the high shear zone may be destroyed by the agitation equipment, resulting in wasted raw materials and an unacceptably high concentration of unencapsulated core material in the aqueous phase. Typically, mixing the phases with a Waring blender for about 45 seconds to about 90 seconds, or with an in-line rotor/stator disperser having a shear zone dwell time of much less than a second, is sufficient. After mixing, the emulsion is preferably agitated sufficiently to maintain a vortex.

The time at which the amine source is added to the aqueous phase is a process variable that may affect, for example, the size distribution of the resulting microcapsules and the degree to which in situ hydrolysis occurs. Contacting the oil phase with an aqueous phase which contains the amine source prior to emulsification initiates some polymerization at the oil/water interface. If the mixture has not been emulsified to create droplets having the preferred size distribution, a number of disfavored effects may result, including but not limited to: the polymerization reaction wastefully creates polymer which is not incorporated into shell walls; oversized microcapsules are formed; or, the subsequent emulsification process shears apart microcapsules which have formed.

In some instances, the negative effects of premature amine addition may be avoided by adding a non-reactive form of the amine to the aqueous phase and converting the amine to its reactive form after emulsion. For example, the salt form of amine reactants may be added prior to emulsification and thereafter converted to a reactive form by raising the pH of the emulsion once it is prepared. This type of process is disclosed in U.S. Pat. No. 4,356,108, which is herein incorporated by reference in its entirety. However, it is to be noted that the increase in pH required to activate amine salts may not exceed the tolerance of the protective colloid to pH swings, otherwise the stability of the emulsion may be compromised.

Accordingly, it may be preferable for the amine source to be added after the preparation of the emulsion. More preferably, the amine source may be added as soon as is practical after a suitable emulsion has been prepared. Otherwise, the disfavored in situ hydrolysis reaction may be facilitated for as long as the emulsion is devoid of amine reactant, because the reaction of isocyanate with water proceeds unchecked by any polymerization reaction with amines. Therefore, amine addition is preferably initiated and completed as soon as practical after the preparation of the emulsion.

There may be, however, situations where it is desirable to purposefully increase the period over which the amine source is added. For example, the stability of the emulsion may be sensitive to the rate at which the amine is added. Alkaline colloids, like SOKALAN, can generally handle the rapid addition of amines. However, rapid addition of amines to an emulsion formed with non-ionic colloids or PVA cause the reaction mixture to gel rather than create a dispersion. Furthermore, if relatively "fast reacting" polyisocyanates are used (e.g., polyisocyanates containing an aromatic moiety), gelling may also occur if the amines are added too quickly. Under the above circumstances, it is typically sufficient to extend the addition of the amine over a period of from about 3 to about 15 minutes, or from about 5 to about 10 minutes. The addition is still preferably initiated as soon as is practical after the emulsion has been prepared.

The viscosity of the external phase is primarily a function of the protective colloid present. The viscosity of the external phase is preferably less than about 50 cps, more preferably less than about 25 cps, and still more preferably less than about 10 cps at the temperature of emulsion preparation, which is typically from about 25° C. to about 65° C., preferably from about 40° C. to about 60° C. The external phase viscosity is measured with a Brookfield viscometer with a spindle size 1 or 2 and at about 20 to about 60 rpm speed. After reaction and without additional formulation, the microcapsule dispersion which is prepared by this process preferably has a viscosity of less than about 400 cps (e.g., less than about 350 cps, about 300 cps, about 250 cps, or even about 200 cps) at the temperature of emulsion preparation. More preferably the dispersion viscosity is from about 100 to about 200 cps, or from 125 to about 175 cps at the temperature of emulsion preparation.

It is preferred that the oil phase is in the liquid state as it is blended into the aqueous phase. Preferably, the acetamide herbicide or other active ingredient is melted or dissolved or otherwise prepared as liquid solution prior to the addition of the isocyanate reactant. To these ends, the oil phase may require heating during its preparation.

The discontinuous oil phase may also be a liquid phase which contains solids. Whether liquid, low melting solid, or solids in a liquid, the discontinuous oil phase preferably has a viscosity such that it flows easily to facilitate transport by pumping and to facilitate the creation of the oil-in-water emulsion. Thus, the discontinuous oil phase preferably has a viscosity of less than about 1000 cps (e.g., less than about 900 cps, about 800 cps, about 700 cps, about 600 cps, or even about 500 cps) at the temperature of emulsion preparation, which is typically from about 25° C. to about 65° C., preferably from about 40° C. to about 60° C.

To minimize isocyanate hydrolysis and in situ shell wall formation, a cooling step subsequent to heating the oil phase is preferred when the oil phase comprises a polyisocyanate comprising an aromatic moiety, because isocyanates comprising an aromatic moiety undergo the temperature-dependent hydrolysis reaction at a faster rate than non-aromatic isocyanates. It has been discovered that the hydrolysis reaction has a negative effect on the preparation of the microcapsules of the present invention. Among other problems, isocyanates hydrolyze to form amines that compete in situ with the selected amine in the polymerization reaction, and the carbon dioxide generated by the hydrolysis reaction may introduce porosity into the prepared microcapsules. Therefore, it is preferred to minimize the hydrolysis of isocyanate reactants at each step of the process of the present invention. Since the hydrolysis reaction rate is directly dependent on the temperature, it is particularly preferred that the internal phase (i.e., discontinuous phase) be cooled to less than about 50° C. subsequent to mixing the polyisocyanate and the core material. It is also preferred that the internal phase be cooled to less than about 25° C. if isocyanates comprising an aromatic moiety are used.

Hydrolysis may also be minimized by avoiding the use of oil phase compositions in which water is highly soluble. Preferably water is less than about 5% by weight soluble in the oil phase at the temperature of the emulsion during the reaction step. More preferably water is less than about 1% soluble in the oil phase. Still more preferably water is less than about 0.1% soluble in the oil phase. It is preferred that the oil phase has a low miscibility in water. Low miscibility in water also promotes the formation of a useful emulsion.

It is preferred that the principal polyamine (and optional auxiliary polyamine) is sufficiently mobile across an oil-water emulsion interface. Thus, it is preferred that amines selected for the wall-forming reaction have an n-octanol/water partition coefficient wherein the base-10 log of the partition coefficient is between about −4 and about 1. It is also preferred that the reaction occur on the oil side of the oil-water interface, but is it believed that at partition coefficient values lower than about −4 the amines may not be soluble enough in the oil phase to participate sufficiently in the wall-forming reaction. Therefore, the reaction may proceed too slowly to be economical, or the disfavored in situ reaction may predominate. Furthermore, at partition coefficient values above about 1, the amines may not be sufficiently soluble in the water phase to be evenly distributed enough throughout the aqueous phase to facilitate a consistent reaction rate with all the oil particles. Therefore, more preferably the base-10 log of the partition coefficient is between about −3 and about 0.25, or about −2 and about 0.1.

To further reduce the amount of poyisocyanate hydrolysis and in situ reaction, the reaction is preferably run at as low of a temperature as economics based on the reaction rate will allow. For example, the reaction step may preferably be performed at a temperature from about 40° C. to about 65° C. More preferably, the reaction step may be performed at a temperature from about 40° C. to about 50° C.

The reaction step may preferably be performed to convert at least about 90% of the polyisocyanate. The reaction step may more preferably be performed to convert at least about 95% of the polyisocyanate. In this regard it is to be noted that the conversion of polyisocyanate may be tracked by monitoring the reaction mixture around an isocyanate infrared absorption peak at 2270 cm$^{-1}$, until this peak is essentially no longer detectable. The reaction may achieve 90% conversion of the isocyanate at a reaction time which is within the range of, for example, about one-half hour to about 3 hours, or about 1 to about 2 hours, especially where the core material comprises an acetanilide.

Liquid Microcapsule Dispersions: Parameters and Compositions

The microcapsules of the present invention comprise a water-immiscible, agricultural chemical-containing core material encapsulated by a polyurea shell wall, which is preferably substantially non-microporous, such that core material release occurs by a molecular diffusion mechanism, as opposed to a flow mechanism through a pore or rift in the polyurea shell wall. As noted herein, the shell wall may preferably comprise a polyurea product of a polymerization of one or more polyisocyanates and a principal polyamine (and optional auxiliary polyamine). Additionally, a further embodiment of the present invention comprises a liquid dispersion of the microcapsules of the present invention. The liquid medium in which the microcapsules are dispersed is preferably aqueous (e.g., water). The dispersion may optionally, and/or preferably, be further formulated with additives as described elsewhere herein (e.g., a stabilizer, one or more surfactants, an antifreeze, an anti-packing agent, drift control agents, etc.).

The aqueous dispersion of microcapsules of the present invention may preferably be formulated to further optimize its shelf stability and safe use. Dispersants and thickeners are useful to inhibit the agglomeration and settling of the microcapsules. This function is facilitated by the chemical structure of these additives as well as by equalizing the densities of the aqueous and microcapsule phases. Anti-packing agents are useful when the microcapsules are to be redispersed. A pH buffer can be used to maintain the pH of the dispersion in a range which is safe for skin contact and, depending upon the additives selected, in a narrower pH range than may be required for the stability of the dispersion.

Low molecular weight dispersants may solubilize microcapsule shell walls, particularly in the early stages of their formation, causing gelling problems. Thus, in some embodiments dispersants having relatively high molecular weights of at least about 1.5 kg/mole, more preferably of at least about 3 kg/mole, and still more preferably at least about 5, 10 or even 15 kg/mole. In some embodiments, the molecular weight may range from about 5 kg/mole to about 50 kg/mole. Dispersants may also be non-ionic or anionic. An example of a high molecular weight, anionic polymeric dispersant is polymeric naphthalene sulfonate sodium salt, such as Invalon (formerly Irgasol, Huntsman Chemicals). Other useful dispersants are gelatin, casein, ammonium caseinate, polyvinyl alcohol, alkylated polyvinyl pyrrolidone polymers, maleic anhydride-methyl vinyl ether copolymers, styrene-maleic anhydride copolymers, maleic acid-butadiene and diisobutylene copolymers, sodium and calcium lignosulfonates, sulfonated naphthalene-formaldehyde condensates, modified starches, and modified cellulosics like hydroxyethyl or hydroxypropyl cellulose, and sodium carboxy methyl cellulose.

Thickeners are useful in retarding the settling process by increasing the viscosity of the aqueous phase. Shear-thinning thickeners may be preferred, because they act to reduce dispersion viscosity during pumping, which facilitates the economical application and even coverage of the dispersion to an agricultural field using the equipment commonly employed for such purpose. The viscosity of the microcapsule dispersion upon formulation may preferably range from about 100 cps to about 400 cps, as tested with a Haake Rotovisco Viscometer and measured at about 10° C. by a spindle rotating at about 45 rpm. More preferably, the viscosity may range from about 100 cps to about 300 cps. A few examples of useful shear-thinning thickeners include water-soluble, guar- or xanthan-based gums (e.g. Kelzan from CPKelco), cellulose ethers (e.g. ETHOCEL from Dow), modified cellulosics and polymers (e.g. Aqualon thickeners from Hercules), and microcrystalline cellulose anti-packing agents.

Adjusting the density of the aqueous phase to approach the mean weight per volume of the microcapsules also slows down the settling process. In addition to their primary purpose, many additives may increase the density of the aqueous phase. Further increase may be achieved by the addition of sodium chloride, glycol, urea, or other salts. The weight to volume ratio of microcapsules of preferred dimensions is approximated by the density of the core material, where the density of the core material is from about 1.05 to about 1.5 g/cm$^3$. Preferably, the density of the aqueous phase is formulated to within about 0.2 g/cm$^3$ of the mean weight to volume ratio of the microcapsules. More preferably, the density of the aqueous phase ranges from about 0.2 g/cm$^3$ less than the weight mean weight to volume ratio of the microcapsules to about equal to the weight mean weight to volume ratio of the microcapsules.

Surfactants can optionally be included in the formulated microcapsule dispersions of the present invention. Suitable surfactants are selected from non-ionics, cationics, anionics and mixtures thereof. Examples of surfactants suitable for the practice of the present invention include, but are not limited to: alkoxylated tertiary etheramines (such as TOMAH E-Series surfactants); alkoxylated quaternary etheramine (such as TOMAH Q-Series surfactant); alkoxylated etheramine oxides (such as TOMAH AO-Series surfactant); alkoxylated tertiary amine oxides (such as ARO-MOX series surfactants); alkoxylated tertiary amine surfactants (such as the ETHOMEEN T and C series surfactants); alkoxylated quaternary amines (such as the ETHOQUAD T and C series surfactants); alkyl sulfates, alkyl ether sulfates and alkyl aryl ether sulfates (such as the WITCOLATE series surfactants); alkyl sulfonates, alkyl ether sulfonates and alkyl aryl ether sulfonates (such as the WITCONATE series surfactants); alkoxylated phosphate esters and diesters (such as the PHOSPHOLAN series surfactants); alkyl polysaccharides (such as the AGRIMUL PG series surfactants); alkoxylated alcohols (such as the BRIJ or HETOXOL series surfactants); and mixtures thereof.

Anti-packing agents facilitate redispersion of microcapsules upon agitation of a formulation in which the microcapsules have settled. A microcrystalline cellulose material such as LATTICE from FMC is effective as an anti-packing agent. Other suitable anti-packing agents are, for example, clay, silicon dioxide, insoluble starch particles, and insoluble metal oxides (e.g. aluminum oxide or iron oxide). Anti-packing agents which change the pH of the dispersion are preferably avoided, for at least some embodiments.

Drift control agents suitable for the practice of the present invention are known to those skilled in the art and include the commercial products GARDIAN, GARDIAN PLUS, DRI-GARD, PRO-ONE XL ARRAY, COMPADRE, IN-PLACE, BRONC MAX EDT, EDT CONCENTRATE, COVERAGE and BRONC Plus Dry EDT.

The formulated microcapsule dispersions of the present invention are preferably easily redispersed, so as to avoid problems associated with application (e.g., clogging a spray tank). Dispersability may be measured by the Nessler tube test, wherein Nessler tubes are filled with 95 ml of water, then 5 ml of the test formulation is added by syringe. The tube is stoppered, and inverted ten times to mix. It is then placed in a rack, standing vertically, for 18 hours at 20° C. The tubes are removed and smoothly inverted every five seconds until the bottom of the tube is free of material. The number of inversions required to remix the settled material from the formulation is recorded. Preferably, the dispersions of the present invention are redispersed with less than about 100 inversions as measured by a Nessler tube test. More preferably, less than about 20 inversions are required for redispersion.

The pH of the formulated microcapsule dispersion may preferably range from about 4 to about 9, in order to minimize eye irritation of those persons who may come into contact with the formulation in the course of handling or application to crops. However, if components of a formulated dispersion are sensitive to pH, such as for example the blocking agent, buffers such as disodium phosphate may be used to hold the pH in a range within which the components are most effective. Additionally, a pH buffer such as citric acid monohydrate may be particularly useful in some systems during the preparation of microcapsules, to maximize the effectiveness of a protective colloid such as SOKALAN CP9.

Other useful additives include, for example, biocides or preservatives (e.g., Proxel, commercially available from Avecia), antifreeze agents (such as glycerol, sorbitol, or urea), and antifoam agents (such as Antifoam SE23 from Wacker Silicones Corp.).

Controlling Plant Growth With Microcapsule Dispersions

The microcapsule dispersions disclosed herein are useful as controlled-release herbicides or concentrates thereof. Therefore, the present invention is also directed to a method of applying a dispersion of the microencapsulated herbicides for controlling plant growth. In some embodiments, herein, the dispersion of herbicidal microcapsules is applied to the ground, over the tops of the crop plants (i.e., onto the foliage), or a combination thereof.

A microcapsule dispersion may be applied to plants, e.g. crops in a field, according to practices known to those skilled in the art. The microcapsules are preferably applied as a controlled release delivery system for an agricultural chemical (e.g., acetanilide herbicide) or blend of agricultural chemicals contained therein. Because the mean release characteristics of a population of microcapsules of the present invention are adjustable, the timing of release initiation (or increase release) can be controlled thereby giving both commercially acceptable weed control and a commercially acceptable rate of crop injury.

When blended for end use on an agricultural field, the dispersion of herbicide-containing microcapsules prior to dilution by the end user may be, for example, less than about 62.5 weight percent microcapsules, or alternatively, less than about 55 weight percent herbicide or other active. If the dispersion is too concentrated with respect to microcapsules, the viscosity of the dispersion may be too high to pump and also may be too high to easily redisperse if settling has occurred during storage. It is for these reasons that the dispersion preferably has a viscosity of less than about 400 cps, as describe above.

The microcapsule dispersions may be as dilute with respect to microcapsule weight percent as is preferred by the user, constrained mainly by the economics of storing and transporting the additional water for dilution and by possible adjustment of the additive package to maintain a stable dispersion. Typically, the dispersion is at least about 25 weight percent herbicidal active (about 30 weight percent microcapsules) for these reasons. These concentrations are useful compositions for the storage and transport of the dispersions.

For a stand-alone (i.e., in the absence of a co-herbicide) application of the microcapsules of the present invention, the dispersion is preferably diluted with water to form an application mixture prior to application to a field of crop plants. Typically, no additional additives are required to place the dispersion in a useful condition for application as a result of dilution. The optimal concentration of a diluted dispersion is dependent in part on the method and equipment which is used to apply the herbicide.

The effective amount of microcapsules to be applied to an agricultural field is dependent upon the identity of the encapsulated herbicide, the release rate of the microcapsules, the crop to be treated, and environmental conditions, especially soil type and moisture. Generally, application rates of herbicides, such as, for example, acetochlor, are on the order of about 1 kilogram of herbicide per hectare. But, the amount may vary by an order of magnitude or more in some instances, i.e., from 0.1 to 10 kilograms per hectare.

Application mixtures of the dispersions of the microencapsulated acetamide herbicides are preferably applied to an agricultural field within a selected timeframe of crop plant development. In one embodiment of the present invention, the dispersion of the microencapsulated herbicides is preferably applied to the crop plant after emergence (including cracking) and up to and including the six leaf stage and before emergence of the weeds.

Application mixtures of the aqueous dispersions of herbicidal microcapsules of the present invention are useful for controlling a wide variety of weeds, i.e., plants that are considered to be a nuisance or a competitor of commercially important crop plants, such as corn, soybean, cotton, etc. In some embodiments, the microcapsules of the present invention are applied before the weeds emerge (i.e., pre-emergence application). Examples of weeds that may be controlled according to the method of the present invention include, but are not limited to, Meadow Foxtail (*Alopecurus pratensis*) and other weed species with the *Alopecurus* genus, Common Barnyard Grass (*Echinochloa crus-galli*) and other weed species within the *Echinochloa* genus, crabgrasses within the genus *Digitaria*, White Clover (*Trifolium repens*), Lambsquarters (*Chenopodium berlandieri*), Redroot Pigweed (*Amaranthus retroflexus*) and other weed species within the *Amaranthus* genus, Common Purslane (*Portulaca oleracea*) and other weed species in the *Portulaca* genus, *Chenopodium album* and other *Chenopodium* spp., *Setaria lutescens* and other *Setaria* spp., *Solanum nigrum* and other *Solanum* spp., *Lolium multiflorum* and other *Lolium* spp., *Brachiaria platyphylla* and other *Brachiaria* spp., *Sorghum halepense* and other *Sorghum* spp., *Conyza Canadensis* and other *Conyza* spp., and *Eleusine indica*. In some embodiments, the weeds comprise one or more glyphosate resistant species, 2,4-D resistant species, dicamba resistant species and/or ALS inhibitor herbicide resistant species. In some embodiments, the glyphosate-resistant weed species is selected from the group consisting of *Amaranthus palmeri, Amaranthus rudis, Ambrosia artemisiifolia, Ambrosia trifida, Conyza bonariensis, Conyza canadensis, Digitaria insularis, Echinochloa colona, Eleusine indica, Euphorbia heterophylla, Lolium multiflorum, Lolium rigidum, Plantago Ianceolata, Sorghum halepense*, and *Urochloa panicoides*.

As used herein transgenic glyphosate-tolerant corn, soybean, cotton, etc. plants includes plants grown from the seed of any corn, soybean, cotton, etc. event that provides glyphosate tolerance and glyphosate-tolerant progeny thereof.

Such glyphosate-tolerant events include, without limitation, those that confer glyphosate tolerance by the insertion or introduction, into the genome of the plant, the capacity to express various native and variant plant or bacterial EPSPS enzymes by any genetic engineering means known in the art for introducing transforming DNA segments into plants to confer glyphosate resistance as well as glyphosate-tolerant cotton events that confer glyphosate tolerance by other means such as described in U.S. Pat. Nos. 5,463,175 and 6,448,476 and International Publication Nos. WO 2002/36782, WO 2003/092360 and WO 2005/012515.

Non-limiting examples of transgenic glyphosate-tolerant cotton events include the glyphosate-tolerant (ROUNDUP READY) cotton event designated 1445 and described in U.S. Pat. No. 6,740,488. Of particular interest in the practice of the present invention are methods for weed control in a crop of transgenic glyphosate-tolerant cotton plants in which glyphosate resistance is conferred in a manner that allows later stage application of glyphosate herbicides without incurring significant glyphosate-mediated reproductive injury. Non-limiting examples of such transgenic glyphosate-tolerant cotton plants include those grown from the seed of the glyphosate-tolerant (ROUNDUP READY) FLEX cotton event (designated MON 88913 and having representative seed deposited with American Type Culture Collection (ATCC) with Accession No. PTA-4854) and similar glyphosate-tolerant cotton events and progeny thereof as described in International Publication No. WO 2004/072235. Glyphosate-tolerant (ROUNDUP READY FLEX) cotton event MON 88913 and similar glyphosate-tolerant cotton events may be characterized in that the genome comprises one or more DNA molecules selected from the group consisting of SEQ ID NO:1, SEQ ID NO:2, SEQ ID NO:3, and SEQ ID NO:4; or the genome in a DNA amplification method produces an amplicon comprising SEQ ID NO:1 or SEQ ID NO:2; or the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2 as described in International Publication No. WO 2004/072235, the entire contents of which are incorporated herein by reference. A sequence listing containing each of SEQ ID NOS: 1, 2, 3, and 4 as disclosed in International Publication No. WO 2004/072235 is contained herein. These sequences are listed as SEQ ID NOS: 1, 2, 3, and 4, respectively.

As noted above, the glyphosate-tolerant (ROUNDUP READY FLEX) cotton event MON 88913 allows for over-the-top application of glyphosate herbicides at advanced stages of plant development without incurring significant glyphosate-mediated reproductive injury (e.g., as quantified, for example, by flower pollen shed and/or lint yield). As compared to the previous commercial glyphosate-tolerant (ROUNDUP READY) cotton event designated 1445, glyphosate-tolerant (ROUNDUP READY FLEX) cotton event MON 88913 is particularly advantageous in allowing foliar application of glyphosate herbicide for weed control at a developmental age characterized by at least five leaf nodes present on a cotton plant of the crop. As used herein, a node having a leaf branch is referred to as a leaf node in accordance with the conventional node method used in assessing cotton plant developmental age. Furthermore, cotyledons are leaves originally contained in the seed and are not considered as plant leaves or nodes for purposes of determination of the stage of cotton development. That is, as generally accepted by those skilled in the art and as used herein, the stem point of cotyledon attachment is referenced as Node 0. The fifth and subsequent leaf nodes are typically the first reproductive (i.e., fruiting) branches and may develop a fruiting bud and associated leaf. A leaf node having a reproductive branch may be referred as a reproductive node. Cotton plants can develop as many as about 25 leaf nodes, with nodes 5-25 potentially developing into reproductive nodes. In practicing weed control in a crop of transgenic glyphosate-tolerant cotton grown from seed of glyphosate-tolerant (ROUNDUP READY FLEX) cotton event MON 88913 or similar cotton events and progeny thereof, glyphosate herbicidal formulations can be applied over-the-top of the crop at more advanced developmental ages characterized, for example, by six, ten, twelve, fourteen or more leaf nodes present on a cotton plant of the crop and up to and including layby without incurring significant glyphosate-mediated reproductive injury to the crop. Herbicidal glyphosate formulation may be applied over-the-top of the cotton crop at various intervals of advanced development, characterized, for example, by six or more leaf nodes and no more than ten, twelve, fourteen, sixteen, eighteen, twenty or twenty-five leaf nodes on a cotton plant of the crop.

In some embodiments as described previously, the herbicidal microcapsules of the present invention can be dispersed in combination with one or more co-herbicides in an aqueous concentrate or spray application tank mix, such as a co-herbicide selected from acetyl CoA carboxylase inhibitors (such as aryloxyphenoxypropionics), organophosphorus herbicides, auxins (e.g., synthetic auxins), photosystem II inhibitors (such as ureas and triazines), ALS inhibitors (such as sulfonyl ureas, triazolopyrimidines and imidazolinones), protoporphyrinogen oxidase inhibitors (such as diphenyl ethers, phenyl pyrazoles, aryl triazones and oxadiazoles) and carotenoid biosynthesis inhibitors (such as isoxazolidinones, benzoylcyclohexanediones, benzoylpyrazoles), salts and esters thereof, and mixtures thereof. Application mixtures of the co-herbicide formulations can likewise be prepared. A weight ratio of acetamide to co-herbicide of from 10:1 to 1:10 or from 5:1 to 1:5 is preferred.

Where an herbicide is referenced generically herein by name, unless otherwise restricted, that herbicide includes all commercially available forms known in the art such as salts, esters, free acids and free bases, as well as stereoisomers thereof. For example, where the herbicide name "glyphosate" is used, glyphosate acid, salts and esters are within the scope thereof.

Organophosphorus herbicides include, for example, glyphosate, glufosinate, glufosinate-P, salts and esters thereof, and mixtures thereof.

Acetyl CoA carboxylase inhibitors include, for example, alloxydim, butroxydim, clethodim, cycloxydim, pinoxaden, sethoxydim, tepraloxydim and tralkoxydim, salts and esters thereof, and mixtures thereof. Another group of acetyl CoA carboxylase inhibitors include chlorazifop, clodinafop, clofop, cyhalofop, diclofop, diclofop-methyl, fenoxaprop, fenthiaprop, fluazifop, haloxyfop, isoxapyrifop, metamifop, propaquizafop, quizalofop and trifop, salts and esters thereof, and mixtures thereof. Acetyl CoA carboxylase inhibitors also include mixtures of one or more "dims" and one or more "fops", salts and esters thereof.

Auxin herbicides include, for example, 2,4-D, 2,4-DB, dichloroprop, MCPA, MCPB, aminopyralid, clopyralid, fluroxypyr, triclopyr, diclopyr, mecoprop, dicamba, picloram and quinclorac, salts and esters thereof, and mixtures thereof.

Photosystem II inhibitors include, for example, ametryn, amicarbazone, atrazine, bentazon, bromacil, bromoxynil, chlorotoluron, cyanazine, desmedipham, desmetryn, dimefuron, diruon, fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof.

ALS inhibitors include, for example, amidosulfuron, azimsulfruon, bensulfuron-methyl, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florazulam, flucarbazone, flucetosulfuron, flumetsulam, flupyrsulfuron-methyl, foramsulfuron, halosulfuron-methyl, imazamethabenz, imazamox, imazapic, imazapyr, imazaquin, imazethapyr, imazosulfuron, iodosulfuron, metsulfuron-methyl, nicosulfuron, penoxsulam, primisulfuron-methyl, propoxycarbazone-sodium, prosulfuron, pyrazosulfuron-ethyl, pyribenzoxim, pyrithiobac, rimsulfuron, sulfometuron-methyl, sulfosulfuron, thifensulfuron-methyl, triasulfuron, tribenuron-methyl, trifloxysulfuron and triflusulfuron-methyl, salts and esters thereof, and mixtures thereof.

Protoporphyrinogen oxidase inhibitors include, for example, acifluorfen, azafenidin, bifenox, butafenacil, carfentrazone-ethyl, flufenpyr-ethyl, flumiclorac, flumiclorac-pentyl, flumioxazin, fluoroglycofen, fluthiacet-methyl, fomesafen, lactofen, oxadiargyl, oxadiazon, oxyfluorfen, pyraflufen-ethyl and sulfentrazone, salts and esters thereof, and mixtures thereof.

Carotenoid biosynthesis inhibitors include, for example, aclonifen, amitrole, beflubutamid, benzofenap, clomazone, diflufenican, fluridone, flurochloridone, flurtamone, isoxaflutole, mesotrione, norflurazon, picolinafen, pyrazolynate, pyrazoxyfen, sulcotrione and topramezone, salts and esters thereof, and mixtures thereof.

In some embodiments the herbicidal microcapsules of the present invention can be dispersed with two co-herbicides to form a three-way herbicidal composition. The compositions can be concentrate compositions or application mixtures. A weight ratio of acetamide to total co-herbicide of from 10:1 to 1:10 or from 5:1 to 1:5 is preferred. In some embodiments, the encapsulated acetamides are combined in an aqueous application mixture with an auxin herbicide and an organophosphate herbicide, or salts or esters thereof. In some embodiments, the encapsulated acetamide herbicide is selected from acetochlor, metolachlor, S-metolachlor, dimethenamide and dimethenamide-P salts and esters thereof, the first co-herbicide is selected from dicamba and 2,4-D, salts and esters thereof, and the second co-herbicide is selected from glyphosate, glufosinate and glufosinate-P, salts and esters thereof. Examples include: encapsulated acetochlor, dicamba and glyphosate; encapsulated metolachlor and/or S-metolachlor, dicamba and glyphosate; encapsulated dimethenamid and/or dimethenamid-P, dicamba and glyphosate; encapsulated acetochlor, 2,4-D and glyphosate; encapsulated metolachlor and/or S-metolachlor, 2,4-D and glyphosate; encapsulated dimethenamid and/or dimethenamid-P, 2,4-D and glyphosate; encapsulated acetochlor, dicamba and glufosinate and/or glufosinate-P; encapsulated metolachlor and/or S-metolachlor, dicamba and glufosinate and/or glufosinate-P; encapsulated dimethenamid and/or dimethenamid-P, dicamba and glufosinate and/or glufosinate-P; encapsulated acetochlor, 2,4-D and glufosinate and/or glufosinate-P; encapsulated metolachlor and/or S-metolachlor, 2,4-D and glufosinate and/or glufosinate-P; and encapsulated dimethenamid and/or dimethenamid-P, 2,4-D and glufosinate and/or glufosinate-P.

In a preferred embodiment, the present microcapsules are used in the preparation of an aqueous concentrate composition or tank mix comprising glyphosate or a salt thereof (e.g., the potassium or monoethanolammonium salt). In such a tank mix, a percent by weight acetamide from about 3% to about 0.25% a.e. and from about 3% by weight to about 0.25% a.e. by weight is preferred. Such an aqueous composition is particularly useful for use over glyphosate-tolerant crop plants to control glyphosate susceptible plants and several commercially important weeds that have been reported to be glyphosate resistant, including, for example, palmer amaranth (*Amaranthus palmeri*), waterhemp (*Amaranthus rudis*), common ragweed (*Ambrosia artemisiifolia*), giant ragweed (*Ambrosia trifida*), hairy fleaane (*Conyza bonariensis*), horseweed (*Conyza canadensis*), sourgrass (*Digitaria insularis*), junglerice (*Echinochloa colona*), goosegrass (*Eleusine indica*), wild poinsettia (*Euphorbia heterophylla*), Italian ryegrass (*Lolium multiflorum*), rigid ryegrass (*Lolium rigidum*), buckhorn plantain (*Plantago lanceolata*), Johnsongrass (*Sorghum halepense*), and liverseedgrass (*Urochloa panicoides*).

As used throughout this specification, the expression "predominantly comprises" means more than 50%, preferably at least about 75%, and more preferably at least about 90% by weight of the component is made up of the specified compound(s).

Having described the invention in detail, it will be apparent that modifications and variations are possible without departing from the scope of the invention defined in the appended claims.

EXAMPLES

The following non-limiting Examples are provided to further illustrate the present invention. In each of the Examples, the materials shown in the following Table were used. Throughout the Examples, these components are referred to by the term stated in the Reference column.

| Material | Function | Reference | Supplier |
| --- | --- | --- | --- |
| Acetochlor | Herbicide | Acetochlor | Monsanto |
| Furilazole | Safener | | Monsanto |
| n-Pentadecane | Internal Phase Solvent (dilutent) | NORPAR 15 | Exxon Mobil |
| Isoparaffinic hydrocarbon (approximate MW 234) | Internal Phase Solvent (dilutent) | ISOPAR V | Exxon Mobil |
| Isoparaffinic hydrocarbon (approximate MW 163) | Internal Phase Solvent (dilutent) | ISOPAR L | Exxon Mobil |
| Dearomatized hydrocarbon | Internal Phase Solvent | EXXSOL D-130 | Exxon Mobil |

-continued

| Material | Function | Reference | Supplier |
|---|---|---|---|
| (approximate MW 229) | (dilutent) | | |
| Dearomatized hydrocarbon (approximate MW 200) | Internal Phase Solvent (dilutent) | EXXSOL D-110 | Exxon Mobil |
| Triethylenetetramine 50% solution | Amine shell wall component | TETA | Huntsman Chemical |
| Meta-Xylylenediamine 50% solution | Amine shell wall component | XDA | |
| Desmodur N3200 Trimer of hexamethylene-1,6-diisocyanate | Triisocyanate shell wall component | DES N3200 | Bayer |
| Desmodur W 4,4'-diisocyanato-dicyclohexyl methane | Diisocyanate shell wall component | DES W | Bayer |
| 85% by weight trimer of hexamethylene-1,6-diisocyanate:15% by weight 4,4'-diisocyanato-dicyclohexyl methane | Blend of DES N3200 and DES W | MISTAFLEX | Monsanto |
| Water | External Phase Solvent | Water | |
| Ammonium caseinate | Dispersant | Ammonium caseinate | American Casein Company |
| Glycerin | | Glycerin | Cargill |
| Maleic acid-olefin copolymer, 25% solution | surfactant | SOKALAN CP9 | BASF |
| Citric Acid, 50% solution | pH adjustment | Acid | ADM |
| Invalon DAM Naphthalene formaldehyde condensate sulfonate | Dispersant | Invalon | Huntsman Chemical |
| Kelzan CC | Thickener | Kelzan CC | Kelco |
| Proxel GXL | Preservative | Proxel GXL | Avecia |
| NAOH, 20% solution | pH adjustment | Caustic | Dow Chemical |
| Antifoam SE23 | Antifoam | Antifoam | Wacker Silicone |
| $Na_2HPO_4$ | Buffer | Buffer | ICL Performance Products |

The herbicidal effectiveness data set forth herein report crop damage and weed inhibition as a phytotoxicity percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial.

The selection of application rates that are biologically effective for a specific acetamide herbicide is within the skill of the ordinary agricultural scientist. Those of skill in the art will likewise recognize that individual plant conditions, weather and growing conditions, as well as the specific exogenous chemical and formulation thereof selected, will affect the efficacy on weeds and associated crop injury achieved in practicing this invention. Useful application rates for the acetamide herbicides employed can depend upon all of the above factors. With respect to the use of the method of this invention, much information is known about appropriate acetamide application rates. Over four decades of acetamide use and published studies relating to such use have provided abundant information from which a weed control practitioner can select acetamide application rates that are herbicidally effective on particular species at particular growth stages in particular environmental conditions.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition, at the time of application to plants, is preferably dilute enough to be readily sprayed using standard agricultural spray equipment. Preferred application rates for the present invention vary depending upon a number of factors, including the type and concentration of active ingredient and the plant species involved. Selection of appropriate rates of application is within the capability of one skilled in the art. Useful rates for applying an aqueous application mixture to a field of foliage can range from about 50 to about 1,000 liters per hectare (L/ha) by spray application. The preferred application rates for aqueous application mixtures are in the range from about 100 to about 300 L/ha.

Damage to the foliage of a crop plant may cause the plant to be stunted or otherwise reduce the yield of the desired agricultural commodity. Thus, it is important that a herbicidal composition not be applied in such a manner as to excessively injure and interrupt the normal functioning of the plant tissue. However, some limited degree of local injury can be insignificant and commercially acceptable.

A large number of compositions of the invention are illustrated in the examples that follow. Many concentrate acetamide compositions have provided sufficient herbicidal effectiveness in greenhouse tests to warrant field testing on a wide variety of weed species under a variety of application conditions.

The experiments were carried out in a greenhouse. The herbicidal compositions were applied post-emergence to crops on or before the 2-6-leaf stage using a research track sprayer. Test compositions were applied at a spray volume 94 L/ha applied by means compressed air at a pressure of 165 kpa. The dilution of the dispersion of herbicidal microcapsules were varied in order achieve different concentrations of active applied. Weed control testing was accomplished by applying the herbicidal compositions to the soil prior to weed emergence. Three days after application, the samples were irrigated with 0.125 inches of overhead irrigation and sub-irrigated as needed throughout the study.

Example 1

Preparation of Aqueous Dispersions of Microencapsulated Acetochlor

Aqueous dispersions of microencapsulated acetochlor were prepared according to the protocol described in this example. The aqueous dispersions were prepared using a method that resulted in microcapsules having a mean diameter greater than those found in DEGREE, a commercially available microencapsulated herbicidal product containing about 42% by weight acetochlor, available from Monsanto Company. The microcapsules in DEGREE have a mean diameter of about 2.5 µm. The test formulations resulted in aqueous dispersions of microcapsules having mean diameters significantly greater, such as about 5 µm to about 13 µm. Field studies indicated that the aqueous dispersions of herbicidal microcapsules having larger mean diameters exhibited improved crop safety when tested on soybean and cotton compared to DEGREE and also compared to HARNESS, a commercially available herbicidal product containing emulsified concentrate of unencapsulated acetochlor, also available from Monsanto Company.

The internal phases were prepared to contain the components and amounts shown in the following table. The percentages indicate the approximate weight percentage of each component in the aqueous dispersion.

TABLE

Internal Phase Components

| Form. | Acetochlor | | NORPAR 15 | | MISTAFLEX | |
|---|---|---|---|---|---|---|
| | (g) | (%) | (g) | (%) | (g) | (%) |
| 5291 | 447.25 | 43.19 | 23.56 | 2.35 | 30.84 | 3.07 |
| 5297 | 894.21 | 43.19 | 46.99 | 2.35 | 61.53 | 3.07 |
| 5295 | 841.2 | 40.63 | 107.01 | 5.00 | 61.73 | 3.07 |

To prepare the internal phase of formulations 5291, 5297, and 5295, acetochlor was charged to the mixing vessels in the amounts shown in the above internal phase components table. Next, NORPAR 15 was charged to the mixing vessels, followed by the MISTAFLEX blend of DES N3200 and DES W polyisocyanates. The solution was agitated to obtain a clear homogenous solution. The solution may be sealed within the mixing vessel and stored until needed. Prior to use, the mixture was heated to 50° C. in an oven.

The external aqueous phases were prepared containing the components and amounts shown in the following table:

TABLE

External Phase Components

Weight of Components in grams

| Form. | Water | Ammonium Caseinate | Glycerin | SOKALAN CP9 | Acid |
|---|---|---|---|---|---|
| 5291 | 278.2 | 0.45 | 81.1 | 23.0 | 1.64 |
| 5297 | 556.61 | 0.98 | 162.28 | 46.04 | 3.09 |
| 5295 | 556.32 | 0.93 | 162.27 | 46.63 | 3.23 |

To prepare the external phase of formulations 5291, 5297, and 5295, mixing vessels were charged with water in the amounts shown in the above external phase components table, and the remaining components were added in the order shown in the above table. The solution was agitated to obtain a clear homogenous solution. The solution may be sealed within the mixing vessel and stored until needed. Prior to use, the mixture was heated to 50° C. in an oven.

The interfacial polymerization medium was prepared by first charging the external phase to a Waring blender cup that has been preheated to 50° C. The commercial Waring blender (Waring Products Division, Dynamics Corporation of America, New Hartford, Conn., Blender 700) was powered through a 0 to 120 volt variable autotransformer. The blender mix speed was varied by controlling power to the blender as shown below in the emulsification parameters table. The internal phase was added to the external phase over a 16 second interval and blending was continued to obtain an emulsion.

TABLE

Emulsification Parameters

| Form. | Voltage (V) | Power (%) | Duration (s) |
|---|---|---|---|
| 5297 | 120 | 40 | 120 |
| 5295 | 120 | 40 | — |

To initiate polymerization and encapsulation of the internal phase, a 50% by weight solution of TETA was added to the emulsion to the amounts shown in the following Amine Table over a period of about 5 seconds. The blender speed is then reduced to a speed which just produces a vortex for approximately five to fifteen minutes. The emulsion was then transferred to a hot plate and stirred. The reaction vessel is covered and maintained at about 50° C. for approximately two hours which has been found is sufficient time for the isocyanate to react essentially completely.

TABLE

Amine

| | TETA, 50% by weight solution | |
|---|---|---|
| Form. | (g) | (%) |
| 5291 | 14.14 | 1.39% |
| 5297 | 27.72 | 1.39% |
| 5295 | 27.92 | 1.39% |

The capsule slurry is then allowed to cool to close to room temperature. The components shown in the stabilizer components table with the exception of the buffer are previously premixed with a high speed mixer (Waring Blender or Cowles Dissolver). The resulting stabilizer premix is then added to the capsule slurry to stabilize the dispersion of microcapsules. Finally the buffer is added and the mixture is stirred for at least 15 minutes until visually homogeneous.

Due to variations in the blender design and other uncontrollable variables, it was found to be difficult to correlate blender speed and particle size accurately. In consequence, some samples were discarded because they did not have the desired size. Samples were chosen for evaluation based on their measured particle size.

TABLE

Stabilizer Components

Weight of Components in grams

| Form. | Invalon | Glycerin | Kelzan CC |
|---|---|---|---|
| 5291 | 58.41 | 39.2 | 0.53 |
| 5297 | 116.83 | 78.37 | 1.04 |
| 5295 | 116.83 | 78.37 | 1.04 |

TABLE-continued

Stabilizer Components

| Form. | Proxel GXL | Caustic | Antifoam | Buffer |
|---|---|---|---|---|
| 5291 | 0.53 | 0.23 | 0.01 | 1.18 |
| 5297 | 1.04 | 0.354 | 0.01 | 2.38 |
| 5295 | 1.04 | 0.354 | 0.01 | 2.38 |

Formulations 5291, 5297, and 5295 were stabilized aqueous dispersions of microcapsules containing acetochlor at an approximate active concentration of 42.5% AI by weight (which approximately the same active concentration as DEGREE).

Each formulation was prepared to have an excess molar equivalents ratios of amine molar equivalents to isocyanate molar equivalents and herbicide to shell wall component ratios. TETA has an approximate equivalent weight of 36.6 g/mol. DES N3200 has an approximate equivalent weight of 183 g/mol (theoretical equivalent weight is 159.53 g/mol). DES W has an approximate equivalent weight of 132 g/mol. Formulation 5295 was prepared with an excess of internal phase solvent (diluent), NORPAR 15. The formulations had the following weight ratios:

TABLE

Formulation Characteristics

| Form. | Molar equivalents ratio | Ratio of Herbicide to Shell Wall Components | Ratio of Herbicide to Internal Phase Solvent |
|---|---|---|---|
| 5291 | 1.08:1 | 9.94:1 | 18.98:1 |
| 5297 | 1.06:1 | 10.02:1 | 19.03:1 |
| 5295 | 1.06:1 | 9.38:1 | 7.86:1 |

The blender speed was controlled to produce an increased microcapsule size compared to the microcapsules in DEGREE, which is about 2.5 μm. The mean particle sizes and standard deviations of the microcapsules in the slurry for each formulation are shown in the following table:

TABLE

Particle Size Parameters

| Form. | Mean Particle size (μm) | Standard Deviation (μm) |
|---|---|---|
| 5291 | 5.57 | 3.99 |
| 5297 | 13.97 | 8.5 |
| 5295 | 12.70 | 7.85 |

The particle size parameters were measured using a Beckman Coulter LS Particle Size Analyzer.

Example 2

Figure 2:
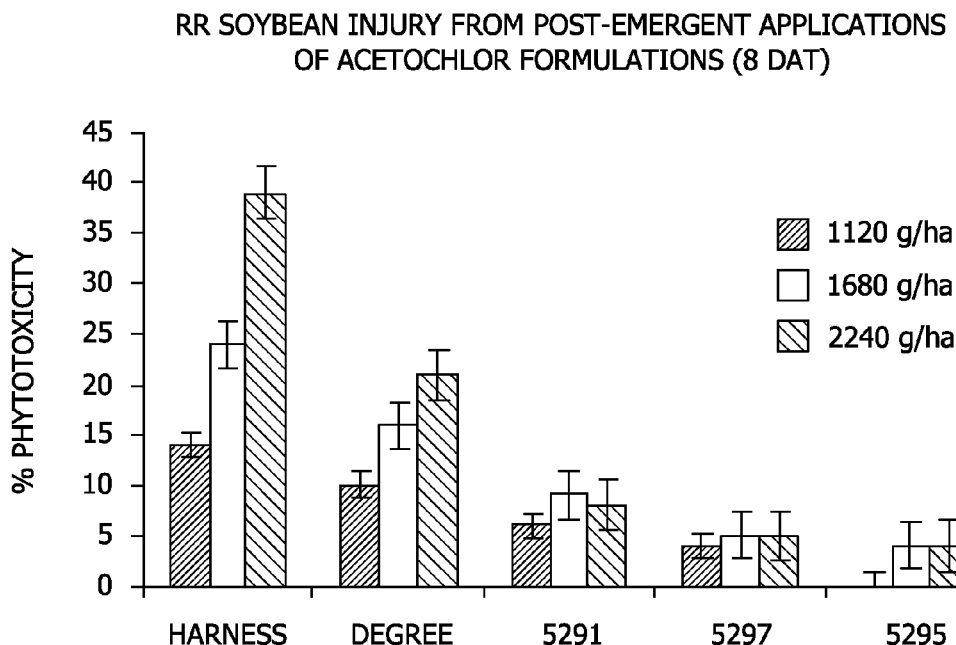
FIG. 2 is a graph depicting soybean injury that occurred with post-emergent applications of various microencapsulated acetochlor formulations as described in Example 2.
Figure 3:
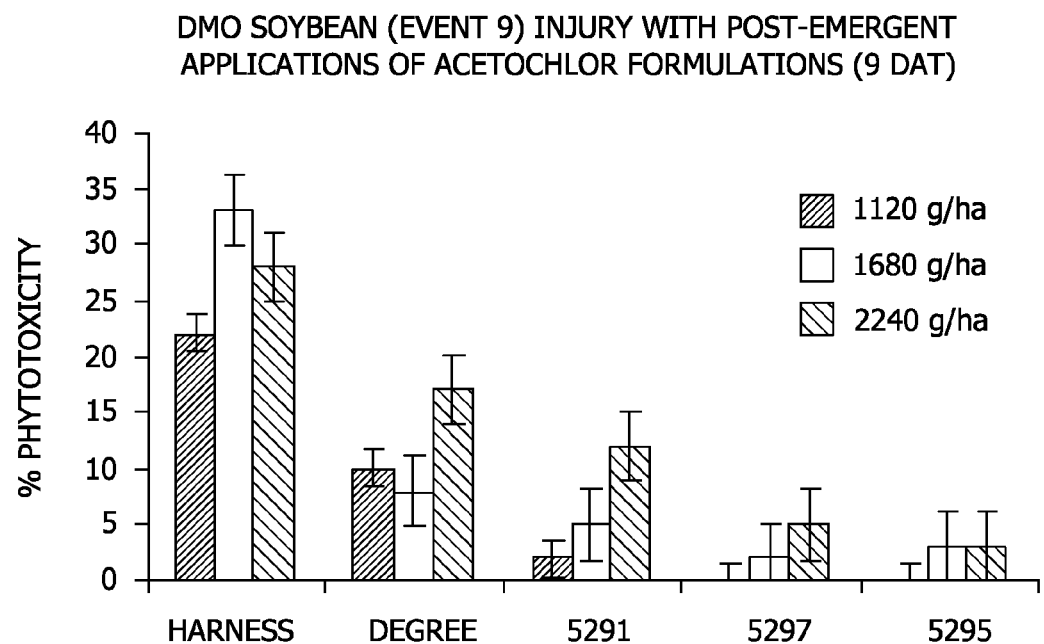
FIG. 3 is a graph depicting soybean injury that occurred with post-emergent applications of various microencapsulated acetochlor formulations as described in Example 2.
Figure 4:
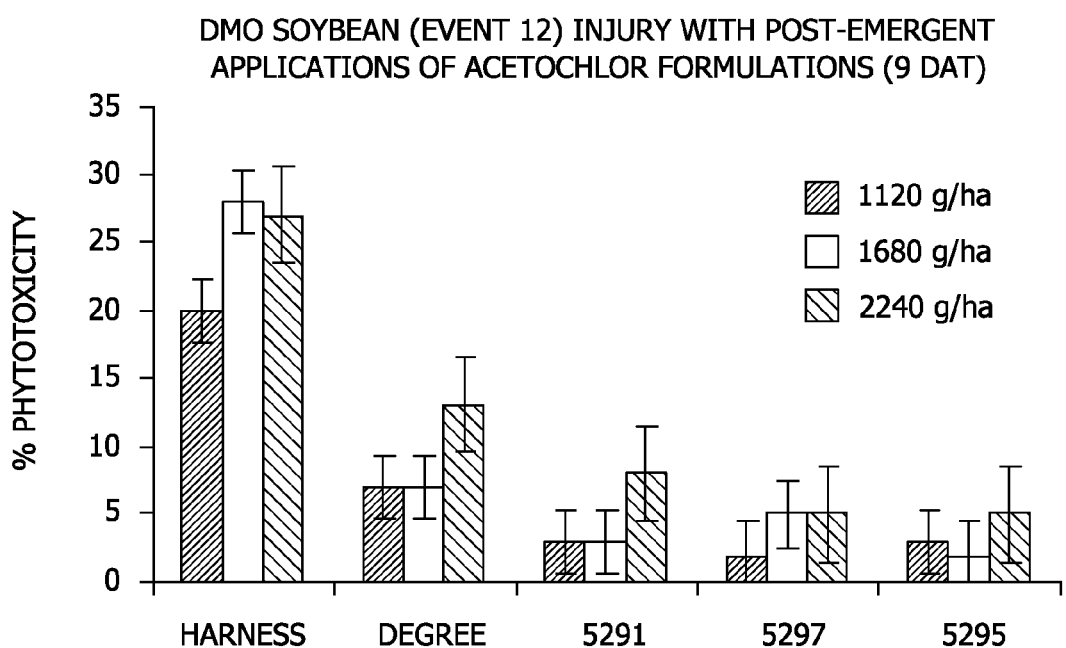
FIG. 4 is a graph depicting soybean injury that occurred with post-emergent applications of various microencapsulated acetochlor formulations as described in Example 2.
Figure 5:
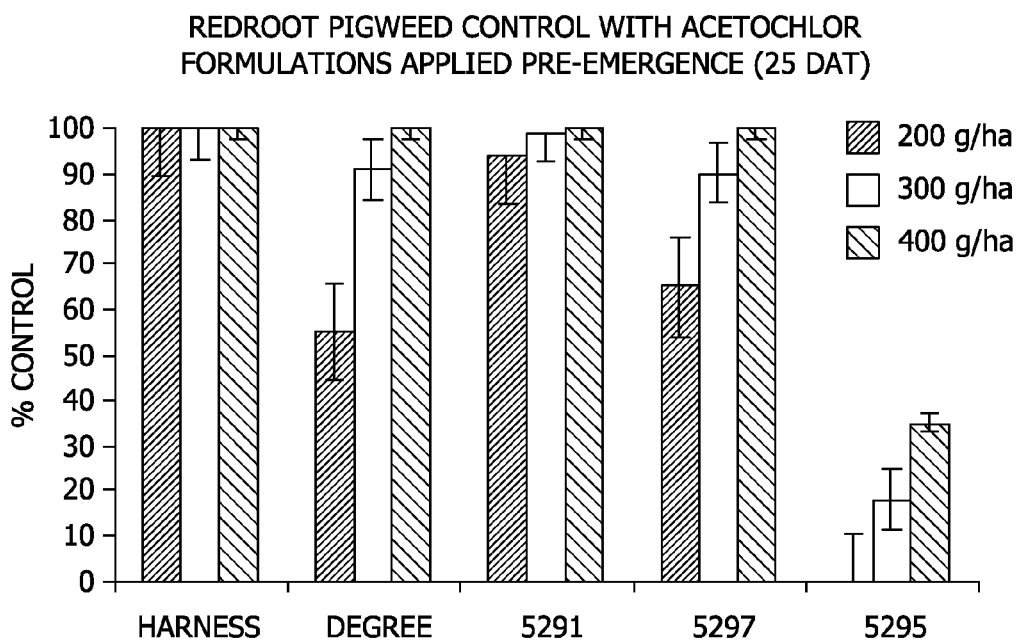
FIG. 5 is a graph depicting control of redroot pigweed achieved with pre-emergent applications of various microencapsulated acetochlor formulations as described in Example 2.
Figure 6:
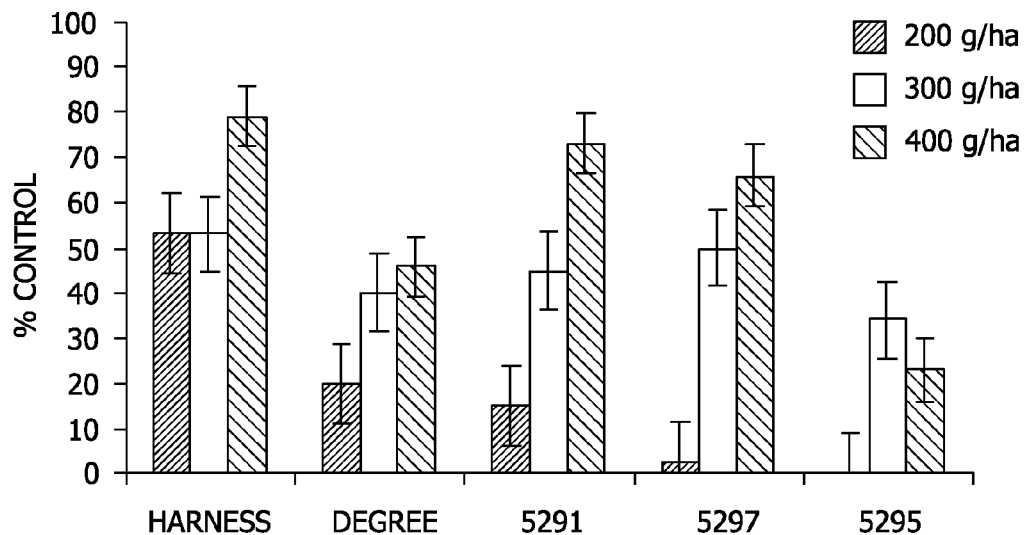
FIG. 6 is a graph depicting control of common lambsquarters control achieved with pre-emergent applications of various microencapsulated acetochlor formulations as described in Example 2.
Figure 7:
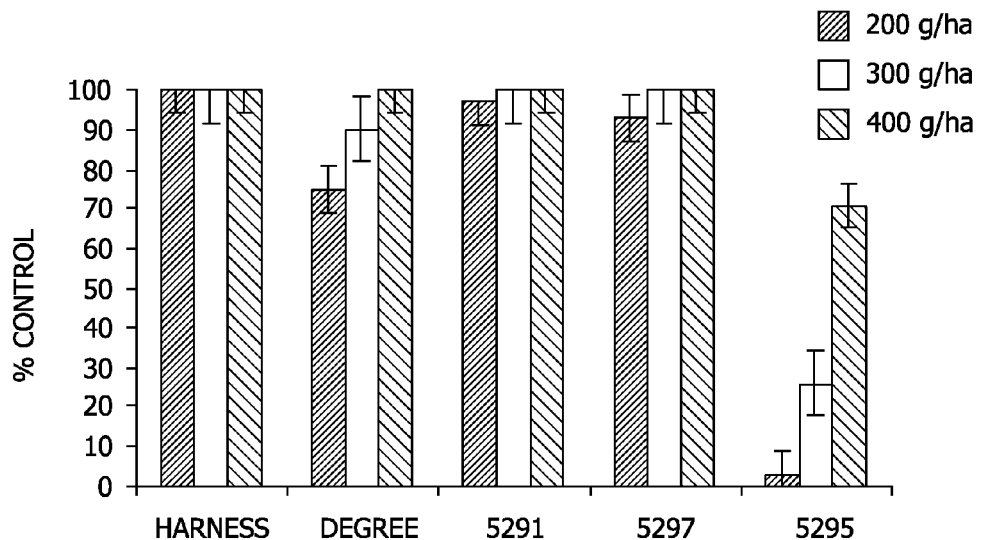
FIG. 7 is a graph depicting control of barnyard grass achieved with pre-emergent applications of various microencapsulated acetochlor formulations as described in Example 2.
Figure 8:
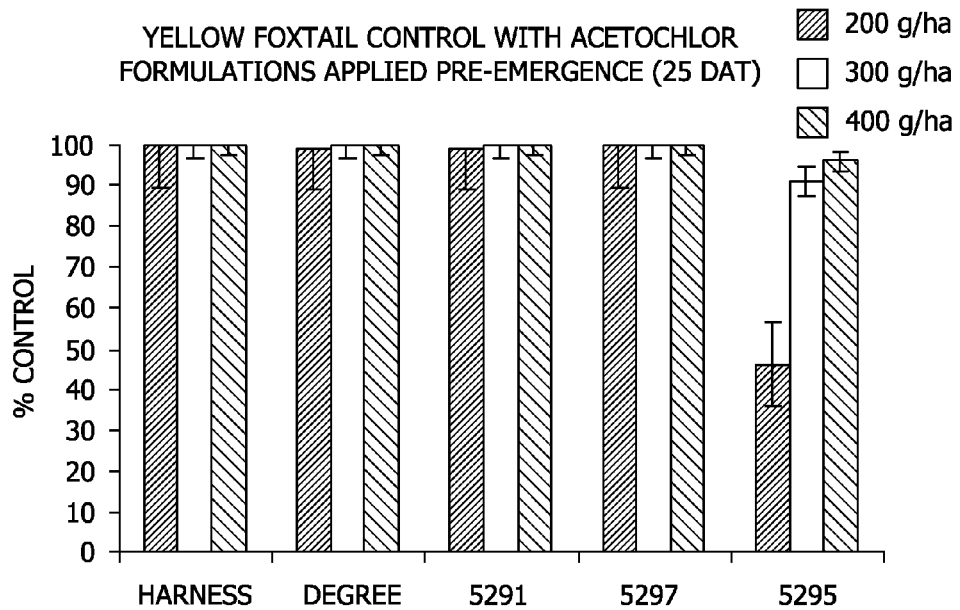
FIG. 8 is a graph depicting control of yellow foxtail achieved with pre-emergent applications of various microencapsulated acetochlor formulations as described in Example 2.

Study of Soybean and Cotton Crop Safety and Post-emergence Weed Control Efficacy Using Microencapsulated Acetochlor Formulations of the Invention Formulations 5291, 5297, and 5295 (prepared according to the method described above in Example 1) were applied to glyphosate-tolerant (ROUNDUP READY) soybean and dicamba-tolerant soybeans and glyphosate-tolerant (ROUNDUP READY) cotton (RR Flex—short to mid-season variety) crops under greenhouse conditions. These formulations were tested against commercial acetochlor formulations HARNESS and DEGREE. The formulations were applied to post-emergent soybean and cotton plants and measured for phytotoxicity at 7, 8, and 9 days after treatment ("DAT"). The results are shown in FIG. 1 (Cotton injury 7 DAT), FIG. 2 (Soybean injury at 8 DAT), FIG. 3 (Soybean injury at 9 DAT), and FIG. 4 (Soybean injury at 9 DAT).

All three experimental formulations provided significantly better crop safety in glyphosate-tolerant (ROUNDUP READY) cotton than DEGREE at the two highest acetochlor application rates (See FIG. 1). Additionally, all encapsulated formulations showed substantially better crop safety than HARNESS at all three application rates. A similar relationship was observed in glyphosate-tolerant (ROUNDUP READY) soybeans; however, in this case the three experimental formulations exhibited significantly better crop safety than DEGREE at all application rates (SEE FIG. 2). Again, all encapsulated formulations provided significantly better crop safety than HARNESS. Crop injury in dicamba-tolerant (DMO) soybeans was similar to that seen in glyphosate-tolerant (ROUNDUP READY) soybeans with no significant differences observed between the two events (See FIGS. 3 and 4). "DMO" refers to a plant expressing a dicamba monooxygenase (DMO) gene that functions to degrade dicamba thereby conferring dicamba tolerance. Crop injury was less overall and differences between the various encapsulated formulations were less pronounced in the dicamba-tolerant soybean study than that seen in glyphosate-tolerant (ROUNDUP READY) soybeans; however, these were two separate studies so comparing across studies is not entirely valid. One could conclude though that dicamba-tolerant soybeans tolerate post-emergent ("POE") applications of acetochlor formulations similar to glyphosate-tolerant (ROUNDUP READY) soybeans.

These data suggest that these experimental formulations provide improved post-emergence crop safety over both DEGREE and HARNESS relative to glyphosate-tolerant (ROUNDUP READY) cotton, glyphosate-tolerant (ROUNDUP READY) soybeans, and dicamba-tolerant soybeans.

Formulations 5291, 5297, and 5295, prepared according to the method described in Example 1, were also tested for preemergence application weed control efficacy and compared to the weed control efficacy of both DEGREE and HARNESS. The weed species tested included Redroot pigweed (*Amaranthus retroflexus*), Lambsquarters (*Chenopodium album*), Yellow foxtail (*Setaria lutescens*), and Barnyardgrass (*Echinochloa crus-galli*).

Substantially greater weed control was evident with all encapsulated formulations in this study. Formulations 5291 and 5297 provided efficacy that was equivalent or superior to that found with DEGREE. See FIGS. 5 through 8. Formulation 5295 (having a greater proportion of internal phase solvent compared to formulations 5291 and 5297) showed significantly less control than all other formulations versus all four species at most application rates. This suggests that excess internal phase solvent may inhibit release of acetochlor to such an extent that weed control efficacy may be compromised.

Example 3

Preparation of Aqueous Dispersions of Microencapsulated Acetochlor

Three aqueous dispersions of microencapsulated acetochlor (designated formulations 3993, 3995, and 3997)

were prepared. All formulations were prepared using the same amine (TETA) and isocyanate (DES N3200), and all formulations contained internal phase solvent, NORPAR 15. The relative ratios of components were held approximately constant. These formulations were prepared using an excess of amine equivalents. The ratios of amine molar equivalents to isocyanate molar equivalents were 1.29:1, 1.26:1, and 1.25:1 in formulations 3993, 3995, and 3997 respectively. The mean particle sizes of each the various formulations were controlled by varying the mixing speed during emulsification.

Formulations 3993, 3995, and 3997 contained the components shown in the following table:

| Component | Form. 3993 | Form. 3995 | Form. 3997 |
|---|---|---|---|
| | Weight of Component (g) | | |
| Internal Phase | | | |
| Acetochlor | 175.0 | 175.0 | 175 |
| NORPAR 15 | 9.3 | 9.3 | 9.11 |
| DES N3200 | 13.01 | 12.87 | 12.79 |
| External Phase | | | |
| Glycerin | 32.5 | 32.0 | 32.0 |
| SOKALAN CP9 | 9.45 | 9.48 | 9.41 |
| Ammonium Caseinate | 0.19 | 0.19 | 0.19 |
| Acid | 0.72 | 0.75 | 0.72 |
| Water | 115.0 | 115.0 | 115.0 |
| TETA, 50% solution | 6.71 | 6.5 | 6.4 |
| Stabilizer | | | |
| Invalon | 23.65 | 23.65 | 23.65 |
| Kelzan CC | 0.21 | 0.21 | 0.21 |
| Antifoam | 0 | 0 | 0 |
| Glycerin | 15.85 | 15.85 | 15.85 |
| Proxel GXL | 0.21 | 0.21 | 0.21 |
| Caustic | 0.07 | 0.07 | 0.07 |
| Buffer | 0.47 | 0.47 | 0.47 |

The aqueous dispersions of microcapsules were prepared substantially as described above in Example 1. During emulsification, the mixer speed was varied by controlling the blender to achieve mean particle sizes as shown in the table:

TABLE

| | Particle Size Parameters | |
|---|---|---|
| Formulation | Mean Particle size (μm) | Standard Deviation (μm) |
| 3993 | 2.01 | 1.14 |
| 3995 | 9.49 | 6.31 |
| 3997 | 10.80 | 7.9 |

Example 4

Preparation of Aqueous Dispersions of Microencapsulated Acetochlor

Three aqueous dispersions of microencapsulated acetochlor (designated formulations 2805A, 2805B, and 2805C) were prepared. These formulations were prepared using MISTAFLEX polyisocyanate blend. These formulations were additionally prepared without the internal phase solvent, NORPAR 15. The ratio of amine molar equivalents to isocyanate molar equivalents was approximately 1.03:1 to 1.04 for each formulation. The mean particle sizes of each the various formulations were controlled varying the mixing speed during emulsification.

To prepare these formulations, large batches of each of the internal phase, the external phase, and the stabilizer solution were prepared containing the components and amounts shown in the following table.

| Component | Form. 2805A | Form. 2805B | Form. 2805C |
|---|---|---|---|
| | Weight of Component (g) | | |
| Internal Phase | | | |
| Acetochlor | | 530 | |
| DES N3200 | | 31.99 | |
| DES W | | 5.65 | |
| External Phase | | | |
| Glycerin | | 104.0 | |
| SOKALAN CP9 | | 30.6 | |
| Ammonium Caseinate | | 0.60 | |
| Acid | | 2.22 | |
| Water | | 373.0 | |
| TETA, 50% solution | 5.48 | 5.50 | 5.39 |
| Stabilizer | | | |
| Invalon | | 71.83 | |
| Glycerin | | 48.15 | |
| Kelzan CC | | 0.64 | |
| Proxel GXL | | 0.64 | |
| Caustic | | 0.22 | |
| Antifoam | | 0.01 | |
| Buffer | | 1.43 | |

The aqueous dispersions of microcapsules were prepared substantially as described above in Example 1. To prepare each formulation, the internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulation | Mean Particle size (μm) | Standard Deviation (μm) |
| 2805A | 2.26 | 1.27 |
| 2805B | 9.73 | 6.33 |
| 2805C | 15.89 | 12.51 |

Example 5

Study of Soybean and Cotton Crop Safety Using Microencapsulated Acetochlor Formulations of the Invention Formulations 3993, 3995, 3997, 2805A, 2805B, and 2805C were applied to glyphosate-tolerant (ROUNDUP READY) soybean (variety AG 4403) and glyphosate-tolerant (ROUNDUP READY) cotton (RR Flex—short to mid-season variety) crops under greenhouse conditions. These formulations were tested against HARNESS and DEGREE. The formulations were applied to post-emergent soybean and cotton plants and measured for phytotoxicity 14 DAT. The results are shown in FIG. 9 (Cotton injury) and FIG. 10 (Soybean injury).

Figure 9:
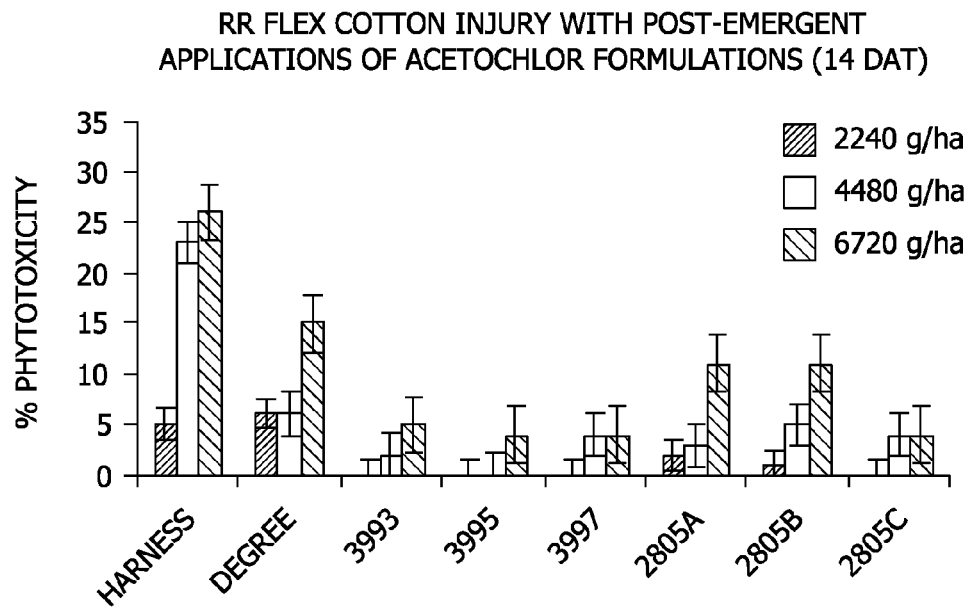
FIG. 9 is a graph depicting cotton injury that occurred with post-emergent applications of various microencapsulated acetochlor formulations as described in Example 5.
Figure 10:
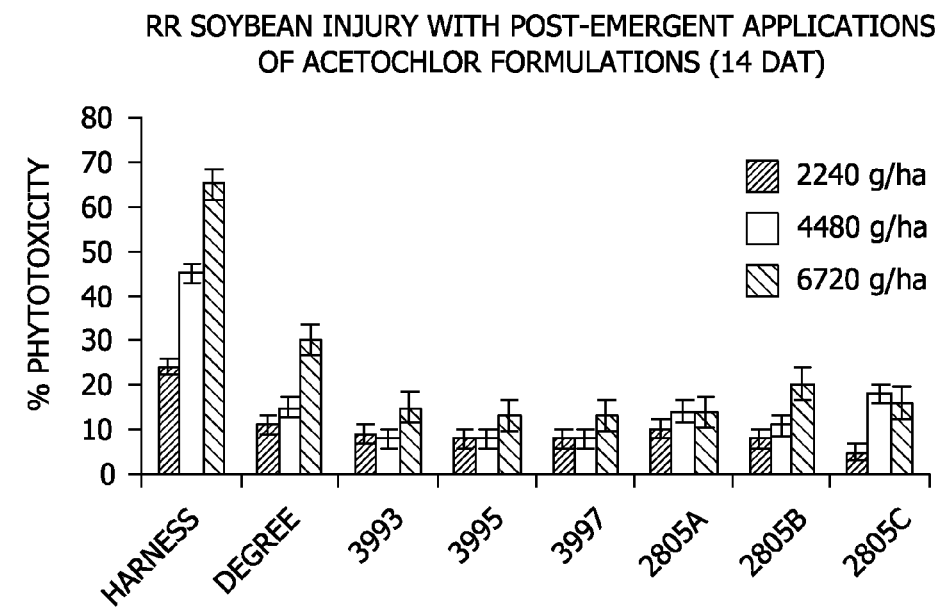
FIG. 10 is a graph depicting soybean injury that occurred with post-emergent applications of various microencapsulated acetochlor formulations as described in Example 5.
Figure 11:
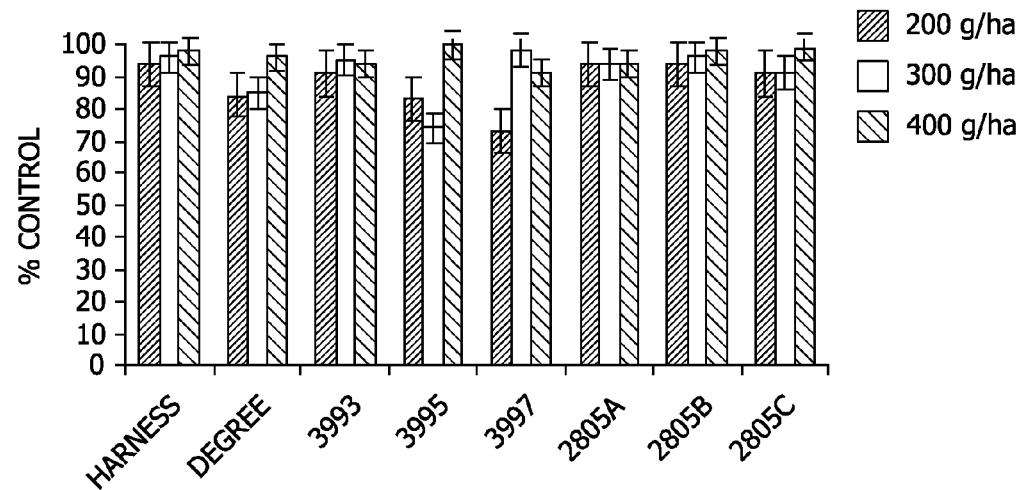
FIG. 11 is a graph depicting control of redroot pigweed achieved with pre-emergent applications of various microencapsulated acetochlor formulations as described in Example 6.
Figure 12:
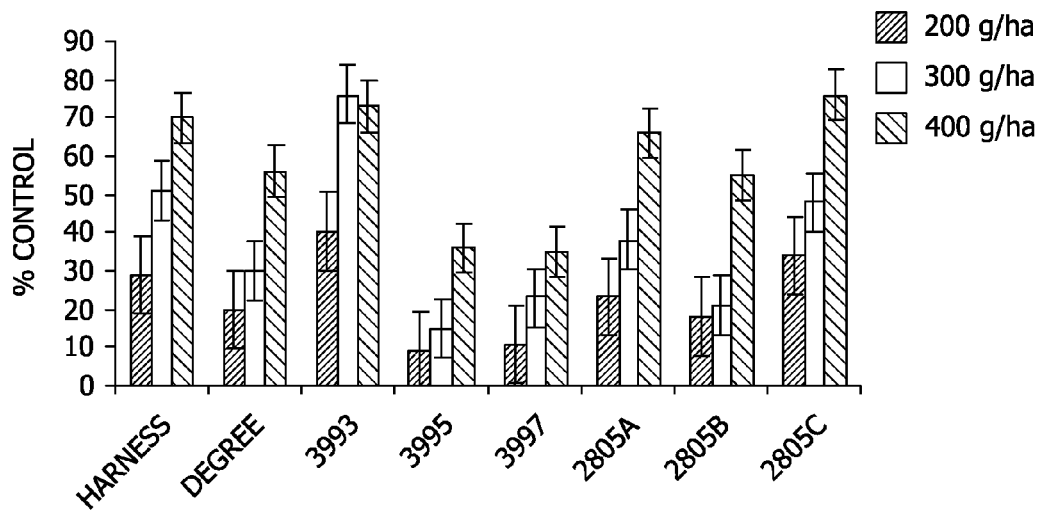
FIG. 12 is a graph depicting control of common lambsquarters control achieved with pre-emergent applications of various microencapsulated acetochlor formulations as described in Example 6.
Figure 13:
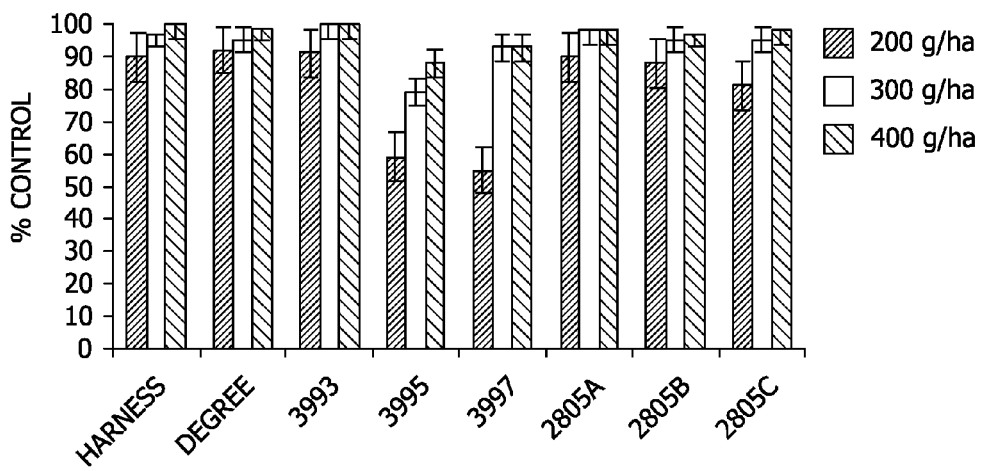
FIG. 13 is a graph depicting control of barnyard grass achieved with pre-emergent applications of various microencapsulated acetochlor formulations as described in Example 6.
Figure 14:
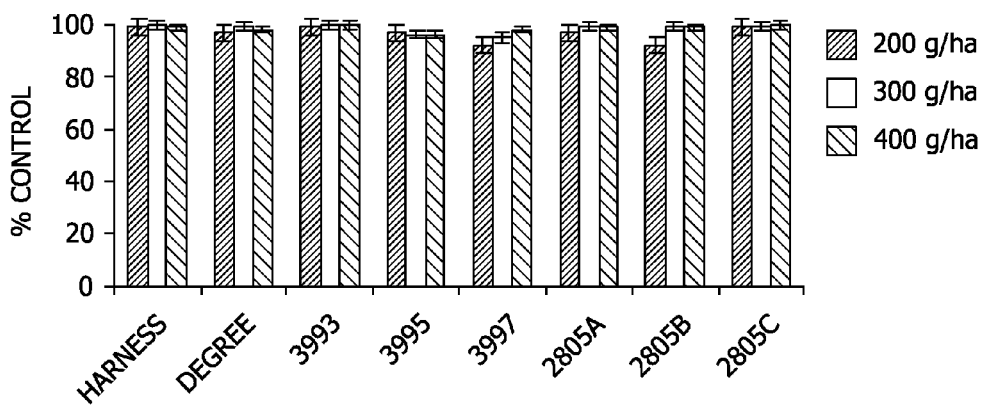
FIG. 14 is a graph depicting control of yellow foxtail achieved with pre-emergent applications of various microencapsulated acetochlor formulations as described in Example 6.
Figure 15:
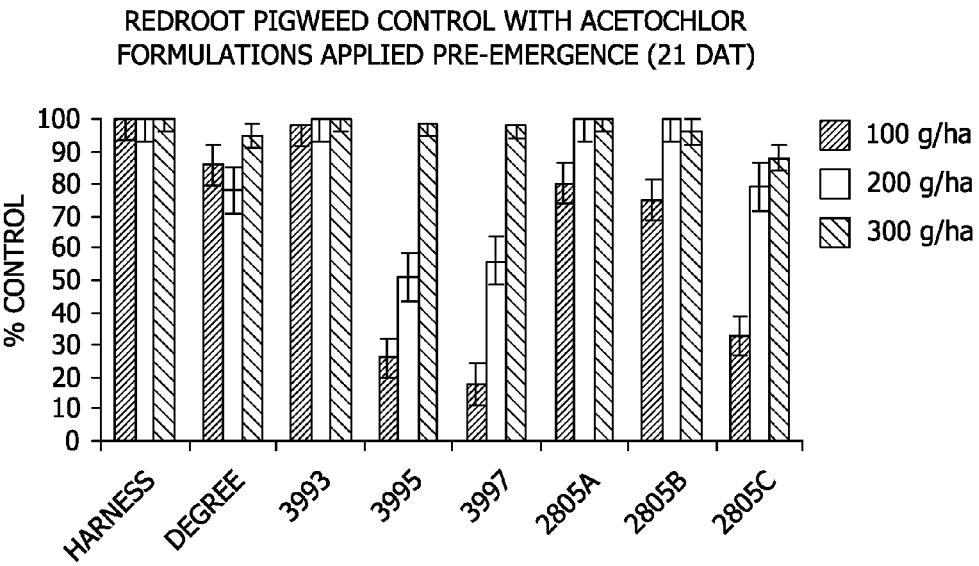
FIG. 15 is a graph depicting control of redroot pigweed achieved with pre-emergent applications of various microencapsulated acetochlor formulations as described in Example 6.
Figure 16:
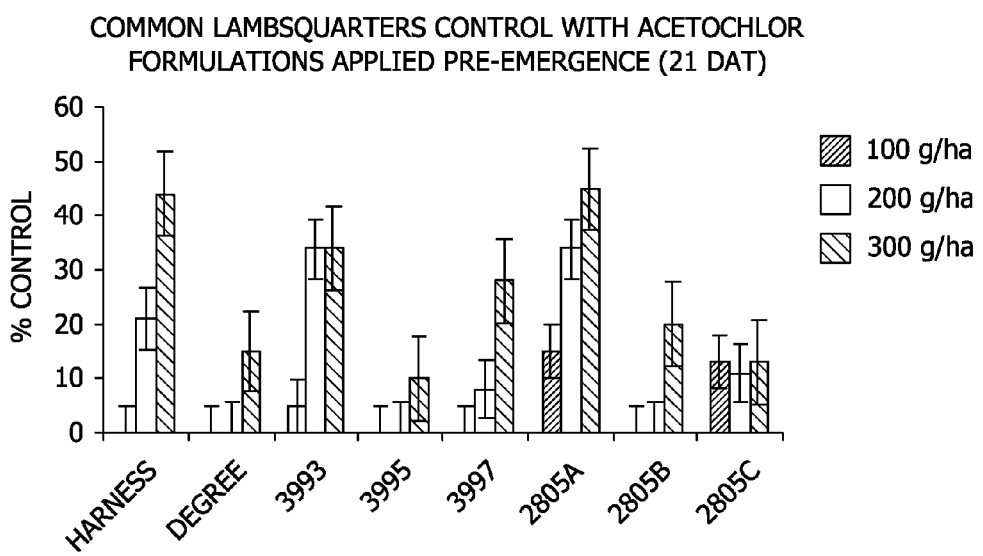
FIG. 16 is a graph depicting control of common lambsquarters control achieved with pre-emergent applications of various microencapsulated acetochlor formulations as described in Example 6.
Figure 17:
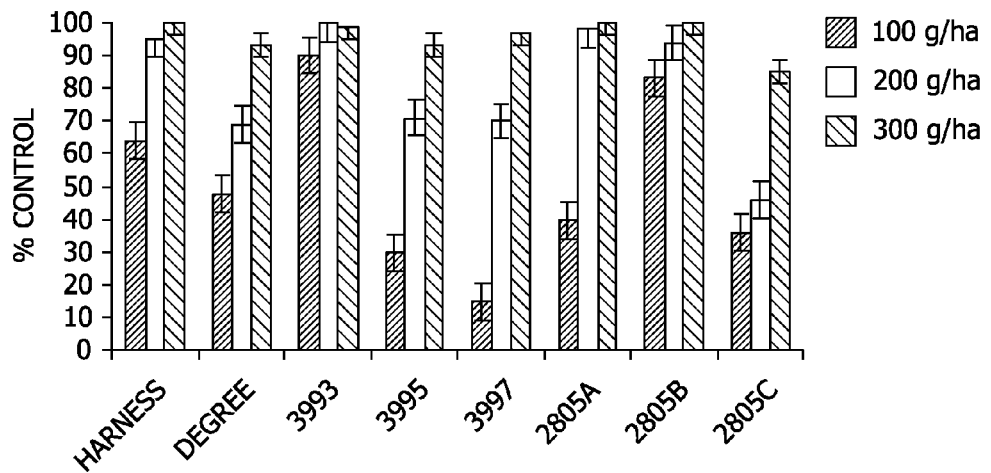
FIG. 17 is a graph depicting control of barnyard grass achieved with pre-emergent applications of various microencapsulated acetochlor formulations as described in Example 6.
Figure 18:
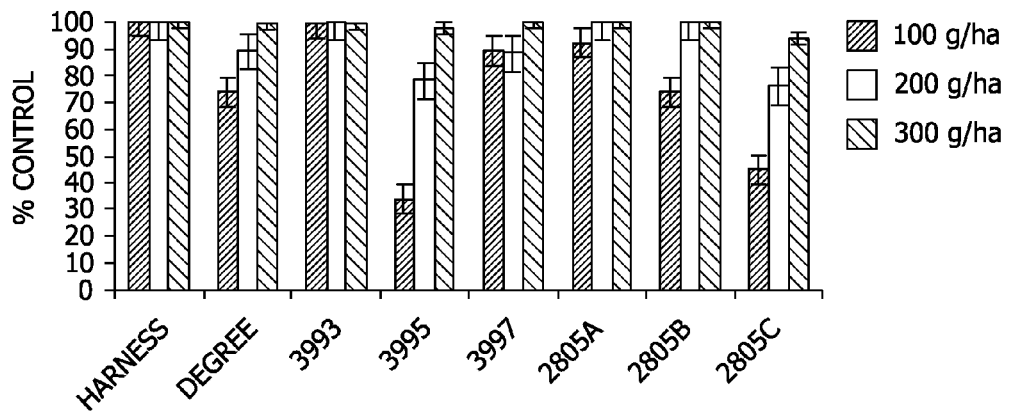
FIG. 18 is a graph depicting control of yellow foxtail achieved with pre-emergent applications of various microencapsulated acetochlor formulations as described in Example 6.

Formulations 3993, 3995, 3997, and 2805C all provided better crop safety in glyphosate-tolerant (ROUNDUP READY) cotton than DEGREE at the highest rate tested and at least one of the two lower rates (FIG. 9). Formulations 2805A and 2805B were not significantly different from Degree at the two higher application rates. Results in glyphosate-tolerant (ROUNDUP READY) soybeans showed all experimental formulations to be less injurious than DEGREE at the highest application rate (FIG. 10). However, only Formulations 3993, 3995, and 3997 provided better crop safety at the middle application rate. The release rates for the tested formulations was measured according to the above described protocol wherein a dispersion of 1% by weight of the encapsulated acetochlor in deionized water was agitated at 150 RPM and 25° C. in a SOTAX AT-7 agitated dissolution test apparatus and sampled at 6 hours and 24 hours. The release rates of the tested formulations is reported in the following table.

| Formulation | Release at 6 hours (ppm) | Release at 24 hours (ppm) |
| --- | --- | --- |
| 3993 | 211 | 280 |
| 3995 | 80 | 104 |
| 3997 | 96 | 128 |
| 2805A | 179 | 312 |
| 2805B | 91 | 152 |
| 2805C | 88 | 140 |
| DEGREE | 129 | 200 |
| DEGREE | 123 | 200 |

Example 6

Weed Control Efficacy Using Microencapsulated Acetochlor Formulations of the Invention Formulations 3993, 3995, 3997, 2805A, 2805B, and 2805C, prepared according to the methods described in Examples 3 and 4, were tested for weed control efficacy and compared to the weed control efficacy of both DEGREE and HARNESS. The weed species tested included Redroot pigweed (*Amaranthus retroflexus*), Lambsquarters (*Chenopodium album*), Yellow foxtail (*Setaria lutescens*), and Barnyardgrass (*Echinochloa crus-galli*). The weed control efficacy data are presented in FIGS. 11 through 18.

Relatively high levels of weed control were also evident in this study. See FIGS. 11 through 14. The data suggest some weakness with Formulations 3995 and 3997 (large microcapsules prepared with a large excess of amine), while the remaining formulations look to be equivalent to DEGREE.

A follow-up study was then conducted with another modification to the protocol. Application rates were lowered and watering was delayed for only three days. The abbreviated delay in watering was instituted with the hope of shortening the length of the assay, while maintaining good efficacy for separating formulations. Data from this study confirmed the weaker efficacy of Formulations 3995 and 3997, particularly as it relates to redroot pigweed and barnyardgrass control. See FIGS. 15 through 18. These data also show lower efficacy with Formulation 2805C (particles having mean diameter of 15.89 µm). The three remaining experimental formulations, 3993, 2805A, and 2805B all showed efficacy which was equivalent to or better than that of DEGREE.

Example 7

Preparation of Aqueous Dispersions of Microencapsulated Acetochlor

Three aqueous dispersions of microencapsulated acetochlor (designated formulations 831A, 831B, and 831D) were prepared. These formulations were prepared using a blend of amines, TETA and XDA, in an approximate weight % ratio of 70:30 and the MISTAFLEX blend of polyisocyanates comprising DES N3200 and DES W. The ratio of amine molar equivalents to isocyanate molar equivalents was approximately 1.04:1 to 1.05:1 for each of these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 831A | Form. 831B | Form. 831D |
| --- | --- | --- | --- |
| | Weight of Component (g) | | |
| Internal Phase | | | |
| Acetochlor | | 504.01 | |
| NORPAR 15 | | 26.27 | |
| MISTAFLEX H9915 | | 36.60 | |
| External Phase | | | |
| Glycerin | | 103.05 | |
| SOKALAN CP9 | | 30.38 | |
| Ammonium Caseinate | | 0.61 | |
| Acid | | 2.35 | |
| Water | | 372.01 | |
| TETA, 50% solution | 4.35 | 4.38 | 4.37 |
| Xylylenediamine, 50% solution | 1.90 | 1.91 | 1.87 |
| Stabilizer | | | |
| Invalon | | 71.83 | |
| Glycerin | | 0.64 | |
| Kelzan CC | | 0.01 | |
| Proxel GXL | | 48.15 | |
| Caustic | | 0.64 | |
| Antifoam | | 0.22 | |
| Buffer | | 1.43 | |

The aqueous dispersions of microcapsules were prepared substantially as described above in Example 1. To prepare each formulation, the internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| | Particle Size Parameters | |
| --- | --- | --- |
| Formulation | Mean Particle size (µm) | Standard Deviation (µm) |
| 831A | 2.11 | 1.22 |
| 831B | 8.48 | 5.82 |
| 831D | 11.7 | |

Example 8

Preparation of Aqueous Dispersions of Microencapsulated Acetochlor

Four aqueous dispersions of microencapsulated acetochlor (designated formulations 838A, 838B, 838C, and 838D) were prepared. These formulations were prepared using a blend of amines, TETA and XDA, similarly to Example 7, but the weight % ratio was changed to 80:20. The formulations were prepared using the MISTAFLEX blend of polyisocyanates comprising DES N3200 and DES W. The ratio of amine molar equivalents to isocyanate molar equivalents was approximately 1.04:1 to 1.05:1 for each of these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 838A | Form. 838B | Form. 838C | Form. 838D |
|---|---|---|---|---|
| | Weight of Component (g) | | | |
| Internal Phase | | | | |
| Acetochlor | 669.0 | | | |
| NORPAR 15 | 34.92 | | | |
| MISTAFLEX H9915 | 49.10 | | | |
| External Phase | | | | |
| Glycerin | 137.0 | | | |
| SOKALAN CP9 | 40.45 | | | |
| Ammonium Caseinate | 0.81 | | | |
| Acid | 3.10 | | | |
| Water | 494.00 | | | |
| TETA, 50% solution | 4.80 | 4.79 | 4.78 | 4.80 |
| Xylylenediamine, 50% solution | 1.2 | 1.21 | 1.22 | 1.21 |
| Stabilizer | | | | |
| Invalon | 95.48 | | | |
| Glycerin | 0.86 | | | |
| Kelzan CC | 0.02 | | | |
| Proxel GXL | 64.0 | | | |
| Caustic | 0.86 | | | |
| Antifoam | 0.29 | | | |
| Buffer | 1.91 | | | |

The aqueous dispersions of microcapsules were prepared substantially as described above in Example 1. To prepare each formulation, the internal phase, external phase, and stabilizer batches were divided into smaller approximately equal weight batches and combined as described in Example 1. Four separate amine solutions were used to initiate polymerization. During emulsification, the mixer speed was varied by controlling the blender to achieve mean particle sizes as shown in the table:

TABLE

| Particle Size Parameters | | |
|---|---|---|
| Formulation | Mean Particle size (μm) | Standard Deviation (μm) |
| 838A | 2.06 | 1.12 |
| 838B | 6.74 | 4.44 |
| 838C | 12.84 | 8.16 |
| 838D | 8.35 | 5.49 |

Example 9

Preparation of Aqueous Dispersions of Microencapsulated Acetochlor

Four aqueous dispersions of microencapsulated acetochlor (designated formulations 843A, 843B, 843C, and 843D) were prepared. These formulations were prepared using a blend of amines, TETA and XDA, similarly to Examples 7 and 8, but the weight % ratio was changed to 90:10. The formulations were prepared using the MISTAFLEX blend of polyisocyanates comprising DES N3200 and DES W. The ratio of amine molar equivalents to isocyanate molar equivalents was approximately 1.04:1 to 1.05:1 for each of these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 838A | Form. 838B | Form. 838C | Form. 838D |
|---|---|---|---|---|
| | Weight of Component (g) | | | |
| Internal Phase | | | | |
| Acetochlor | 669.0 | | | |
| NORPAR 15 | 35.0 | | | |
| MISTAFLEX H9915 | 49.58 | | | |
| External Phase | | | | |
| Glycerin | 137.10 | | | |
| SOKALAN CP9 | 40.40 | | | |
| Ammonium Caseinate | 0.81 | | | |
| Acid | 3.0 | | | |
| Water | 494.02 | | | |
| TETA, 50% solution | 5.17 | 5.18 | 5.16 | 5.17 |
| Xylylenediamine, 50% solution | 0.59 | 0.60 | 0.58 | 0.59 |
| Stabilizer | | | | |
| Invalon | 95.48 | | | |
| Glycerin | 0.86 | | | |
| Kelzan CC | 0.02 | | | |
| Proxel GXL | 64.0 | | | |
| Caustic | 0.86 | | | |
| Antifoam | 0.29 | | | |
| Buffer | 1.91 | | | |

The aqueous dispersions of microcapsules were prepared substantially as described above in Example 1. To prepare each formulation, the internal phase, external phase, and stabilizer batches were divided into smaller approximately equal weight batches and combined as described in Example 1. Four separate amine solutions were used to initiate polymerization. During emulsification, the mixer speed was varied by controlling the blender to achieve mean particle sizes as shown in the table:

TABLE

Particle Size Parameters

| Formulation | Mean Particle size (μm) | Standard Deviation (μm) |
| --- | --- | --- |
| 843A | 2.18 | 1.16 |
| 843B | 7.62 | 5.05 |
| 843C | 11.68 | 7.92 |
| 843D | 5.58 | 3.74 |

Example 10

Figure 19:
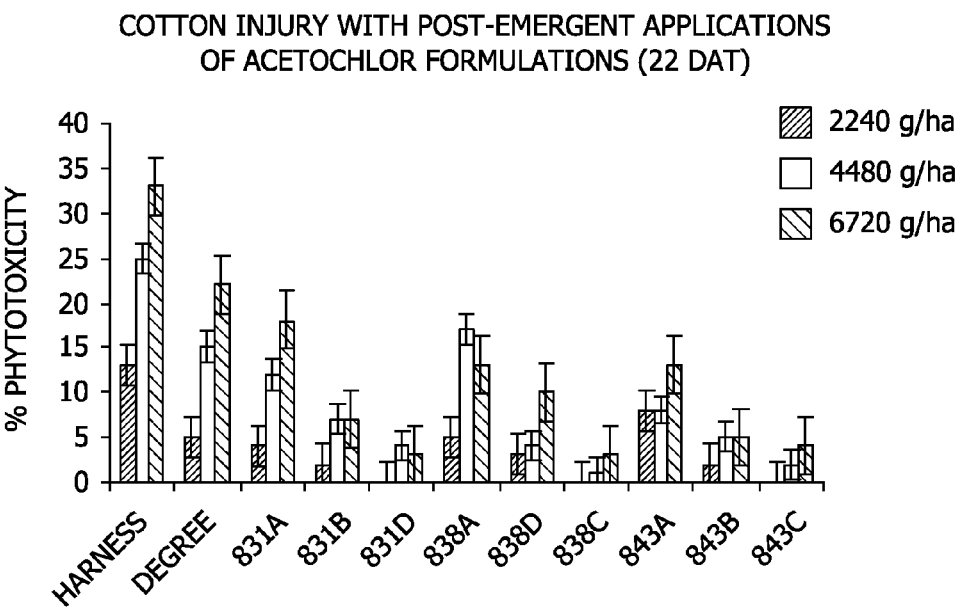
FIG. 19 is a graph depicting cotton injury that occurred with post-emergent applications of various microencapsulated acetochlor formulations as described in Example 10.
Figure 20:
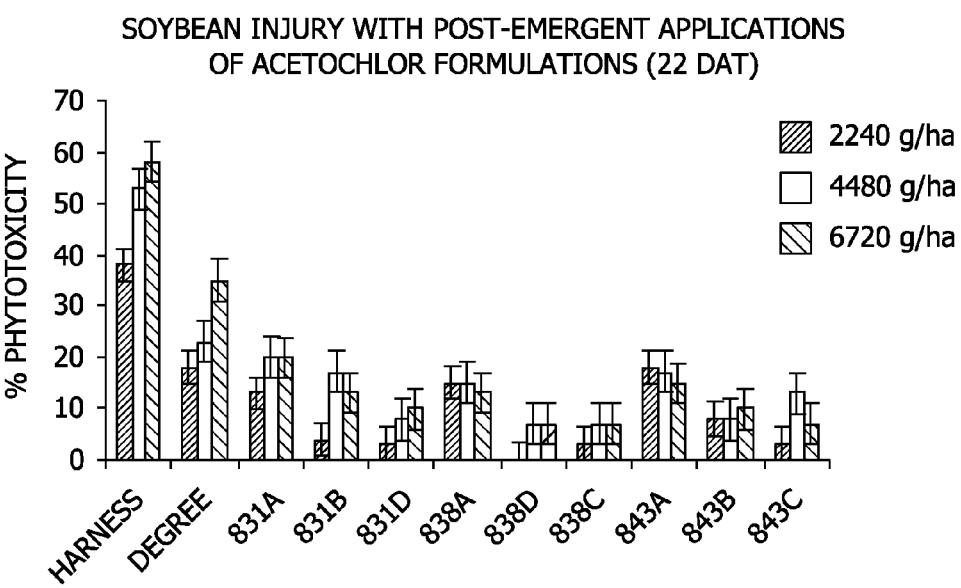
FIG. 20 is a graph depicting soybean injury that occurred with post-emergent applications of various microencapsulated acetochlor formulations as described in Example 10.

Study of Soybean and Cotton Crop Safety and Post-emergence Weed Control Efficacy Using Microencapsulated Acetochlor Formulations of the Invention Formulations 831A, 831B, 831D, 838A, 838D, 838C, 843A, 843B, and 843C (prepared according to the methods described in Examples 7, 8, and 9) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS and DEGREE. The formulations were applied to post-emergent soybean and cotton plants and measured for phytotoxicity 22 DAT. The results are shown in FIG. 19 (Cotton injury) and FIG. 20 (Soybean injury).

All formulations with small capsule size (831A, 838A, 843A) showed cotton and soybean injury that was essentially equivalent to that seen with DEGREE. See FIGS. 19 and 20. Formulations 831A, 838A, and 843A were characterized by relatively high release rates, as measured in a SOTAX AT-7 dissolution test apparatus according to the method described herein, while the other formulations released at somewhat slower rates. For comparison, the release from DEGREE was measured twice. See the following table for the release rates of the tested formulations.

| Formulation | Release at 6 hours (ppm) | Release at 24 hours (ppm) |
| --- | --- | --- |
| 831A | 245 | 305 |
| 831B | 168 | 191 |
| 831D | 156 | 182 |
| 838A | 186 | 275 |
| 838D | 170 | 214 |
| 838C | 73 | 90 |
| 843A | 188 | 286 |
| 843B | 94 | 123 |
| 843C | 96 | 134 |
| DEGREE | 131 | 202 |
| DEGREE | 136 | 200 |

Figure 21:
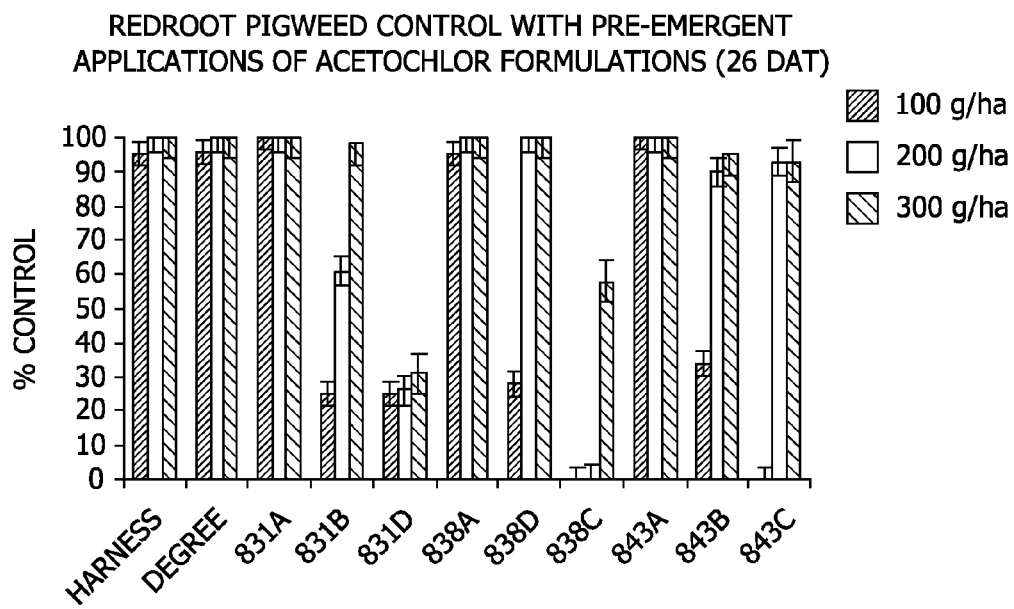
FIG. 21 is a graph depicting control of redroot pigweed achieved with pre-emergent applications of various microencapsulated acetochlor formulations as described in Example 10.
Figure 22:
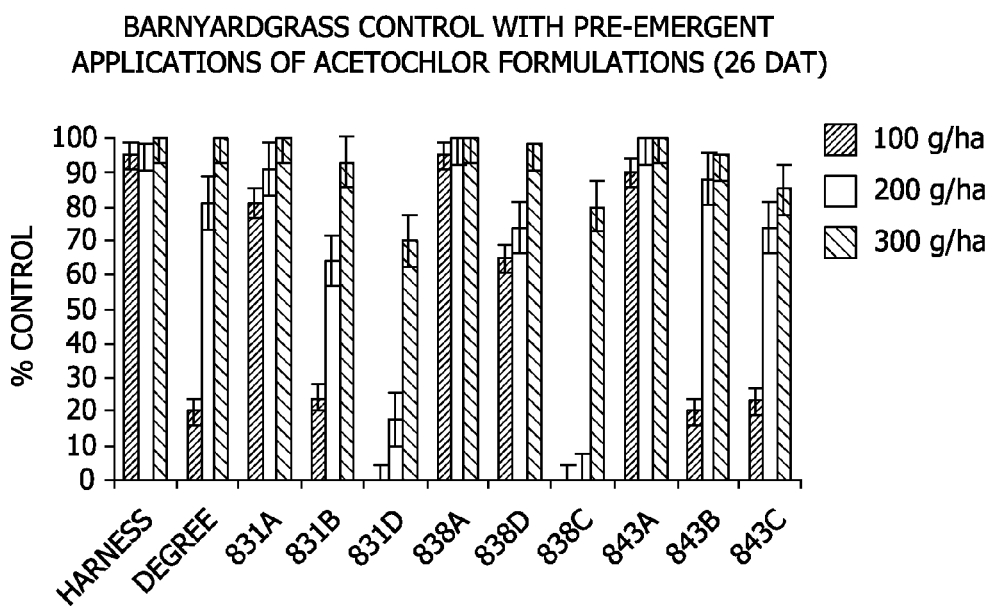
FIG. 22 is a graph depicting control of barnyard grass achieved with pre-emergent applications of various microencapsulated acetochlor formulations as described in Example 10.
Figure 23:
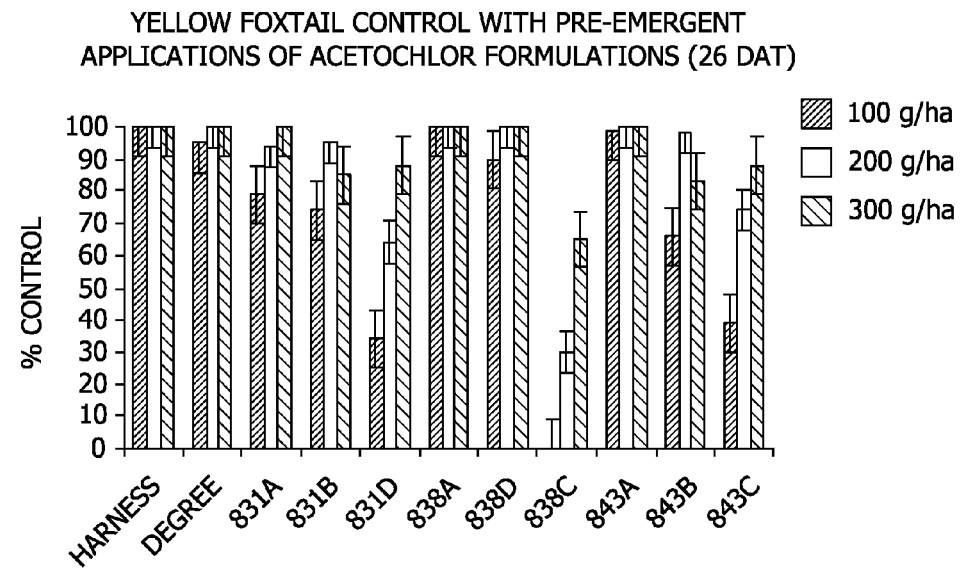
FIG. 23 is a graph depicting control of yellow foxtail achieved with pre-emergent applications of various microencapsulated acetochlor formulations as described in Example 10.

Formulations 831A, 831B, 831D, 838A, 838D, 838C, 843A, 843B, and 843C were also tested for weed control efficacy and compared to the weed control efficacy of both DEGREE and HARNESS. The weed species tested included Redroot pigweed (*Amaranthus retroflexus*), Barnyardgrass (*Echinochloa crus-galli*), and Yellow foxtail (*Setaria lutescens*). The weed control efficacy data are presented in FIGS. 21, 22, and 23.

As expected these formulations provided weed control efficacy versus redroot pigweed, barnyardgrass, and yellow foxtail on par with DEGREE. See FIGS. 21, 22, and 23). Formulations with the largest capsule sizes, 831D, 838C, and 843C), however, provided weed control that was in most cases inferior to DEGREE. Formulations with mid-size capsule showed the best balance between improved crop safety and acceptable weed control. Changing the amine ratios (TETA:XDA) did not appear to influence crop safety. There did appear to be a trend towards better weed control efficacy with higher levels of TETA (see redroot pigweed and barnyardgrass control).

Example 11

Preparation of Aqueous Dispersions of Microencapsulated Acetochlor

Two aqueous dispersions of microencapsulated acetochlor (designated formulations 874A and 874B) were prepared. These formulations were prepared using the MISTAFLEX blend of polyisocyanates comprising DES N3200 and DES W and a single amine, TETA. The ratio of amine molar equivalents to isocyanate molar equivalents was approximately 1.2:1 for these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 874A Weight of Component (g) | Form. 874B |
| --- | --- | --- |
| Internal Phase | | |
| Acetochlor | 352.70 | |
| NORPAR 15 | 18.43 | |
| MISTAFLEX H9915 | 25.73 | |
| External Phase | | |
| Glycerin | 64.60 | |
| SOKALAN CP9 | 19.06 | |
| Ammonium Caseinate | 0.38 | |
| Acid | 1.39 | |
| Water | 232.80 | |
| TETA, 50% solution | 6.46 | 6.45 |
| Stabilizer | | |
| Invalon | 47.89 | |
| Glycerin | 0.43 | |
| Kelzan CC | 0.01 | |
| Proxel GXL | 32.10 | |
| Caustic | 0.43 | |
| Antifoam | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulation | Mean Particle size (μm) | Standard Deviation (μm) |
| 874A | 2.02 | 1.06 |
| 874B | 7.33 | 7.93 |

Example 12

Preparation of Aqueous Dispersions of Microencapsulated Acetochlor

Two aqueous dispersions of microencapsulated acetochlor (designated formulations 877A and 877B) were prepared. These formulations were prepared using the MISTAFLEX blend of polyisocyanates comprising DES N3200 and DES W and a single amine, TETA. The ratio of amine molar equivalents to isocyanate molar equivalents was slightly lower than in preceding Example 11. Herein, the ratio is approximately 1.1:1 for these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 877A | Form. 877B |
|---|---|---|
| | Weight of Component (g) | |
| Internal Phase | | |
| Acetochlor | 353.0 | |
| NORPAR 15 | 18.43 | |
| MISTAFLEX H9915 | 26.30 | |
| External Phase | | |
| Glycerin | 64.69 | |
| SOKALAN CP9 | 19.1 | |
| Ammonium Caseinate | 0.38 | |
| Acid | 1.40 | |
| Water | 233.08 | |
| TETA, 50% solution | 6.02 | 6.02 |
| Stabilizer | | |
| Invalon | 47.89 | |
| Glycerin | 0.43 | |
| Kelzan CC | 0.01 | |
| Proxel GXL | 32.10 | |
| Caustic | 0.43 | |
| Antifoam | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 877A | 2.08 | 1.13 |
| 877B | 7.68 | 5.14 |

Example 13

Preparation of Aqueous Dispersions of Microencapsulated Acetochlor

Two aqueous dispersions of microencapsulated acetochlor (designated formulations 880A and 880B) were prepared. These formulations were prepared using the MISTAFLEX blend of polyisocyanates comprising DES N3200 and DES W and a single amine, TETA. The ratio of amine molar equivalents to isocyanate molar equivalents was higher than in Example 11. Herein, the ratio is approximately 1.3:1 for these formulations. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 880A | Form. 880B |
|---|---|---|
| | Weight of Component (g) | |
| Internal Phase | | |
| Acetochlor | 353 | |
| NORPAR 15 | 18.42 | |
| MISTAFLEX H9915 | 25.33 | |
| External Phase | | |
| Glycerin | 64.50 | |
| SOKALAN CP9 | 19.05 | |
| Ammonium Caseinate | 0.37 | |
| Acid | 1.40 | |
| Water | 232.5 | |
| TETA, 50% solution | 6.88 | 6.87 |
| Stabilizer | | |
| Invalon | 47.89 | |
| Glycerin | 0.43 | |
| Kelzan CC | 0.01 | |
| Proxel GXL | 32.10 | |
| Caustic | 0.43 | |
| Antifoam | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 880A | 2.17 | 1.15 |
| 880B | 8.21 | 5.20 |

Example 14

Preparation of Aqueous Dispersions of Microencapsulated Acetochlor

Two aqueous dispersions of microencapsulated acetochlor (designated formulations 883A and 885A) were prepared. These formulations were prepared using the MISTAFLEX blend of polyisocyanates comprising DES N3200 and DES W and a single amine, TETA. The ratio of amine molar equivalents to isocyanate molar equivalents was 1.15:1 and 1.25:1 for formulations 883A and 885A, respectively. The mean particle sizes of each the various formulations were controlled varying the mixing speed during emulsification.

To prepare these formulations, the internal phase, the external phase, the amine solution, and the stabilizer solution were prepared containing the components and amounts shown in the following table:

| Component | 883A Weight of Component (g) | 885A Weight of Component (g) |
|---|---|---|
| Internal Phase | | |
| Acetochlor | 352.75 | 174.18 |
| NORPAR | 18.44 | 9.10 |
| MISTAFLEX | 25.97 | 12.65 |
| External Phase | | |
| Glycerin | 64.65 | 32.0 |
| SOKALAN CP9 | 19.07 | 9.4 |
| Ammonium Caseinate | 0.38 | 0.19 |
| Acid | 1.37 | 0.70 |
| Water | 232.92 | 115.0 |
| TETA, 50% solution | 12.63 | 6.67 |
| Stabilizer | | |
| Invalon | 47.89 | 23.65 |
| Kelzan CC | 0.43 | 0.21 |
| Antifoam | 0.01 | 0 |
| Glycerin | 32.10 | 15.85 |
| Proxel GXL | 0.43 | 0.21 |
| Caustic | 0.15 | 0.07 |
| Buffer | 0.96 | 0.47 |

The aqueous dispersions of microcapsules were prepared substantially as described above in Example 1. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 883A | 2.27 | 2.28 |
| 885A | 1.94 | 1.06 |

Example 15

Figure 24:
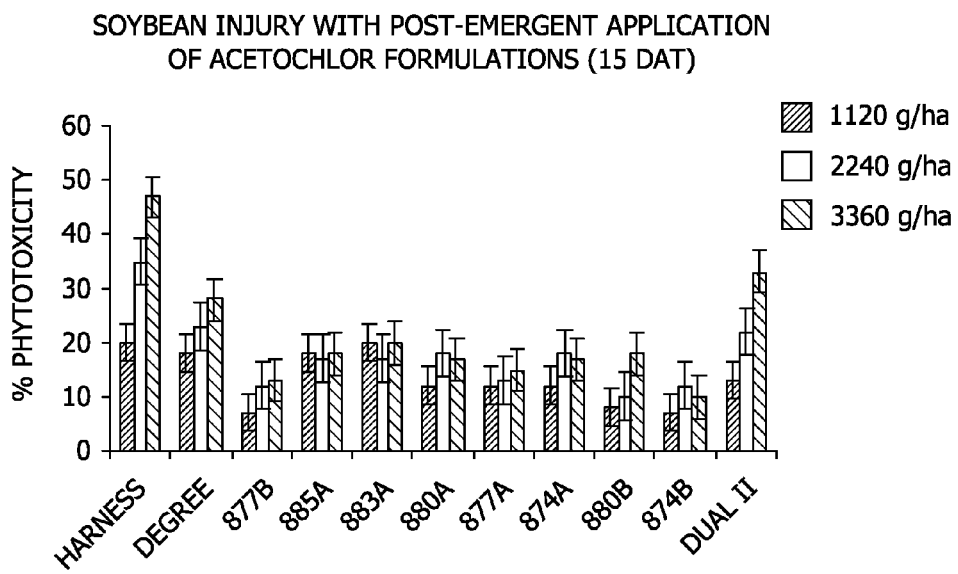
FIG. 24 is a graph depicting soybean injury that occurred with post-emergent applications of various microencapsulated acetochlor formulations as described in Example 15.
Figure 25:
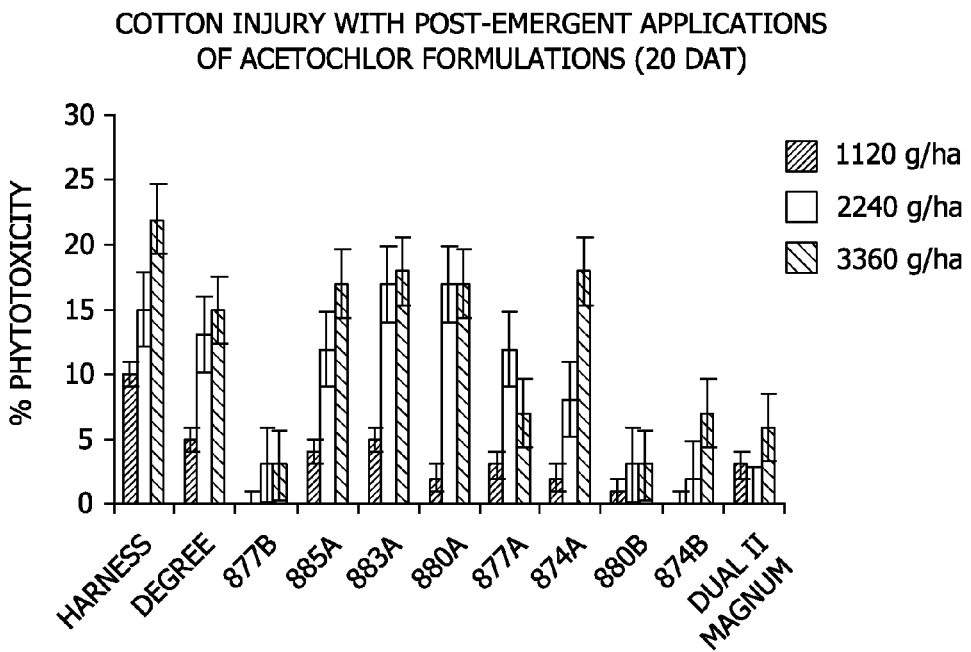
FIG. 25 is a graph depicting cotton injury that occurred with post-emergent applications of various microencapsulated acetochlor formulations as described in Example 15.
Figure 26:
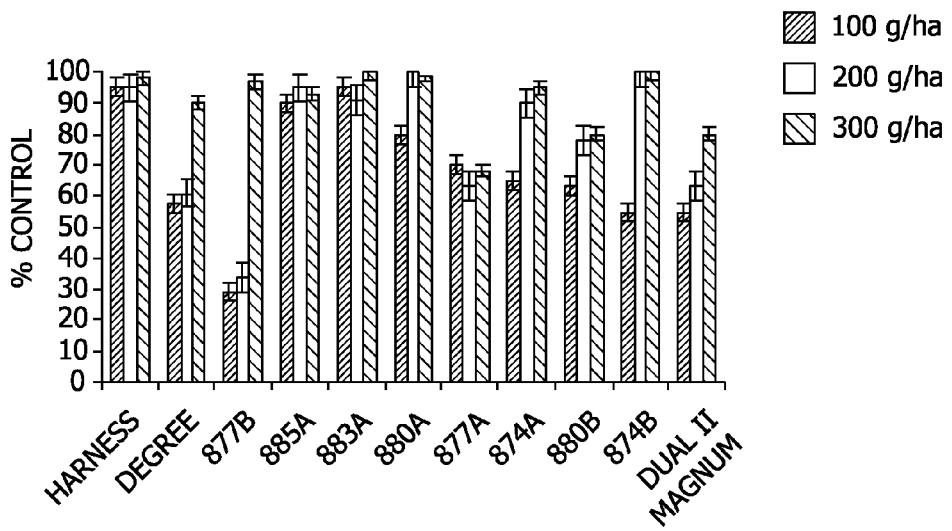
FIG. 26 is a graph depicting control of redroot pigweed achieved with pre-emergent applications of various microencapsulated acetochlor formulations as described in Example 15.
Figure 27:
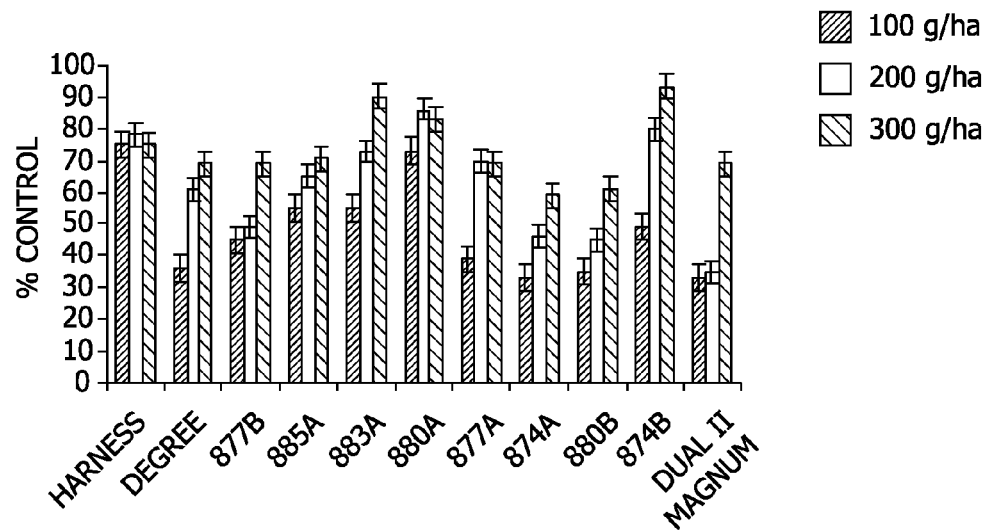
FIG. 27 is a graph depicting control of common lambsquarters achieved with pre-emergent applications of various microencapsulated acetochlor formulations as described in Example 15.
Figure 28:
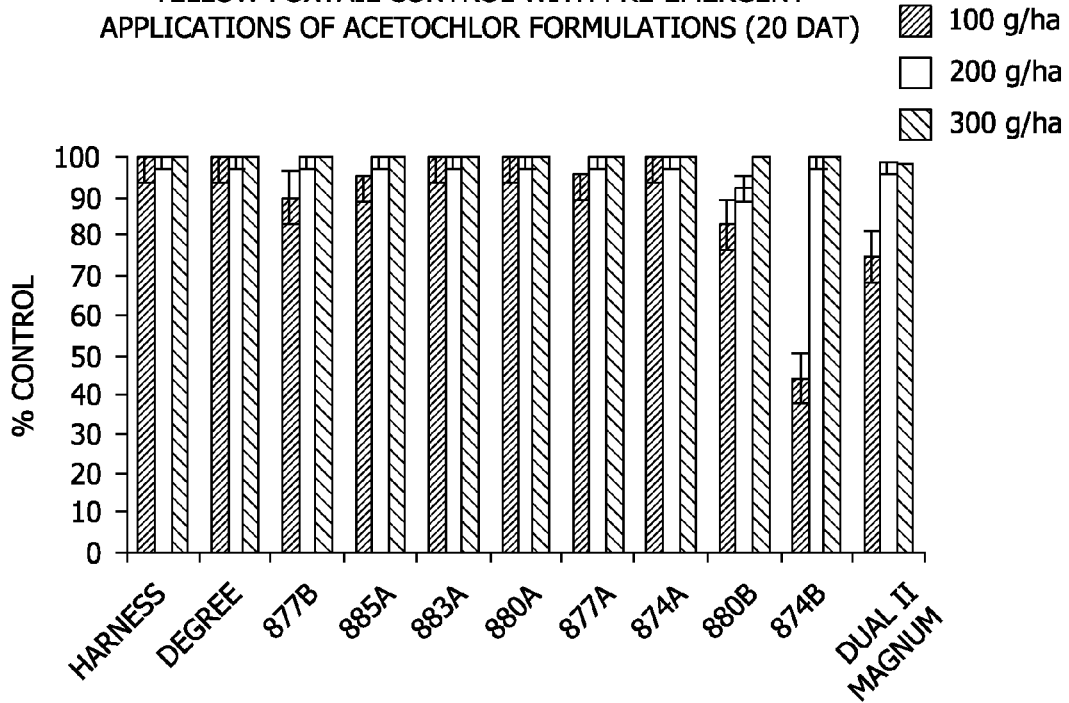
FIG. 28 is a graph depicting control of yellow foxtail achieved with pre-emergent applications of various microencapsulated acetochlor formulations as described in Example 15.
Figure 29:
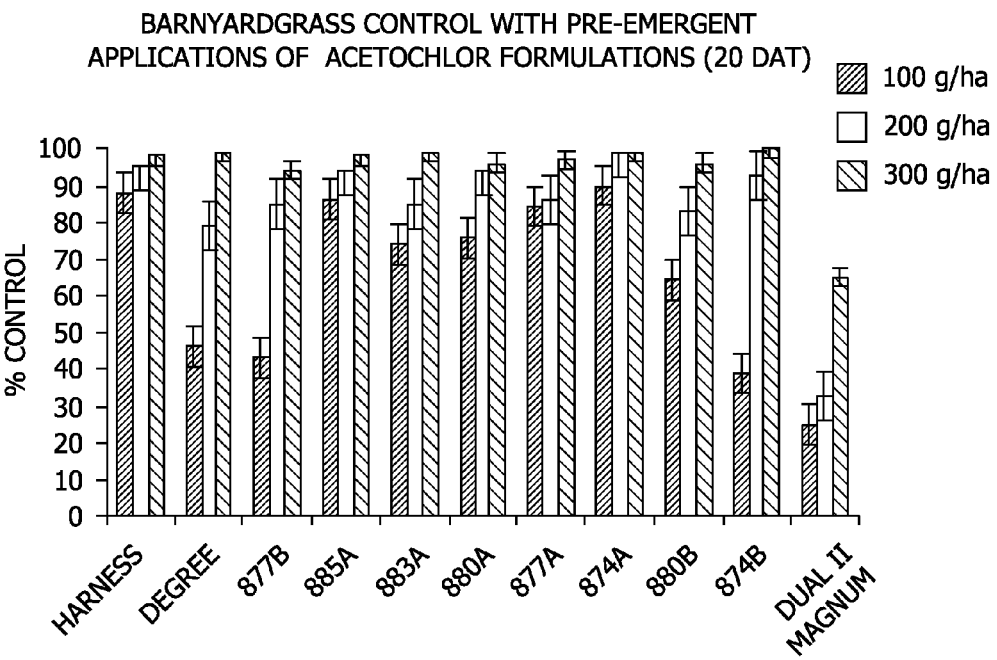
FIG. 29 is a graph depicting control of barnyard grass achieved with pre-emergent applications of various microencapsulated acetochlor formulations as described in Example 15.

Study of Soybean and Cotton Crop Safety and Post-emergence Weed Control Efficacy Using Microencapsulated Acetochlor Formulations of the Invention Formulations 874A, 874B, 877A, 877B, 880A, 880B, 883A, and 885A (prepared according to the methods described in Examples 11 through 14) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS and DEGREE and against Dual II MAGNUM, available from Syngenta, which comprises s-metalochlor as the active ingredient and proprietary ingredients. The formulations were applied to post-emergent soybean and cotton plants and measured for phytotoxicity. The results are shown in FIG. 24 (Soybean injury 15 DAT) and FIG. 25 (Cotton injury 20 DAT). The most consistent crop safety was obtained with formulation 874B, 877B, and 800B. See FIGS. 24 and 25. All three formulations provided crop safety that was significantly better than that seen with DEGREE or HARNESS. Note that each of these formulations had particles sizes in the 7-8 micron range and that altering the amine levels did not appreciably change results among the formulations. Dual II MAGNUM gave injury that was similar to these three in cotton, but showed significantly greater injury in soybeans. All remaining experimental formulations exhibited crop injury that was similar to or slightly less than that shown by DEGREE.

Formulations 874A, 874B, 877A, 877B, 880A, 880B, 883A, and 885A were also tested for weed control efficacy and compared to the weed control efficacy of both DEGREE and HARNESS. The weed species tested included Redroot pigweed (*Amaranthus retroflexus*), Lambsquarters (*Chenopodium album*), Barnyardgrass (*Echinochloa crus-galli*), and Yellow foxtail (*Setaria lutescens*). The weed control efficacy data are presented in FIGS. 26 through 29.

Overall these experimental formulations provided efficacy that was generally equal to or better than that of DEGREE. See FIGS. 26 through 29. Control of redroot pigweed showed that formulation 877B was less efficacious at the lowest application, formulation 877A was less effective at the highest rate, and formulations 885A, 883A, 880A, 874A, and 874B showed better efficacy than both DEGREE and Dual II MAGNUM. Lambsquarter control indicated formulations 874A and 880B to be slightly weaker than DEGREE. All other formulations were equal to or better than DEGREE and Dual II MAGNUM. Yellow foxtail control was excellent with all formulations, although formulation 874B did show some weakness at the lowest application rate. All formulations were equal to or better than DEGREE in the control of barnyardgrass. Note the significant weakness of Dual II MAGNUM in the control of barnyardgrass relative to all of the acetochlor formulations.

Example 16

Preparation of Aqueous Dispersions of Microencapsulated Acetochlor

Two aqueous dispersions of microencapsulated acetochlor (designated formulations 911A and 911B) were prepared. These formulations were prepared using a polyisocyanate blend of DES N3200 and DES W in an approximately 50:50 weight ratio. The polyisocyanates and TETA amine used to prepare the shell wall were added to yield a ratio of amine molar equivalents to isocyanate molar equivalents of approximately 1.2:1. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form 911A | Form. 911B |
|---|---|---|
| | Weight of Component (g) | |
| Internal Phase | | |
| Acetochlor | 352.7 | |
| NORPAR | 18.41 | |
| DES N3200 | 12.59 | |
| DES W | 12.59 | |
| External Phase | | |
| Glycerin | 64.50 | |
| SOKALAN CP9 | 19.0 | |
| Ammonium Caseinate | 0.4 | |
| Acid | 1.39 | |
| Water | 232.3 | |
| TETA, 50% solution | 7.1 | 7.1 |
| Stabilizer | | |
| Invalon | 47.89 | |
| Kelzan CC | 0.43 | |
| Antifoam | 0.01 | |
| Glycerin | 32.10 | |
| Proxel GXL | 0.43 | |
| Caustic | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 911A | 7.73 | 5.64 |
| 911B | 2.62 | 2.94 |

Example 17

Preparation of Aqueous Dispersions of Microencapsulated Acetochlor

Two aqueous dispersions of microencapsulated acetochlor (designated formulations 914A and 914C) were prepared. These formulations were prepared using a polyisocyanate blend of DES N3200 and DES W in an approximately 85:15 weight ratio. The polyisocyanates and TETA amine used to prepare the shell wall were added in amounts at molar equivalents ratios of amine molar equivalents to isocyanate molar equivalents of approximately 1.2:1. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 914A | Form. 914C |
|---|---|---|
| | Weight of Component (g) | |
| Internal Phase | | |
| Acetochlor | 352.70 | |
| NORPAR | 18.40 | |
| DES N3200 | 21.99 | |
| DES W | 4.0 | |
| External Phase | | |
| Glycerin | 64.6 | |
| SOKALAN CP9 | 19.1 | |
| Ammonium Caseinate | 0.4 | |
| Acid | 1.38 | |
| Water | 232.77 | |
| TETA, 50% solution | 6.46 | 6.46 |
| Stabilizer | | |
| Invalon | 47.89 | |
| Kelzan CC | 0.43 | |
| Antifoam | 0.01 | |
| Glycerin | 32.10 | |
| Proxel GXL | 0.43 | |
| Caustic | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 914A | 2.21 | 1.25 |
| 914C | 7.43 | 5.05 |

Example 18

Preparation of Aqueous Dispersions of Microencapsulated Acetochlor

Two aqueous dispersions of microencapsulated acetochlor (designated formulations 917A and 917B) were prepared. These formulations were prepared using a polyisocyanate blend of DES N3200 and DES W in an approximately 70:30 weight ratio. The polyisocyanates and TETA amine used to prepare the shell wall were added in amounts at molar equivalents ratios of amine molar equivalents to isocyanate molar equivalents of approximately 1.2:1. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 917A | Form. 917B |
|---|---|---|
|  | Weight of Component (g) | |
| Internal Phase | | |
| Acetochlor | 352.65 | |
| NORPAR | 18.40 | |
| DES N3200 | 17.85 | |
| DES W | 7.66 | |
| External Phase | | |
| Glycerin | 64.57 | |
| SOKALAN CP9 | 19.01 | |
| Ammonium Caseinate | 0.38 | |
| Acid | 1.41 | |
| Water | 232.60 | |
| TETA, 50% solution | 6.74 | 6.74 |
| Stabilizer | | |
| Invalon | 47.89 | |
| Kelzan CC | 0.43 | |
| Antifoam | 0.01 | |
| Glycerin | 32.10 | |
| Proxel GXL | 0.43 | |
| Caustic | 0.15 | |
| Buffer | 0.96 | |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 917A | 1.99 | 1.1 |
| 917B | 7.55 | 5.01 |

Example 19

Figure 30:
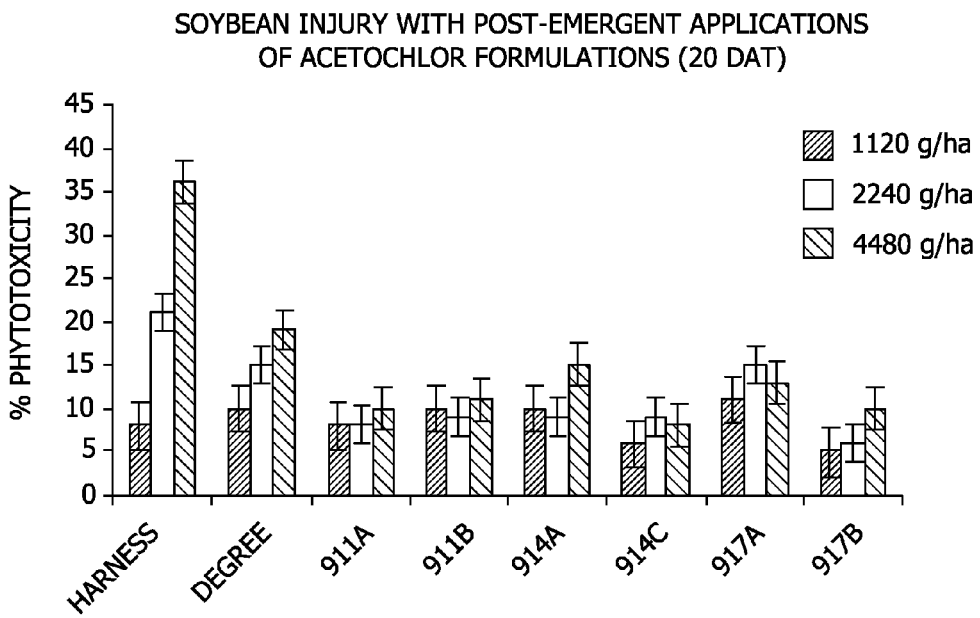
FIG. 30 is a graph depicting soybean injury that occurred with post-emergent applications of various microencapsulated acetochlor formulations as described in Example 19.
Figure 31:
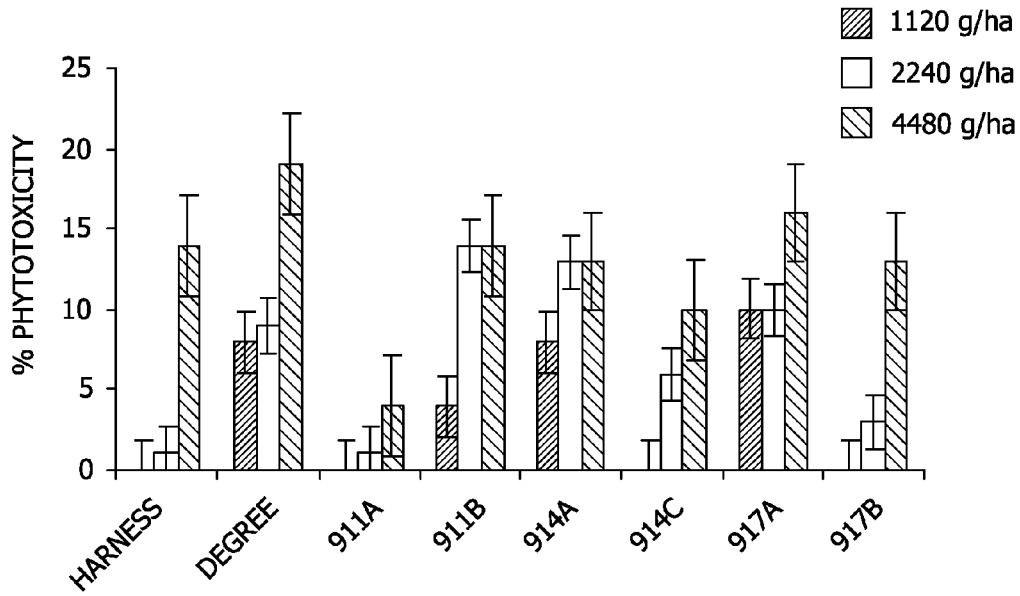
FIG. 31 is a graph depicting cotton injury that occurred with post-emergent applications of various microencapsulated acetochlor formulations as described in Example 19.

Study of Soybean and Cotton Crop Safety and Post-emergence Weed Control Efficacy Using Microencapsulated Acetochlor Formulations of the Invention Formulations 911A, 911B, 914A, 914C, 917A, and 917B (prepared according to the methods described in Examples 16, 17, and 18) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS and DEGREE. The formulations were applied to post-emergent soybean and cotton plants and measured for phytotoxicity 20 DAT. The results are shown in FIG. 30 (Soybean injury) and FIG. 31 (Cotton injury).

Formulations 911A, 911B, 914C, and 917B provided greater soybean safety than DEGREE at the two higher application rates. See FIG. 30. Formulations 914A and 917A were more equivalent to DEGREE in terms of crop safety. HARNESS was most injurious to soybeans; however, this study showed greater cotton injury with DEGREE than with HARNESS. See FIG. 31. This relative response has also been seen under field conditions, where the systemic malformation of newly emerging leaves is more pronounced with DEGREE. Overall cotton injury in this study was fairly low. Formulation 911A showed the greatest cotton safety at all rates. Formulations 917B and 914C were also less injurious than DEGREE at two of three application rates. Release rates were measured in the SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 911A | 137 | 146 |
| 911B | 307 | 320 |
| 914A | 221 | 321 |
| 914C | 96 | 136 |
| 917A | 278 | 329 |
| 917B | 93 | 125 |
| DEGREE | 130 | 202 |

Figure 32:
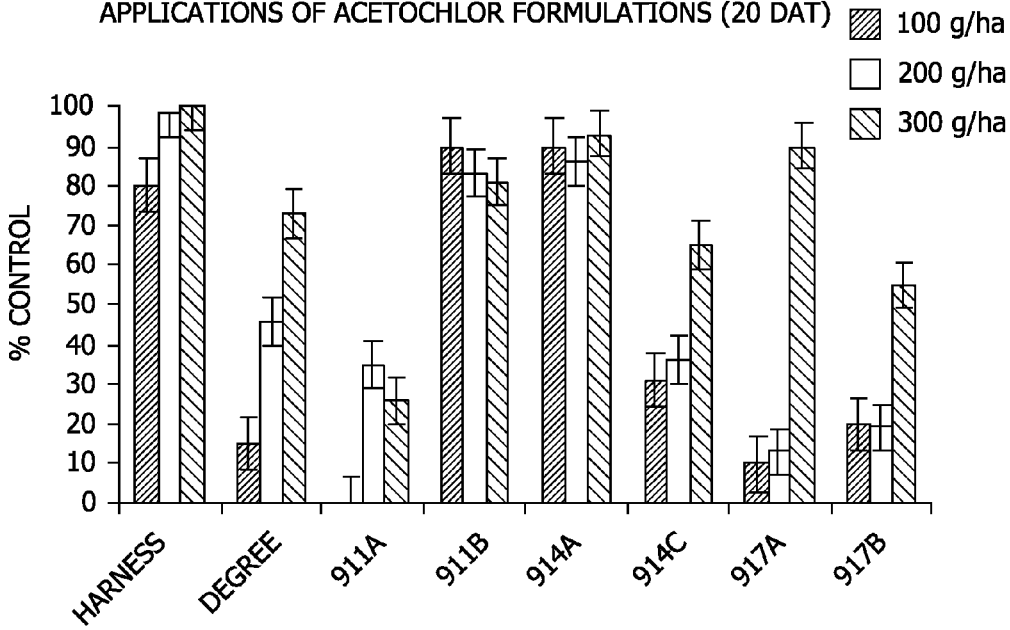
FIG. 32 is a graph depicting control of redroot pigweed achieved with pre-emergent applications of various microencapsulated acetochlor formulations as described in Example 19.
Figure 33:
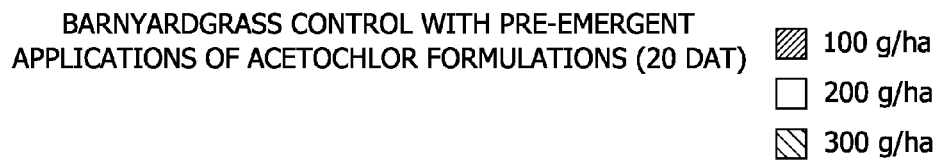
FIG. 33 is a graph depicting control of barnyard grass achieved with pre-emergent applications of various microencapsulated acetochlor formulations as described in Example 19.
Figure 34:
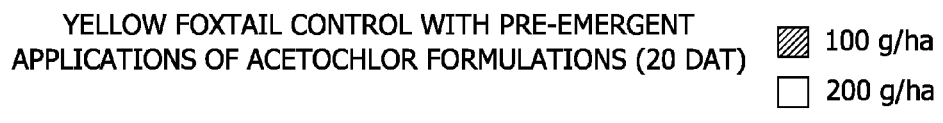
FIG. 34 is a graph depicting control of yellow foxtail achieved with pre-emergent applications of various microencapsulated acetochlor formulations as described in Example 19.

Formulations 911A, 911B, 914A, 914C, 917A, and 917B were also tested for weed control efficacy and compared to the weed control efficacy of both DEGREE and HARNESS. The weed species tested included Redroot pigweed (*Amaranthus retroflexus*), Barnyardgrass (*Echinochloa crusgalli*), and Yellow foxtail (*Setaria lutescens*). The weed control efficacy data are presented in FIGS. 32, 33, and 34.

The weed control efficacy study showed Formulation 911A to be substantially less effective than DEGREE at all application rates. See FIGS. 32, 33, and 34. Formulation 917B was slightly less effective than DEGREE, while Formulation 914C was nearly equivalent. All other formulations were better than or equal to DEGREE.

These data show that increased particle size continues to have the biggest influence on improved crop safety with encapsulated acetochlor formulations. Increasing the level of amine in these formulations did not dramatically impact crop safety, but did show a more significant influence on weed control efficacy.

Example 20

Preparation of Aqueous Dispersions of Microencapsulated Acetochlor

Two aqueous dispersions of microencapsulated acetochlor (designated formulations 934 and 939) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR L. Formulation 939 was prepared with a relatively higher proportion of ISOPAR L solvent compared to formulation 934.

To prepare these formulations, the internal phase, the external phase, the amine solution, and the stabilizer solution were prepared containing the components and amounts shown in the following table:

| Component | Form. 934 Weight of Component (g) | Form. 939 Weight of Component (g) |
|---|---|---|
| Internal Phase | | |
| Acetochlor | 175.50 | 174.20 |
| ISOPAR L | 9.10 | 18.20 |
| MISTAFLEX H9915 | 13.06 | 13.70 |
| External Phase | | |
| Glycerin | 32.0 | 30.00 |
| SOKALAN CP9 | 9.57 | 8.90 |
| Ammonium Caseinate | 0.20 | 0.18 |
| Acid | 0.75 | 0.75 |
| Water | 116.0 | 108 |
| TETA, 50% solution | 5.79 | 6.08 |
| Stabilizer | | |
| Invalon | 23.65 | 23.65 |
| Kelzan CC | 0.21 | 0.21 |
| Antifoam | 0 | 0 |
| Glycerin | 15.85 | 15.85 |
| Proxel GXL | 0.21 | 0.21 |
| Caustic | 0.07 | 0.07 |
| Buffer | 0.47 | 0.47 |

The aqueous dispersions of microcapsules were prepared substantially as described above in Example 1. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 934 | 10.69 | 8.33 |
| 939 | 9.75 | 5.96 |

Example 21

Preparation of Aqueous Dispersions of Microencapsulated Acetochlor

Two aqueous dispersions of microencapsulated acetochlor (designated formulations 936A and 936B) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR L. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 936A Weight of Component (g) | Form. 936B Weight of Component (g) |
|---|---|---|
| Internal Phase | | |
| Acetochlor | 352.70 | |
| ISOPAR L | 18.40 | |
| MISTAFLEX H9915 | 26.40 | |
| External Phase | | |
| Glycerin | 64.70 | |
| SOKALAN CP9 | 19.10 | |
| Ammonium Caseinate | 0.38 | |
| Acid | 1.42 | |
| Water | 233.3 | |
| TETA, 50% solution | 5.79 | 5.79 |
| Stabilizer | | |
| Invalon | 47.89 | |
| Kelzan CC | 0.43 | |
| Antifoam | 0.01 | |
| Glycerin | 32.10 | |
| Proxel GXL | 0.43 | |
| Caustic | 0.15 | |
| Buffer | 0.96 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 936A | 10.16 | 6.34 |
| 936B | 8.36 | 5.46 |

Example 22

Preparation of Aqueous Dispersions of Microencapsulated Acetochlor

Three aqueous dispersions of microencapsulated acetochlor (designated formulations 941A, 941B, and 941C) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR V. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 941A | Form. 941B | Form. 941C |
|---|---|---|---|
| | Weight of Component (g) | | |
| Internal Phase | | | |
| Acetochlor | | 529.0 | |
| ISOPAR V | | 55.30 | |
| MISTAFLEX H9915 | | 41.6 | |
| External Phase | | | |
| Glycerin | | 90.90 | |
| SOKALAN CP9 | | 26.80 | |
| Ammonium Caseinate | | 0.54 | |
| Acid | | 2.09 | |
| Water | | 327.60 | |
| TETA, 50% solution | 6.09 | 6.10 | 6.10 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| Particle Size Parameters | | |
|---|---|---|
| Formulations | Mean Particle size (μm) | Standard Deviation (μm) |
| 941A | 8.90 | 5.56 |
| 941B | 11.67 | 6.76 |
| 941C | 10.98 | 6.52 |

Example 23

Preparation of Aqueous Dispersions of Microencapsulated Acetochlor

Three aqueous dispersions of microencapsulated acetochlor (designated formulations 945A, 945B, and 945C) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR V, and in this Example, the relative proportion of ISOPAR V was halved compared to Example 22. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Forms. 945A, 945B, 945C Weight of Component (g) |
|---|---|
| Internal Phase | |
| Acetochlor | 529.0 |
| ISOPAR V | 27.65 |
| MISTAFLEX H9915 | 39.60 |
| External Phase | |
| Glycerin | 97.1 |
| SOKALAN CP9 | 28.7 |
| Ammonium Caseinate | 0.57 |
| Acid | 2.25 |
| Water | 350 |
| TETA, 50% solution | 17.6 |
| Stabilizer | |
| Invalon | 71.83 |
| Kelzan CC | 0.64 |
| Antifoam | 0.01 |
| Glycerin | 48.15 |
| Proxel GXL | 0.64 |
| Caustic | 0.22 |
| Buffer | 1.43 |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

| Particle Size Parameters | | |
|---|---|---|
| Formulations | Mean Particle size (μm) | Standard Deviation (μm) |
| 945A | 9.72 | 6.02 |
| 945B | 13.22 | 8.23 |
| 945C | 12.48 | 7.84 |

Example 24

Preparation of Aqueous Dispersions of Microencapsulated Acetochlor

An aqueous dispersion of microencapsulated acetochlor (designated formulation 949) was prepared. Formulation 949 was prepared using MISTAFLEX and TETA amine at molar equivalents ratios of amine molar equivalents to isocyanate molar equivalents of approximately 1.05:1. Additionally, the internal solvent was changed from NORPAR 15 to Exxsol D-130, and a relatively small proportion of Exxsol D-130 was used.

To prepare the formulation, the internal phase, the external phase, the amine solution, and the stabilizer solution were prepared containing the components and amounts shown in the following table:

| Component | Weight of Component (g) |
|---|---|
| Internal Phase | |
| Acetochlor | 174.25 |
| Exxsol D-130 | 9.1 |
| MISTAFLEX H9915 | 13.1 |
| External Phase | |
| Glycerin | 32.0 |
| SOKALAN CP9 | 9.5 |
| Ammonium Caseinate | 0.2 |
| Acid | 0.75 |
| Water | 115.3 |
| TETA, 50% solution | 5.8 |
| Stabilizer | |
| Invalon | 23.65 |
| Kelzan CC | 0.21 |
| Antifoam | 0 |
| Glycerin | 15.85 |
| Proxel GXL | 0.21 |
| Caustic | 0.07 |
| Buffer | 0.47 |

The aqueous dispersion of microcapsules was prepared substantially as described above in Example 1 and had a mean particle size of 10.59 μm and a standard deviation of 6.45 μm.

Example 25

Preparation of Aqueous Dispersions of Microencapsulated Acetochlor

Two aqueous dispersions of microencapsulated acetochlor (designated formulations 951A and 951B) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR V, and in this Example, the relative proportion of ISOPAR V was halved compared to Example 22. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 951A and 951B Weight of Component (g) |
|---|---|
| Internal Phase | |
| Acetochlor | 352.70 |
| ISOPAR V | 18.42 |
| MISTAFLEX H9915 | 26.40 |
| External Phase | |
| Glycerin | 64.70 |
| SOKALAN CP9 | 19.10 |
| Ammonium Caseinate | 0.39 |
| Acid | 1.45 |
| Water | 233.3 |
| TETA, 50% solution | 11.73 |
| Stabilizer | |
| Invalon | 47.89 |
| Kelzan CC | 0.43 |

-continued

| Component | Form. 951A and 951B Weight of Component (g) |
|---|---|
| Antifoam | 0.01 |
| Glycerin | 32.10 |
| Proxel GXL | 0.43 |
| Caustic | 0.15 |
| Buffer | 0.96 |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 951A | 11.28 | 7.53 |
| 951B | 8.30 | 5.48 |

Example 26

Preparation of Aqueous Dispersions of Microencapsulated Acetochlor

Two aqueous dispersions of microencapsulated acetochlor (designated formulations 954A and 954B) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to Exxsol D-130. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Form. 954A and 954B Weight of Component (g) |
|---|---|
| Internal Phase | |
| Acetochlor | 352.7 |
| Exxsol D-130 | 36.85 |
| MISTAFLEX | 27.71 |
| External Phase | |
| Glycerin | 60.80 |
| SOKALAN CP9 | 17.9 |
| Ammonium Caseinate | 0.37 |
| Acid | 1.28 |
| Water | 218.39 |
| TETA, 50% solution | 12.31 |
| Stabilizer | |
| Invalon | 47.89 |
| Kelzan CC | 0.43 |

-continued

| Component | Form. 954A and 954B Weight of Component (g) |
|---|---|
| Antifoam | 0.01 |
| Glycerin | 32.10 |
| Proxel GXL | 0.43 |
| Caustic | 0.15 |
| Buffer | 0.96 |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 954A | 9.83 | 6.04 |
| 954B | 7.7 | |

Example 27

Preparation of Aqueous Dispersions of Microencapsulated Acetochlor

Two aqueous dispersions of microencapsulated acetochlor (designated formulations 957A and 957B) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to ISOPAR L. The mean particle sizes of each the various formulations were controlled varying the mixing speed during emulsification.

To prepare these formulations, large batches of each of the internal phase, the external phase, the amine solution, and the stabilizer solution were prepared containing the components and amounts shown in the following table:

| Component | Forms. 957A and 957B Weight of Component (g) |
|---|---|
| Internal Phase | |
| Acetochlor | 353.0 |
| ISOPAR L | 36.90 |
| MISTAFLEX H9915 | 27.7 |
| External Phase | |
| Glycerin | 60.6 |
| SOKALAN CP9 | 17.9 |
| Ammonium Caseinate | 0.37 |
| Acid | 1.35 |
| Water | 218.40 |
| TETA, 50% solution | 12.31 |
| Stabilizer | |
| Invalon | 47.89 |
| Kelzan CC | 0.43 |

| Component | Forms. 957A and 957B Weight of Component (g) |
|---|---|
| Antifoam | 0.01 |
| Glycerin | 32.10 |
| Proxel GXL | 0.43 |
| Caustic | 0.15 |
| Buffer | 0.96 |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 957A | 10.46 | 6.38 |
| 957B | 8.01 | 5.13 |

Example 28

Preparation of Aqueous Dispersions of Microencapsulated Acetochlor

Two aqueous dispersions of microencapsulated acetochlor (designated formulation 960A and 960B) were prepared. These formulations were prepared using the MISTAFLEX blend comprising DES N3200 and DES W and a single amine, TETA. The molar equivalents ratio of amine molar equivalents to isocyanate molar equivalents was approximately 1.05:1. Additionally, the internal solvent was changed from NORPAR 15 to Exxsol D-130, and a higher proportion of Exxsol D-130 was used compared to Example 22.

To prepare the formulation, large batches of each of the internal phase, the external phase, the amine solution, and the stabilizer solution were prepared containing the components and amounts shown in the following table:

| Component | Form. 960A | Form. 960B |
|---|---|---|
| | Weight of Component (g) | |
| Internal Phase | | |
| Acetochlor | 352.70 | |
| Exxsol D-130 | 36.83 | |
| MISTAFLEX H9915 | 27.70 | |
| External Phase | | |
| Glycerin | 60.6 | |
| SOKALAN CP9 | 17.9 | |
| Ammonium Caseinate | 0.37 | |
| Acid | 1.35 | |
| Water | 218.40 | |
| TETA, 50% solution | 6.10 | 6.09 |
| Stabilizer | | |
| Invalon | 47.89 | |
| Kelzan CC | 0.43 | |

-continued

| Component | Form. 960A | Form. 960B |
|---|---|---|
| | Weight of Component (g) | |
| Antifoam | | 0.01 |
| Glycerin | | 32.10 |
| Proxel GXL | | 0.43 |
| Caustic | | 0.15 |
| Buffer | | 0.96 |

The aqueous dispersions of microcapsules were prepared substantially as described above in Example 1. To prepare each formulation, the large internal phase, external phase, and stabilizer batches were divided into smaller approximately equal weight batches and combined as described in Example 1. Two separate amine solutions were used to initiate polymerization. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 960A | 10.60 | 6.51 |
| 960B | 6.65 | 4.55 |

Example 29

Figure 35:
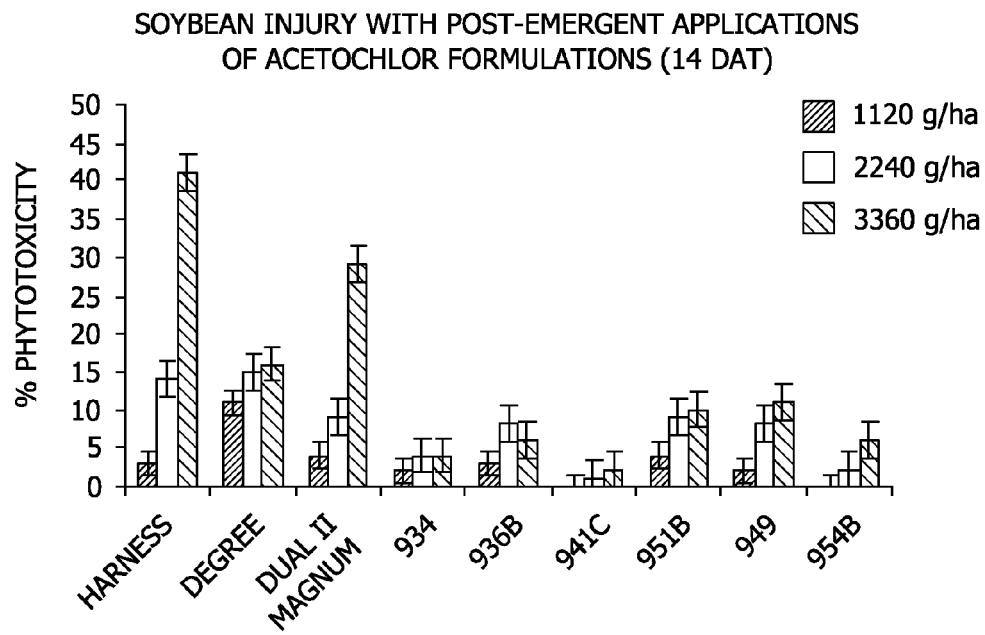
FIG. 35 is a graph depicting soybean injury that occurred with post-emergent applications of various microencapsulated acetochlor formulations as described in Example 29.
Figure 36:
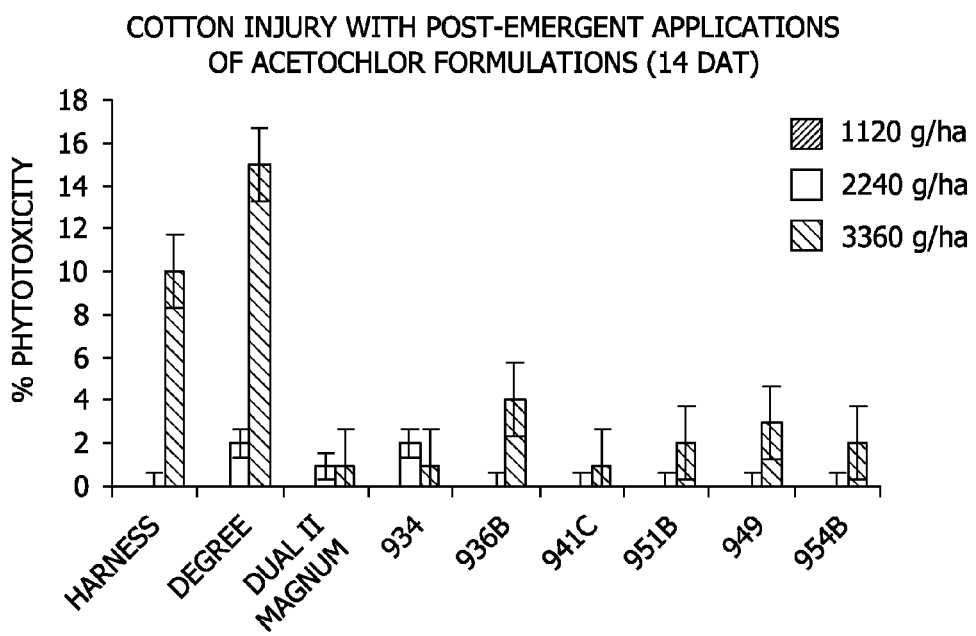
FIG. 36 is a graph depicting cotton injury that occurred with post-emergent applications of various microencapsulated acetochlor formulations as described in Example 29.

Study of Soybean and Cotton Crop Safety and Post-emergence Weed Control Efficacy Using Microencapsulated Acetochlor Formulations of the Invention Formulations 934, 936B, 941C, 951B, and 954B (prepared according to the methods described in Examples 20, 21, 22, 25, and 26) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, and DUAL II MAGNUM. The formulations were applied to post-emergent soybean and cotton plants and measured for phytotoxicity 14 DAT. The results are shown in FIG. 35 (Soybean injury) and FIG. 36 (Cotton injury).

The formulations in this study had increased capsule size compared to DEGREE (capsule size of approximately 3 μm) and different solvents within the capsule (Norpar is used to formulate DEGREE). All formulations provided better soybean safety than DEGREE with formulations 934, 941C, and 954B showing the least amount of injury. See FIG. 35. All formulations also showed less cotton injury than DEGREE, but only at the highest rate tested. See FIG. 36. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 934 | 58 | 73 |
| 936B | 70 | 90 |

-continued

| Formulation | Release at 6 hours (ppm) | Release at 24 hours (ppm) |
|---|---|---|
| 941C | 52 | 63 |
| 951B | 78 | 95 |
| 954B | 54 | 63 |
| DEGREE | 129 | 179 |

Figure 37:
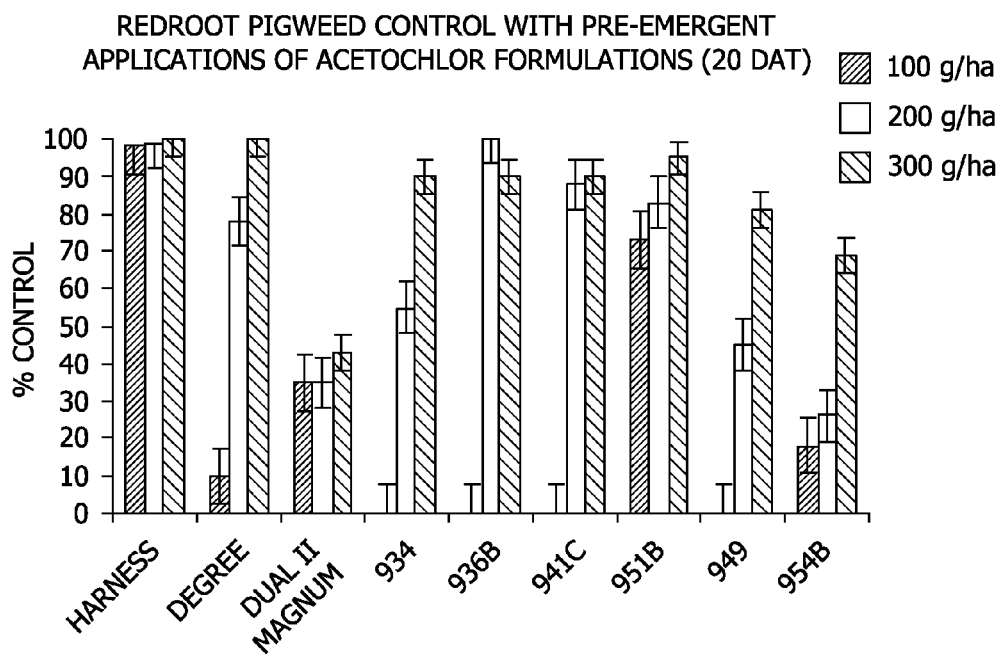
FIG. 37 is a graph depicting control of redroot pigweed achieved with pre-emergent applications of various microencapsulated acetochlor formulations as described in Example 29.
Figure 38:
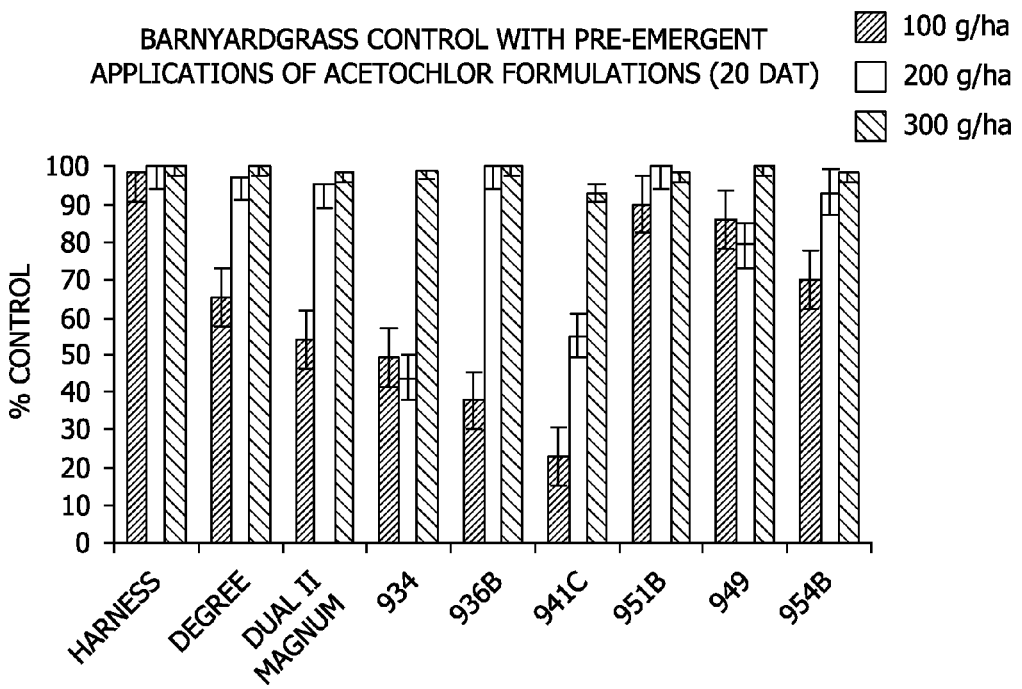
FIG. 38 is a graph depicting control of barnyard grass achieved with pre-emergent applications of various microencapsulated acetochlor formulations as described in Example 29.
Figure 39:
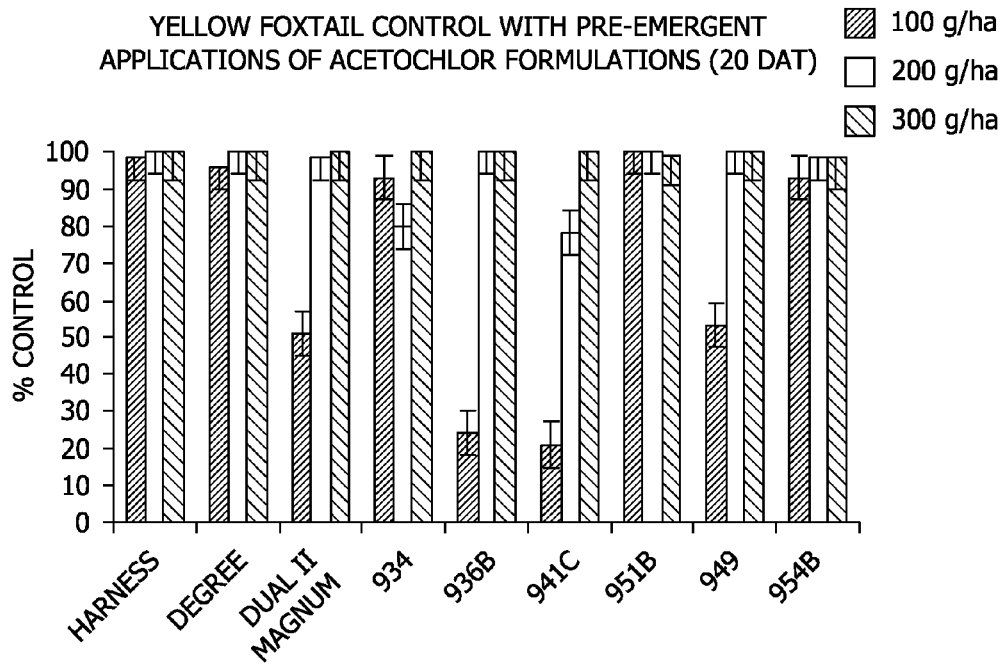
FIG. 39 is a graph depicting control of yellow foxtail achieved with pre-emergent applications of various microencapsulated acetochlor formulations as described in Example 29.

Formulations 934, 936B, 941C, 951B, 949 (formulated as describe above in Example 24), 954B were also tested for weed control efficacy and compared to the weed control efficacy of both DEGREE and HARNESS. The weed species tested included Redroot pigweed (*Amaranthus retroflexus*), Barnyardgrass (*Echinochloa crus-galli*), and Yellow foxtail (*Setaria lutescens*). The weed control efficacy data are presented in FIGS. 37, 38, and 39.

Pre-emergence weed control with these formulations highlighted a number of differences among these formulations. Redroot pigweed control showed formulations 934, 949, and 954B to be less effective than DEGREE at the two higher application rates. See FIG. 37. The remaining formulations provided control that was equivalent or greater than that shown by DEGREE. Note the lack of control with DUAL II MAGNUM. Barnyardgrass, probably the most reliable indicator in this assay, showed weaker control with formulations 934 and 941C at the two lower application rates. See FIG. 38. All other formulations were closely equivalent to DEGREE. Control of yellow foxtail again indicated some weakness with Formulation 941C. See FIG. 39. Weaker control was also seen with formulations 936B and 949 at the lowest rate tested. All formulations were clearly superior to Dual Magnum in the control of redroot pigweed, differences were less apparent versus the grass weed species in this study.

Example 30

Figure 40:
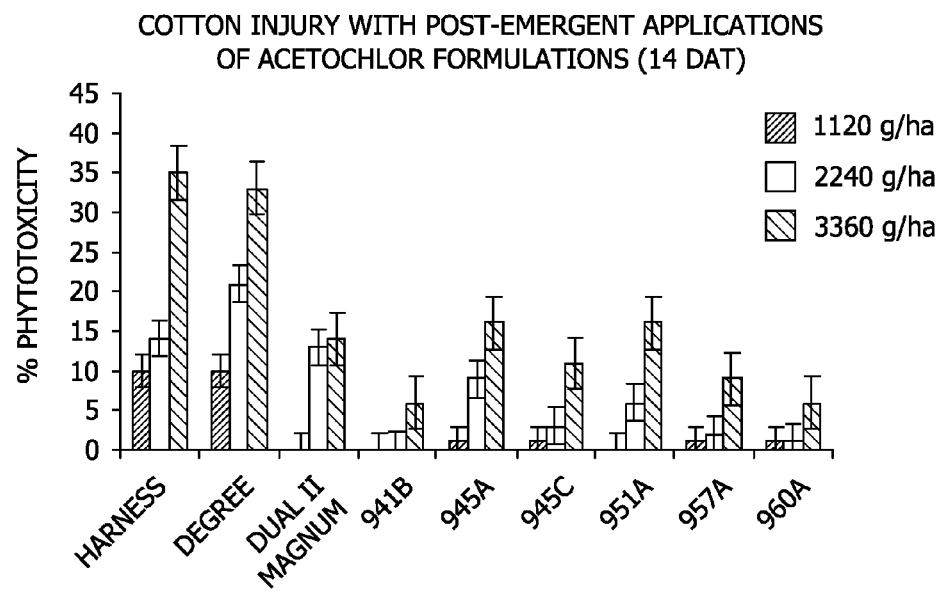
FIG. 40 is a graph depicting cotton injury that occurred with post-emergent applications of various microencapsulated acetochlor formulations as described in Example 30.
Figure 41:
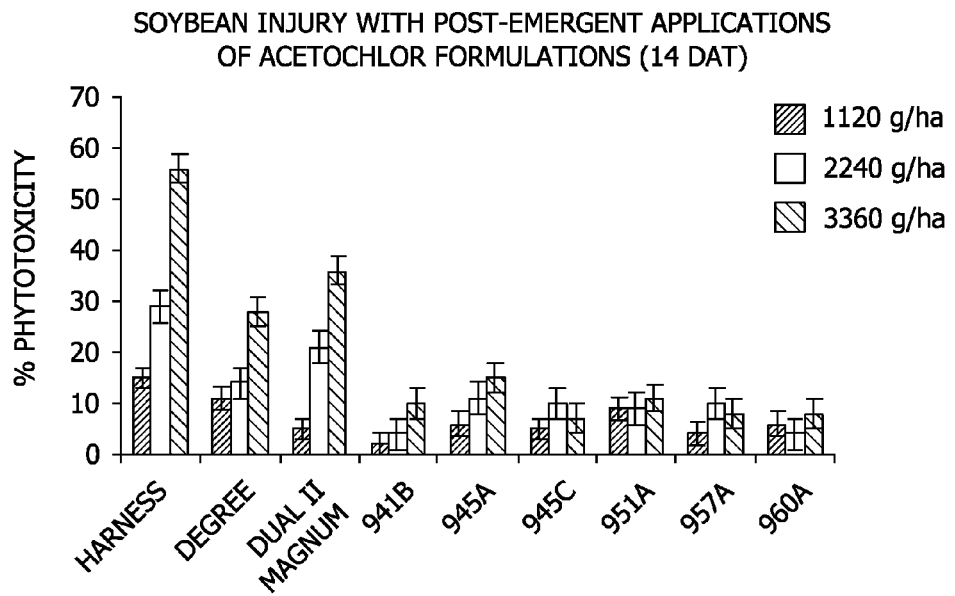
FIG. 41 is a graph depicting soybean injury that occurred with post-emergent applications of various microencapsulated acetochlor formulations as described in Example 30.

Study of Soybean and Cotton Crop Safety and Post-emergence Weed Control Efficacy using Microencapsulated Acetochlor Formulations of the Invention Formulations 941B, 945A, 945C, 951A, 957A, and 960A (prepared according to the methods described in Examples 22, 23, 25, 27, and 28) were applied to glyphosate-tolerante (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, and DUAL II MAGNUM. The formulations were applied to post-emergent soybean and cotton plants and measured for phytotoxicity 14 DAT. The results are shown in FIG. 40 (Cotton injury) and FIG. 41 (Soybean injury).

These formulations again contained larger capsule sizes and different solvents within the capsule. All formulations provided better cotton safety than DEGREE at all application rates. See FIG. 40. The best crop safety was evident with Formulations 941B, 957A, and 960A. Differences were less apparent in soybeans due to less overall injury. See FIG. 41. However, formulations 941B and 960A again showed significantly less injury than DEGREE at all application rates. Release rates were measured in a SOTAX AT-7 dissolution test apparatus according to the method described herein. See the following table for the release rate of formulation 960A and of DEGREE.

| Formulation | Release at 6 hours (ppm) | Release at 24 hours (ppm) |
|---|---|---|
| 960A | 52 | 64 |
| DEGREE | 129 | 179 |

Figure 42:
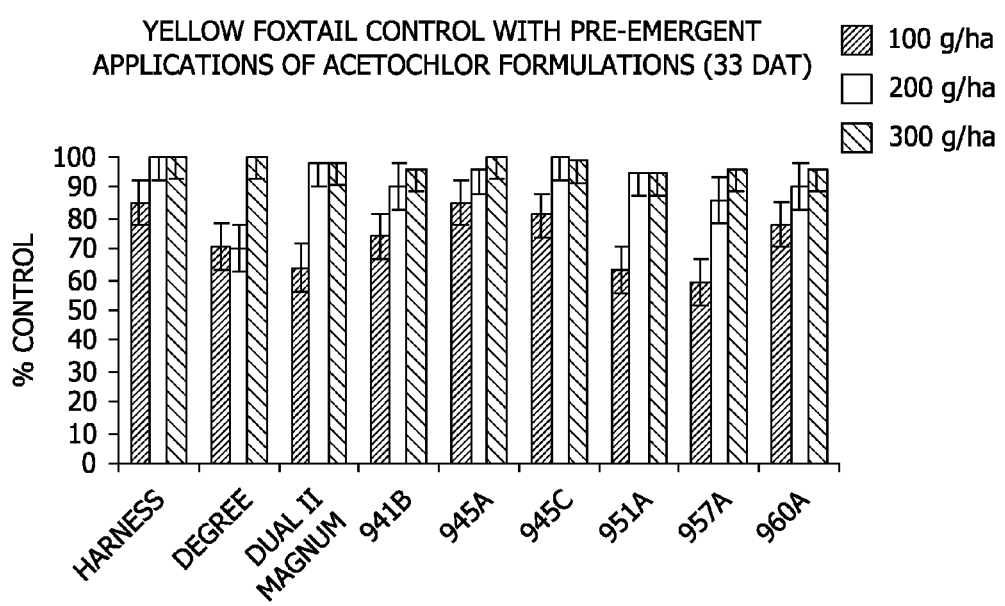
FIG. 42 is a graph depicting control of yellow foxtail achieved with pre-emergent applications of various microencapsulated acetochlor formulations as described in Example 30.
Figure 43:
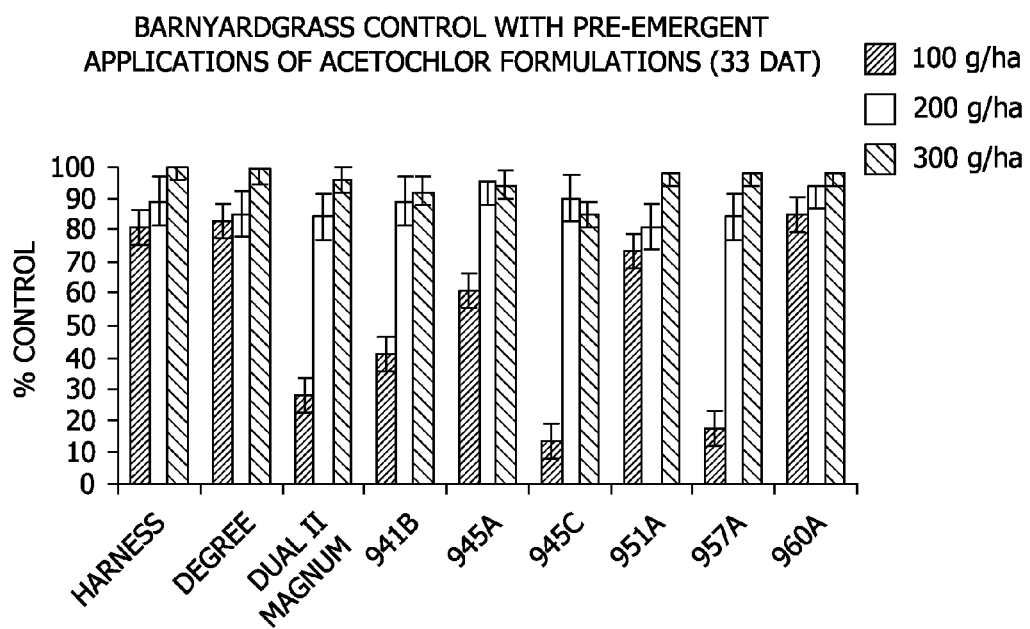
FIG. 43 is a graph depicting control of barnyard grass achieved with pre-emergent applications of various microencapsulated acetochlor formulations as described in Example 30.
Figure 44:
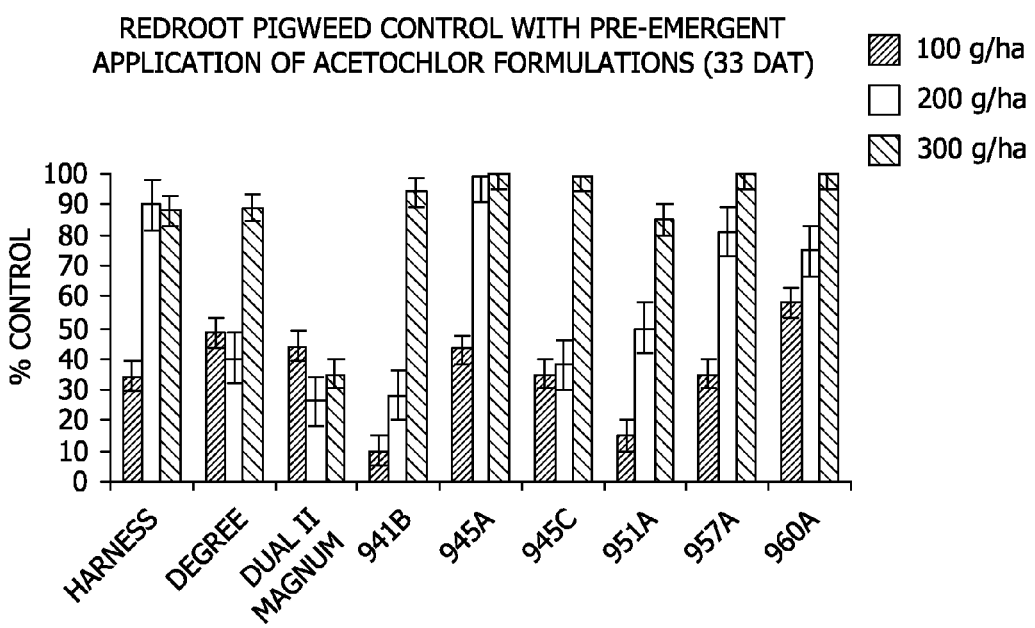
FIG. 44 is a graph depicting control of redroot pigweed achieved with pre-emergent applications of various microencapsulated acetochlor formulations as described in Example 30.

Formulations 941B, 945A, 945C, 951A, 957A, and 980A were also tested for weed control efficacy and compared to the weed control efficacy of both DEGREE and HARNESS. The weed species tested included Redroot pigweed (*Amaranthus retroflexus*), Barnyardgrass (*Echinochloa crusgalli*), and Yellow foxtail (*Setaria lutescens*). The weed control efficacy data are presented in FIGS. 42, 43, and 44. All experimental formulations in this study provided more complete control of yellow foxtail across all application rates. See FIG. 42. Relative to barnyardgrass, only formulations 951A and 960A gave control equivalent to DEGREE at all rates. See FIG. 43. Control of redroot pigweed was greater than DEGREE with formulations 954A, 957A, and 960A. See FIG. 44. All others were essentially equivalent.

Example 31

Figure 45:
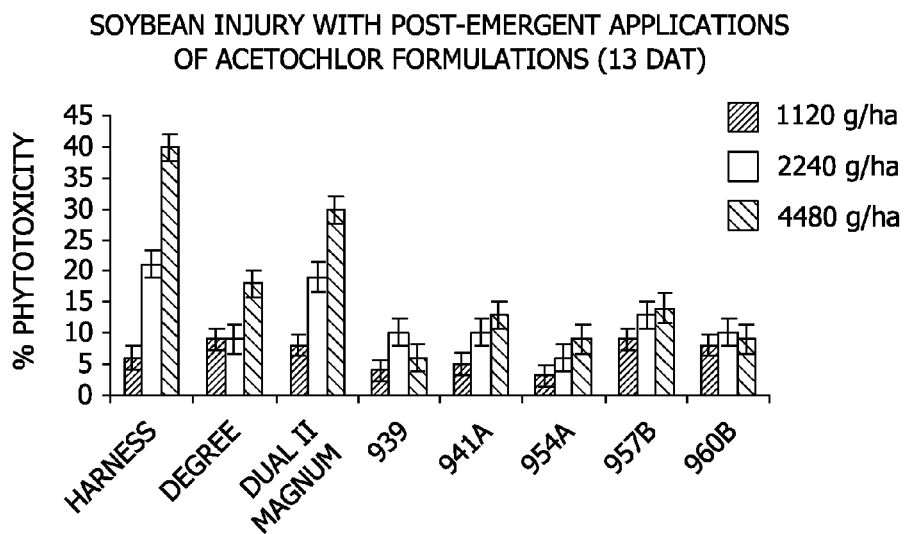
FIG. 45 is a graph depicting soybean injury that occurred with post-emergent applications of various microencapsulated acetochlor formulations as described in Example 31.
Figure 46:
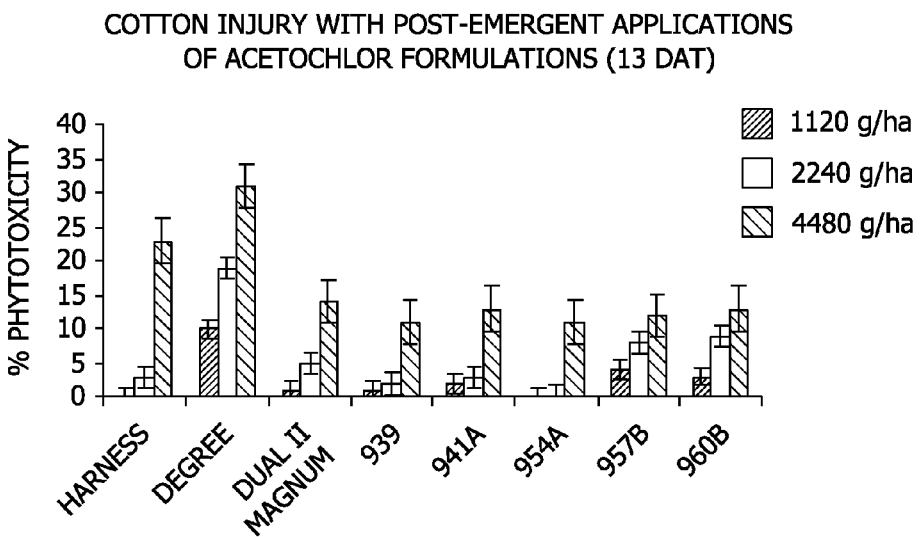
FIG. 46 is a graph depicting cotton injury that occurred with post-emergent applications of various microencapsulated acetochlor formulations as described in Example 31.
Figure 47:
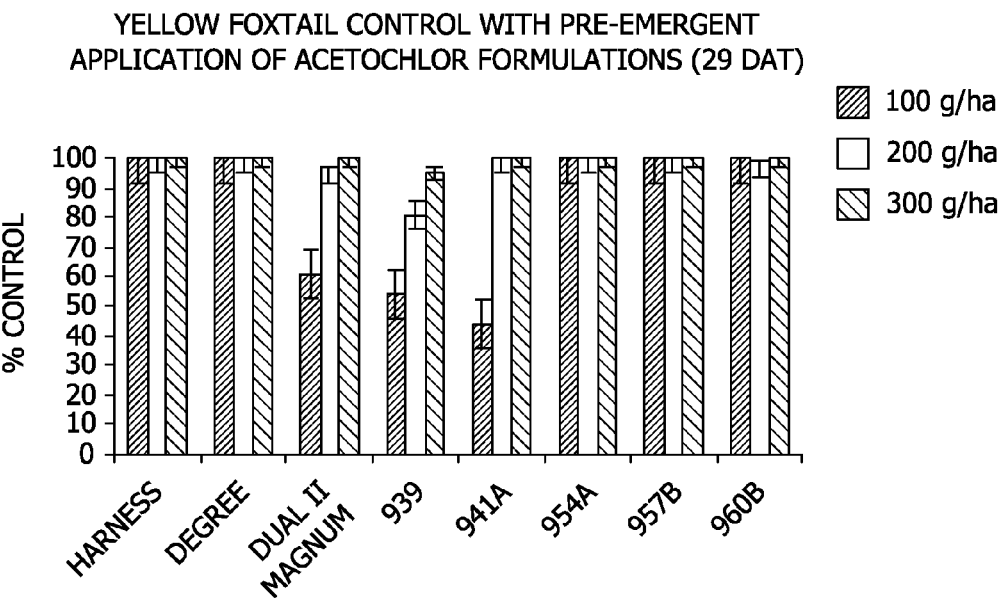
FIG. 47 is a graph depicting control of yellow foxtail achieved with pre-emergent applications of various microencapsulated acetochlor formulations as described in Example 31.
Figure 48:
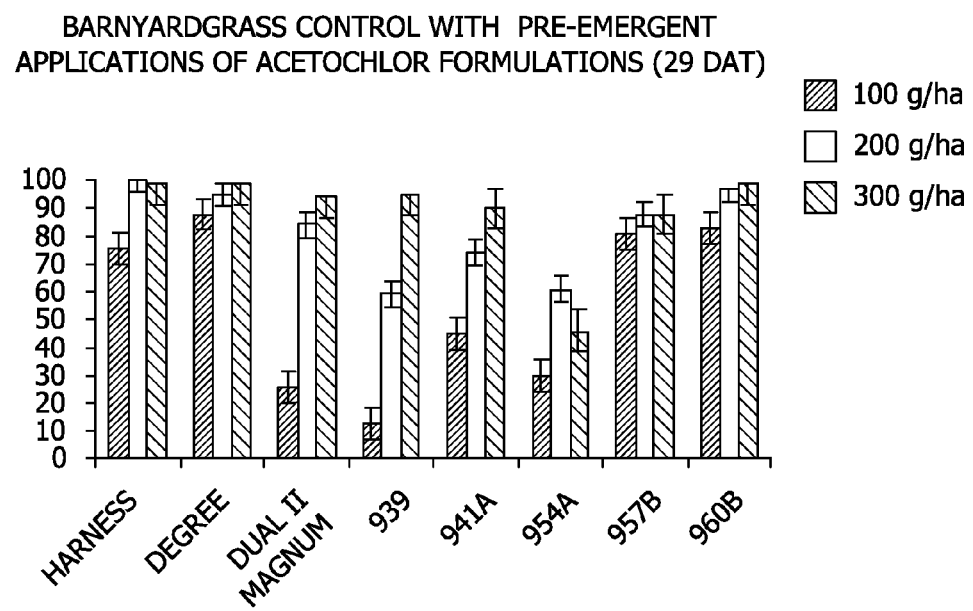
FIG. 48 is a graph depicting control of barnyard grass achieved with pre-emergent applications of various microencapsulated acetochlor formulations as described in Example 31.
Figure 49:
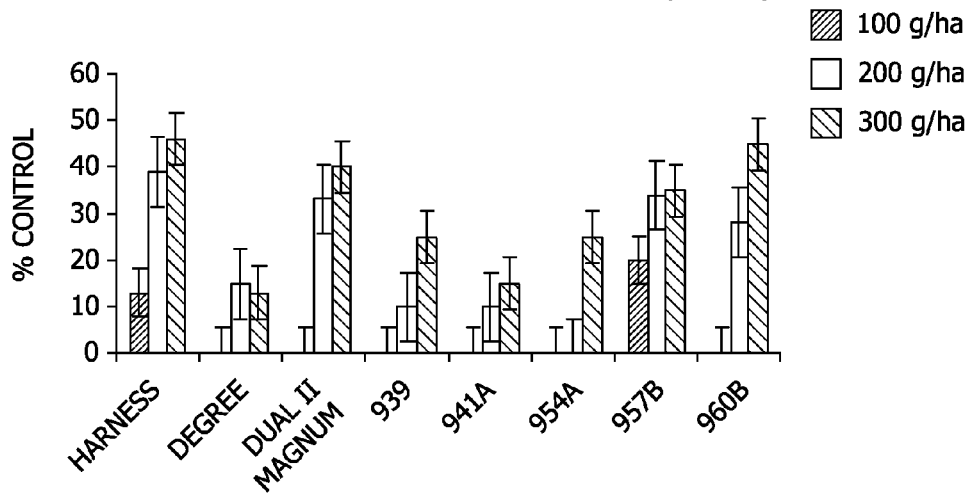
FIG. 49 is a graph depicting control of common purslane achieved with pre-emergent applications of various microencapsulated acetochlor formulations as described in Example 31.
Figure 50:
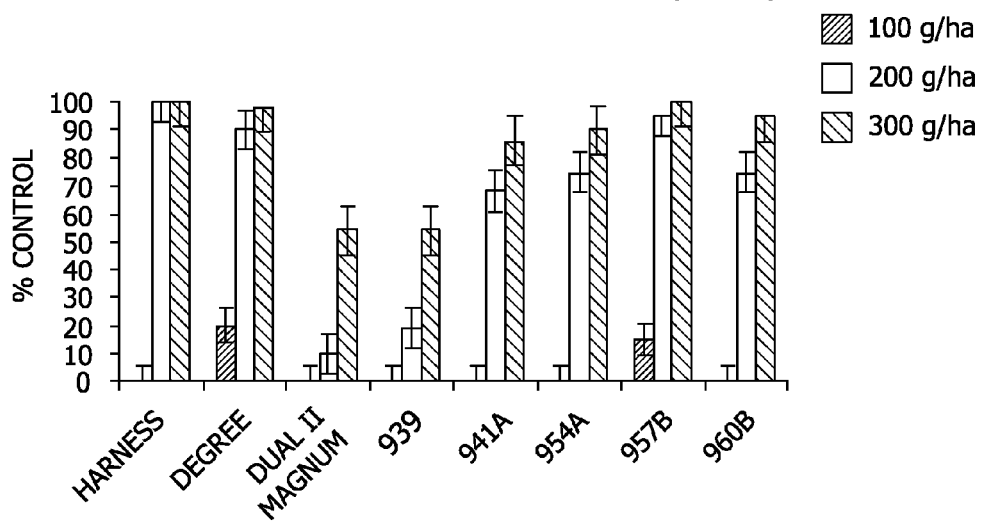
FIG. 50 is a graph depicting control of redroot pigweed achieved with pre-emergent applications of various microencapsulated acetochlor formulations as described in Example 31.

Study of Soybean and Cotton Crop Safety and Post-emergence Weed Control Efficacy using Microencapsulated Acetochlor Formulations of the Invention Formulations 939, 941A, 954A, 957B and 960B (prepared according to the methods described in Examples 20, 22, 26, 27, and 28) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, and DUAL II MAGNUM. The formulations were applied to post-emergent soybean and cotton plants and measured for phytotoxicity 13 DAT. The results are shown in FIG. 45 (soybean injury) and FIG. 46 (cotton injury). Formulations 957B and 960B were both slightly less injurious than DEGREE versus soybeans and significantly less injurious versus cotton at all rates. See FIGS. 45 and 46. All other formulations were also less injurious than DEGREE, but lacked sufficient efficacy to be of further interest. See below. Release rates were measured in a SOTAX AT-7 dissolution test apparatus according to the method described herein. See the following table for the release rates of some of the tested formulations.

| Formulation | Release at 6 hours (ppm) | Release at 24 hours (ppm) |
|---|---|---|
| 941A | 56 | 64 |
| 954A | 53 | 64 |
| 957B | 68 | 87 |
| 960B | 70 | 86 |
| DEGREE | 129 | 179 |

Formulations 939, 941A, 954A, 957B and 960B were also tested for weed control efficacy and compared to the weed control efficacy of DEGREE, HARNESS, and DUAL II MAGNUM. The weed species tested included Redroot pigweed (*Amaranthus retroflexus*), Barnyardgrass (*Echinochloa crus-galli*), Yellow foxtail (*Setaria lutescens*), and Purslane. The weed control efficacy data are presented in FIGS. 47 through 50. Pre-emergence weed control with these experimental formulations showed 957B and 960B to have efficacy equal to or better than that of DEGREE across all species. See FIGS. 47 through 50.

Example 32

Figure 51:
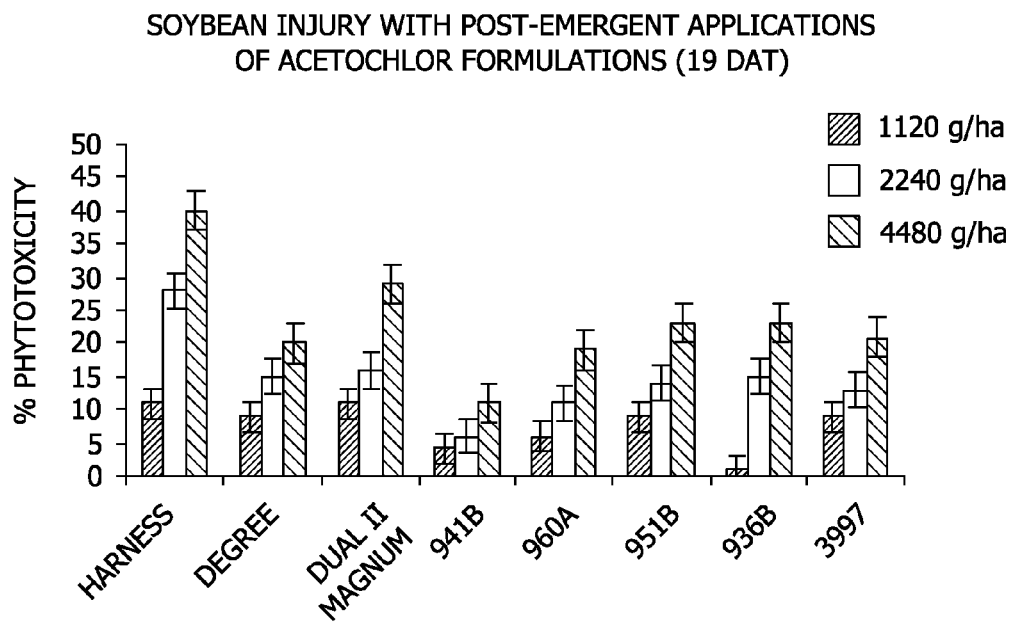
FIG. 51 is a graph depicting soybean injury that occurred with post-emergent applications of various microencapsulated acetochlor formulations as described in Example 32.
Figure 52:
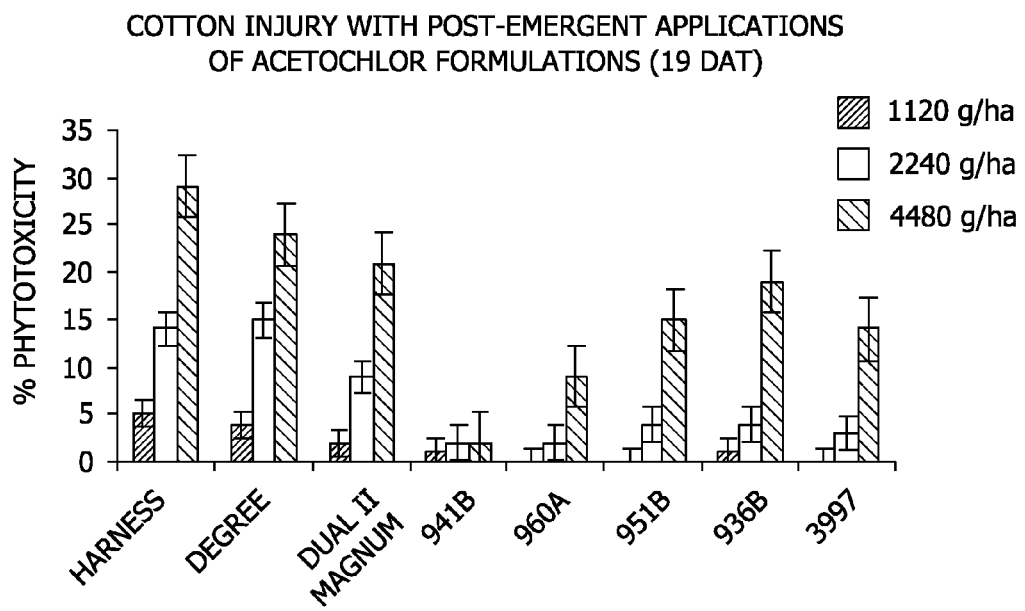
FIG. 52 is a graph depicting cotton injury that occurred with post-emergent applications of various microencapsulated acetochlor formulations as described in Example 32.
Figure 53:
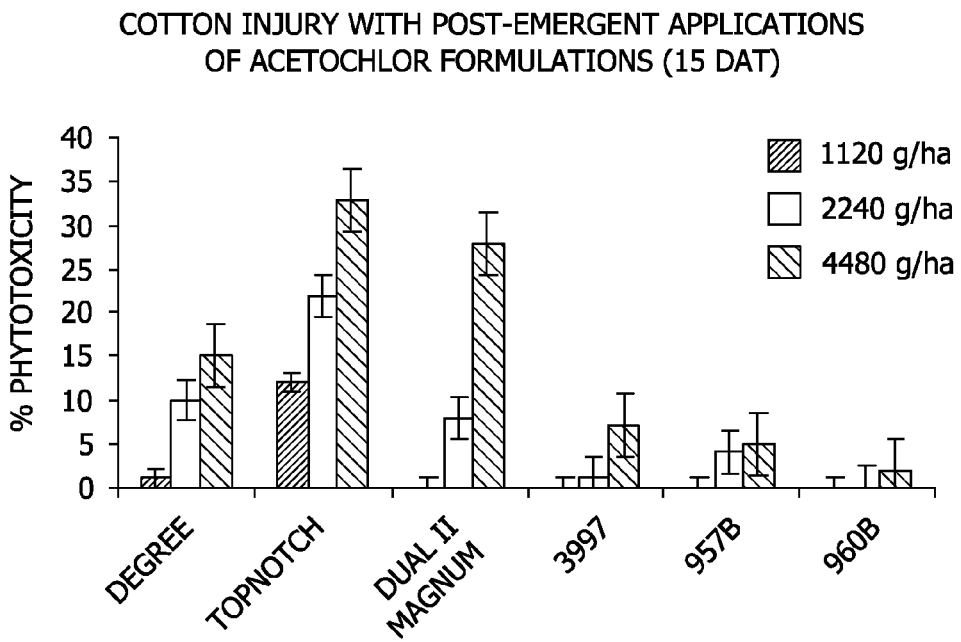
FIG. 53 is a graph depicting cotton injury that occurred with post-emergent applications of various microencapsulated acetochlor formulations as described in Example 32.
Figure 54:
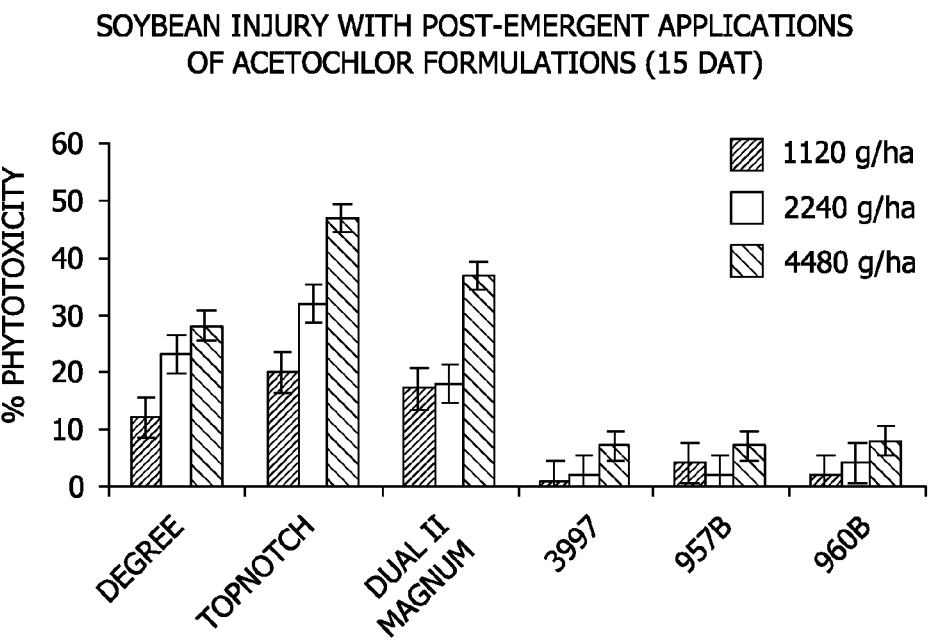
FIG. 54 is a graph depicting soybean injury that occurred with post-emergent applications of various microencapsulated acetochlor formulations as described in Example 32.
Figure 55:
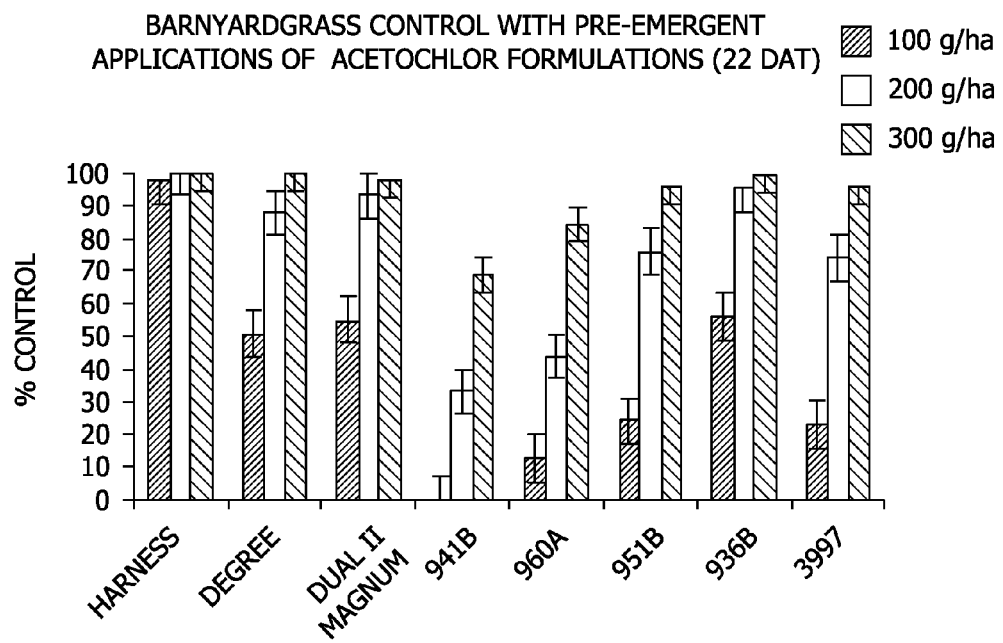
FIG. 55 is a graph depicting control of barnyard grass achieved with pre-emergent applications of various microencapsulated acetochlor formulations as described in Example 32.
Figure 56:
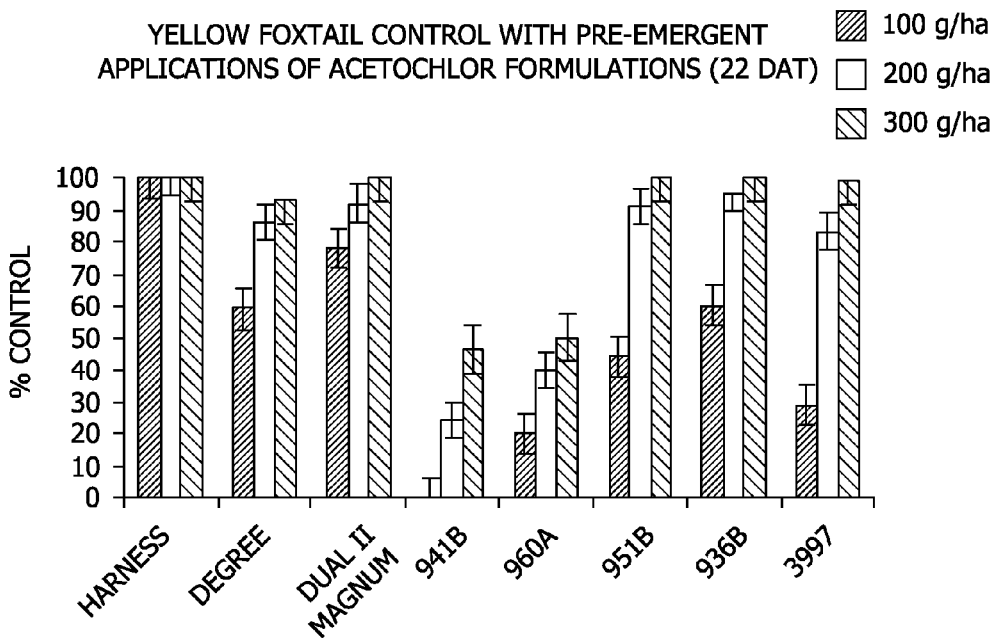
FIG. 56 is a graph depicting control of yellow foxtail achieved with pre-emergent applications of various microencapsulated acetochlor formulations as described in Example 32.

Study of Soybean and Cotton Crop Safety and Post-emergence Weed Control Efficacy using Microencapsulated Acetochlor Formulations of the Invention Formulations 936B, 941B, 951B, 957B, 960A, and 960B (prepared according to the methods described in Examples 21, 22, 25, 27, and 28) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, DUAL II MAGNUM, and TOPNOTCH, available from Dow AgroSciences. TOPNOTCH contains 33.7% acetochlor and 66.3% proprietary ingredients, including dichlormid. The formulations were applied to post-emergent soybean and cotton plants and measured for phytotoxicity. The results are shown in FIG. 51 (soybean injury 19 DAT), FIG. 52 (cotton injury 19 DAT), FIG. 53 (cotton injury 15 DAT), and FIG. 54 (soybean injury 15 DAT).

Formulations 936B, 941B, 951B, and 960A were evaluated against HARNESS, DEGREE, DUAL II MAGNUM, and formulation 3997 (prepared according to the method described in Example 3). The best crop safety among formulations 936B, 941B, 951B, and 960A in this study was seen with formulation 941B. See FIGS. 51 and 52. This formulation showed significantly better cotton and soybean safety than DEGREE at all application rates. Formulations 936B, 951B, and 960A were generally equivalent to formulation 3997. They showed similar soybean injury to that observed with DEGREE, but were significantly safer at all rates in cotton. The one exception was Formulation 936B, which was similar to DEGREE in cotton at the high application rate. Release rates were measured in a SOTAX AT-7 dissolution test apparatus according to the method described herein. See the following table for the release rates of some of the tested formulations.

| Formulation | Release at 6 hours (ppm) | Release at 24 hours (ppm) |
|---|---|---|
| 936B | 70 | 90 |
| 951B | 78 | 95 |
| 960A | 52 | 64 |
| 960B | 70 | 86 |
| DEGREE | 129 | 179 |

Formulations 957B and 960B were evaluated in this study versus DEGREE, DUAL II MAGNUM, TOPNOTCH, and formulation 3997. Both formulations showed soybean and cotton safety that was equivalent to that seen with formulation 3997. See FIGS. 53 and 54. All three of these formulations were substantially safer than the commercial standards. TOPNOTCH proved to be the most injurious formulation.

Formulations 936B, 941B, 951B, 957B, 960A, and 960B were also tested for weed control efficacy and compared to the weed control efficacy of DEGREE, HARNESS, DUAL II MAGNUM, and formulation 3997. The weed species tested included Redroot pigweed (*Amaranthus retroflexus*), Barnyardgrass (*Echinochloa crus-galli*), Yellow foxtail (*Setaria lutescens*), and Purslane (*Portulaca oleracea*). The weed control efficacy data are presented in FIGS. 53 through 56.

Formulations 941B and 960A were both substantially less effective in controlling barnyardgrass and yellow foxtail than the commercial standards. See FIGS. 53 and 54. Formulations 951B and 936B were better than or equal to formulation 3997 in weed control efficacy. Among these three the best weed control was obtained with Formulation 936B.

Example 33

Figure 57:
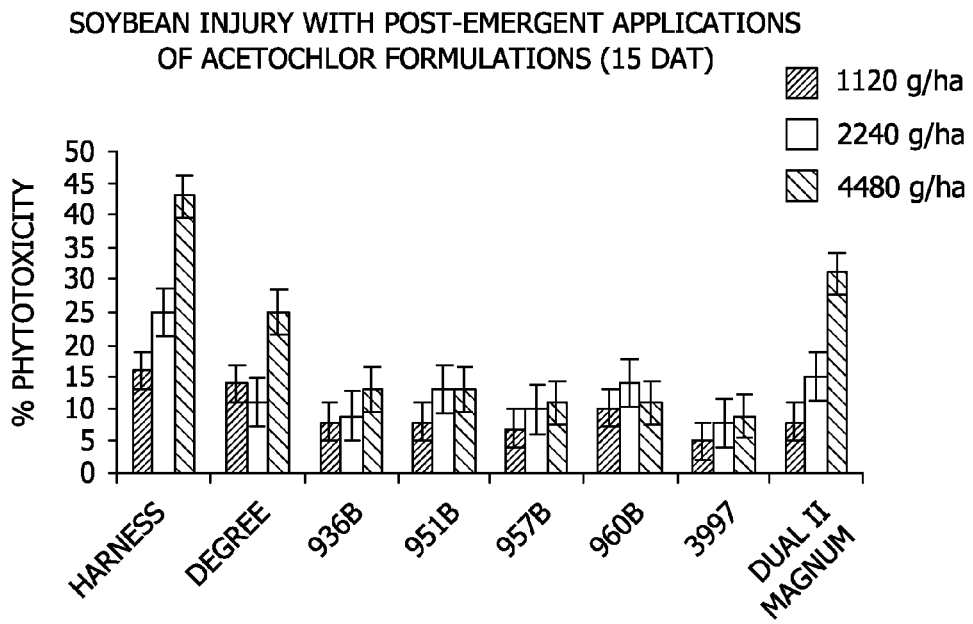
FIG. 57 is a graph depicting soybean injury that occurred with post-emergent applications of various microencapsulated acetochlor formulations as described in Example 33.
Figure 58:
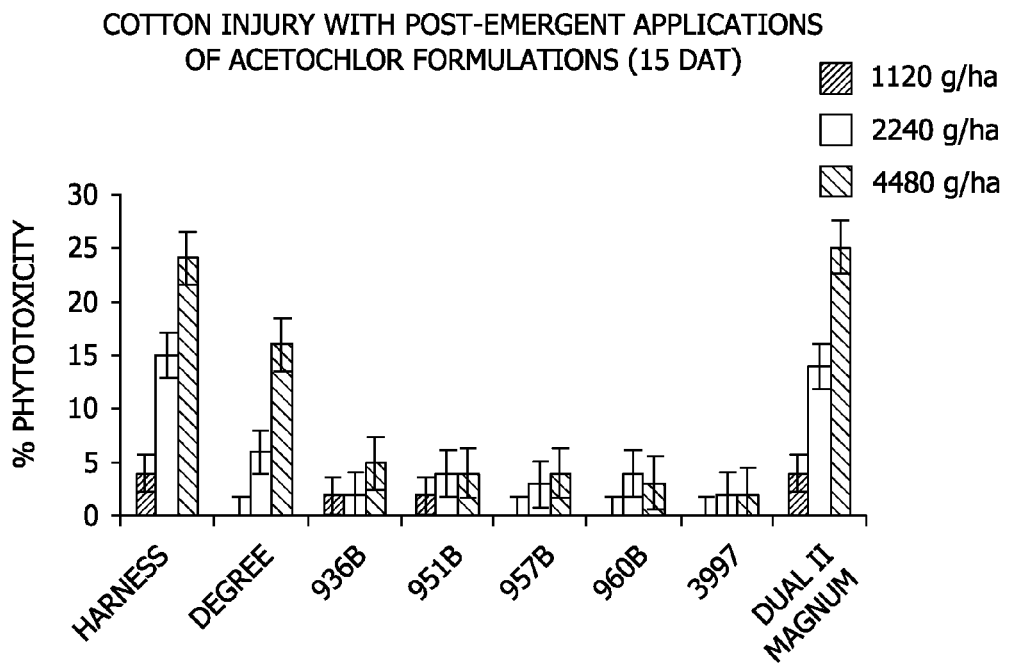
FIG. 58 is a graph depicting cotton injury that occurred with post-emergent applications of various microencapsulated acetochlor formulations as described in Example 33.

Study of Soybean and Cotton Crop Safety and Post-emergence Weed Control Efficacy using Microencapsulated Acetochlor Formulations of the Invention Formulations 957B, 960B, 951B, and 936B (prepared according to the methods described in Examples 21, 25, 27, and 28) were applied to glyphosate-tolerant (ROUNDUP READY) soybean (AG 4403) and glyphosate-tolerant (ROUNDUP READY) cotton (RR Flex—short to midseason variety) crops under greenhouse conditions. These formulations were tested against commercial formulations HARNESS, DEGREE, and DUAL II MAGNUM and against formulation 3997 (prepared as described in Example 3). The formulations were applied to post-emergent soybean and cotton plants and measured for phytotoxicity 15 DAT. The results are shown in FIG. 57 (soybean injury) and FIG. 58 (cotton injury).

Post-emergence soybean injury showed all four experimental formulations to be equivalent to formulation 3997. See FIG. 57. These showed significantly better crop safety than DEGREE and DUAL II MAGNUM at the high rate and HARNESS at all application rates. Cotton injury for the experimental formulations was similar to that of formulation 3997 and significantly better than HARNESS and DUAL II MAGNUM at the two highest rates and DEGREE at the highest rate. See FIG. 58. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 957B | 68 | 87 |
| 960B | 70 | 86 |
| 951B | 78 | 95 |
| 936B | 70 | 90 |
| DEGREE | 129 | 179 |

Figure 59:
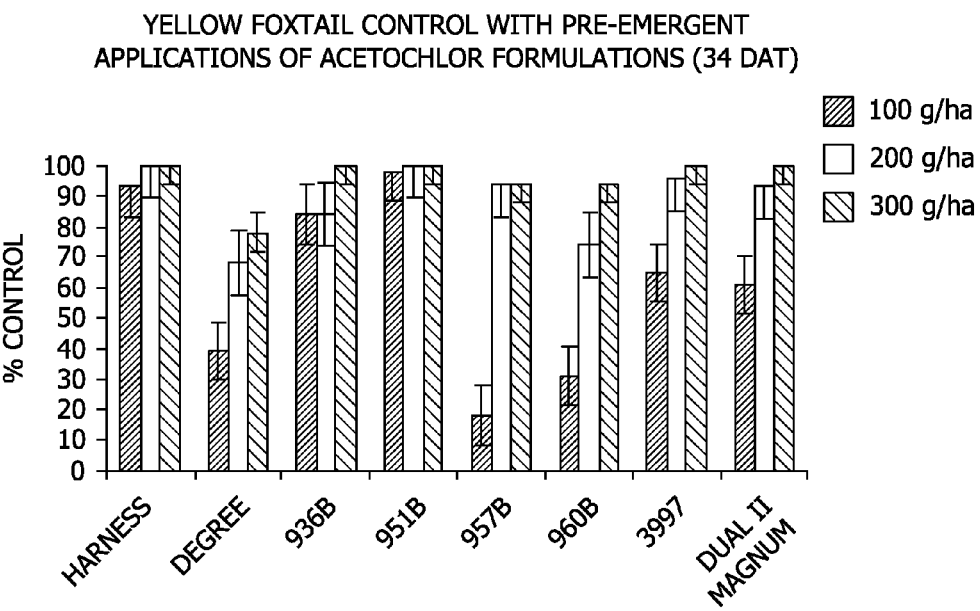
FIG. 59 is a graph depicting control of yellow foxtail achieved with pre-emergent applications of various microencapsulated acetochlor formulations as described in Example 33.
Figure 60:
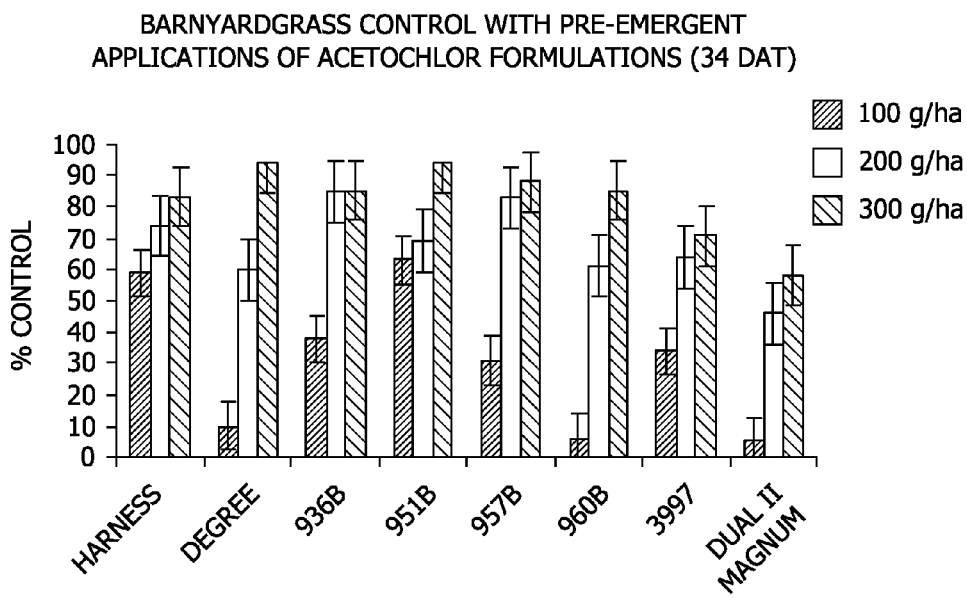
FIG. 60 is a graph depicting control of barnyard grass achieved with pre-emergent applications of various microencapsulated acetochlor formulations as described in Example 33.
Figure 61:
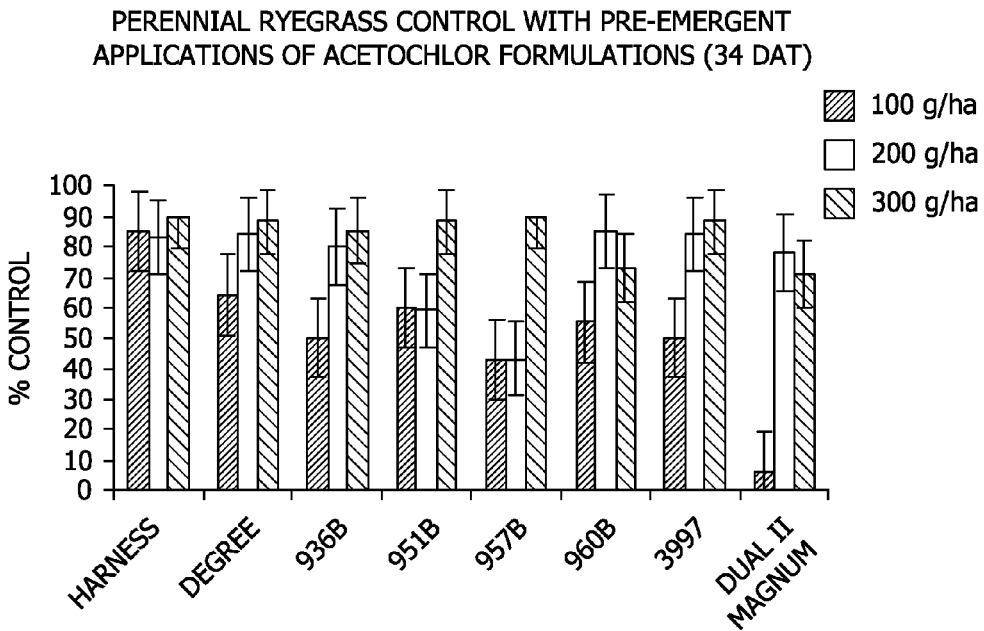
FIG. 61 is a graph depicting control of perennial ryegrass achieved with pre-emergent applications of various microencapsulated acetochlor formulations as described in Example 33.

Formulations 957B, 960B, 951B, and 936B were also tested for weed control efficacy and compared to the weed control efficacy of DEGREE, HARNESS, and DUAL II MAGNUM. The weed species tested included Barnyardgrass (*Echinochloa crus-galli*), Yellow foxtail (*Setaria lutescens*), and Annual ryegrass (*Lolium multiflorum*). The weed control efficacy data are presented in FIGS. 59 through 61.

Formulations 936B and 951B consistently provided the best weed control efficacy across species among the experimental formulations. Relative to yellow foxtail these two formulations gave control that was equal to HARNESS, better than DEGREE, and marginally better than formulation 3997 and DUAL II MAGNUM. See FIG. 59. Formulations 957B and 960B were both equal to formulation 3997 at higher rates, but were weaker at the lowest rate. Formulations 936B, 951B, and 957B were equal to or better than the standards at most application rates in the control of barnyardgrass. See FIG. 60. Formulation 960B was less effective. Control of perennial ryegrass showed Formulations 936B, 951B, and 960B to be equal to DEGREE and formulation 3997. See FIG. 59. Formulation 957B in this case was less effective.

Example 34

Preparation of Aqueous Dispersions of Microencapsulated Acetochlor

Three aqueous dispersions of microencapsulated acetochlor (designated formulation 993A, 993B, and 993C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. In these formulations, the acetochlor loading approximately 38% by weight, which is relatively lower than the acetochlor loading in DEGREE.

To prepare the formulation, large batches of each of the internal phase, the external phase, the amine solution, and the stabilizer solution were prepared containing the components and amounts shown in the following table:

| Component | Form. 993A | Form. 993B | Form. 993C |
|---|---|---|---|
| | Weight of Component (g) | | |
| Internal Phase | | | |
| Acetochlor | | 483.0 | |
| NORPAR 15 | | 25.0 | |
| MISTAFLEX H9915 | | 35.20 | |
| External Phase | | | |
| Glycerin | | 108.0 | |
| SOKALAN CP9 | | 31.82 | |
| Ammonium Caseinate | | 0.64 | |
| Acid | | 2.40 | |
| Water | | 389.0 | |
| TETA, 50% solution | 5.90 | 5.87 | 5.86 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 993A | 7.86 | 5.36 |
| 993B | 10.95 | 6.64 |
| 993C | 13.9 | 10.4 |

TABLE

Particle Size Parameters

| Formulations | Mean Particle size (μm) | Standard Deviation (μm) |
|---|---|---|
| 997A | 7.73 | 5.17 |
| 997B | 10.56 | 6.66 |
| 997C | 13.38 | 9.21 |

Example 35

Preparation of Aqueous Dispersions of Microencapsulated Acetochlor

Three aqueous dispersions of microencapsulated acetochlor (designated formulation 997A, 997B, and 997C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. In these formulations, the acetochlor loading approximately 40% by weight, which is relatively lower than the acetochlor loading in DEGREE.

To prepare the formulation, large batches of each of the internal phase, the external phase, the amine solution, and the stabilizer solution were prepared containing the components and amounts shown in the following table:

| Component | Form. 997A | Form. 997B | Form. 997C |
|---|---|---|---|
| | Weight of Component (g) | | |
| Internal Phase | | | |
| Acetochlor | | 508.40 | |
| NORPAR 15 | | 26.30 | |
| MISTAFLEX H9915 | | 37.10 | |
| External Phase | | | |
| Glycerin | | 101.90 | |
| SOKALAN CP9 | | 30.05 | |
| Ammonium Caseinate | | 0.61 | |
| Acid | | 2.25 | |
| Water | | 367.0 | |
| TETA, 50% solution | 6.21 | 6.23 | 6.22 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

Example 36

Preparation of Aqueous Dispersions of Microencapsulated Acetochlor

Three aqueous dispersions of microencapsulated acetochlor (designated formulation 601A, 601B, and 601C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. In these formulations, the acetochlor loading was approximately equal to DEGREE.

To prepare the formulation, large batches of each of the internal phase, the external phase, the amine solution, and the stabilizer solution were prepared containing the components and amounts shown in the following table:

| Component | Form. 601A | Form. 601B | Form. 601C |
|---|---|---|---|
| | Weight of Component (g) | | |
| Internal Phase | | | |
| Acetochlor | | 534.60 | |
| NORPAR 15 | | 27.65 | |
| MISTAFLEX H9915 | | 39.0 | |
| External Phase | | | |
| Glycerin | | 95.66 | |
| SOKALAN CP9 | | 28.22 | |
| Ammonium Caseinate | | 0.58 | |
| Acid | | 2.25 | |
| Water | | 345.0 | |
| TETA, 50% solution | 6.54 | 6.53 | 6.54 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 601A | 8.13 | 5.23 |
| 601B | 11.08 | 7.44 |
| 601C | 14.64 | 10.46 |

Example 37

Figure 62:
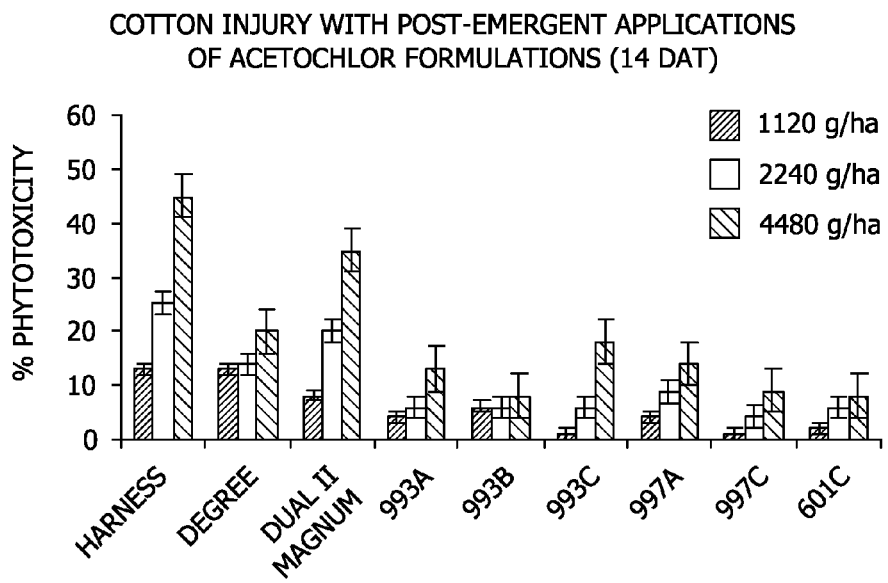
FIG. 62 is a graph depicting cotton injury that occurred with post-emergent applications of various microencapsulated acetochlor formulations as described in Example 37.
Figure 63:
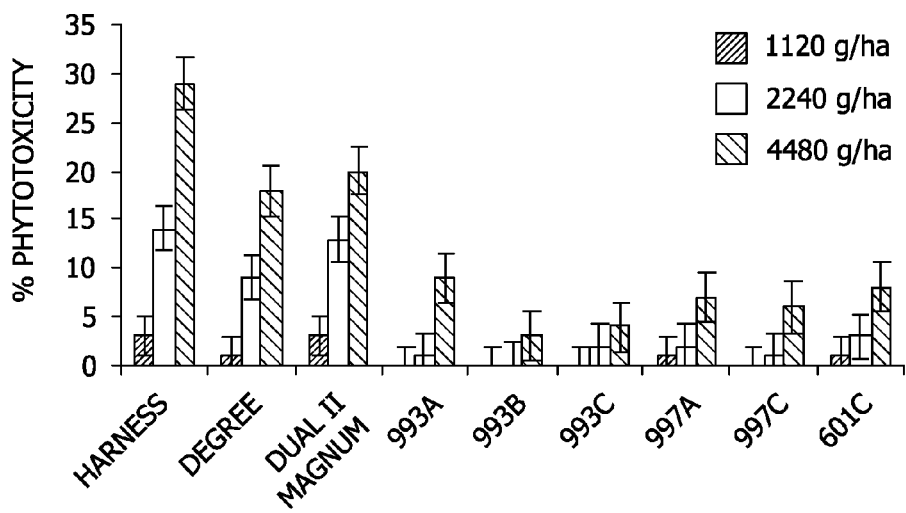
FIG. 63 is a graph depicting soybean injury that occurred with post-emergent applications of various microencapsulated acetochlor formulations as described in Example 37.

Study of Soybean and Cotton Crop Safety and Post-emergence Weed Control Efficacy Using Microencapsulated Acetochlor Formulations of the Invention Formulations 993A, 993B, 993C, 997A, 997C, and 601C (prepared according to the methods described in Examples 34 through 36) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, and DUAL II MAGNUM. The formulations were applied to post-emergent soybean and cotton plants and measured for phytotoxicity 14 DAT. The results are shown in FIG. 62 (cotton injury) and FIG. 63 (soybean injury).

All experimental formulations demonstrated significantly less soybean injury than DEGREE at the two higher application rates. Cotton injury showed three formulations, 993A, 993C, and 997A to be as injurious as DEGREE at the highest application rate. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 993A | 81 | 108 |
| 993B | 64 | 86 |
| 993C | 50 | 69 |
| 997A | 79 | 106 |
| 997C | 53 | 73 |
| 601C | 74 | 94 |
| DEGREE | 134 | 217 |

Figure 64:
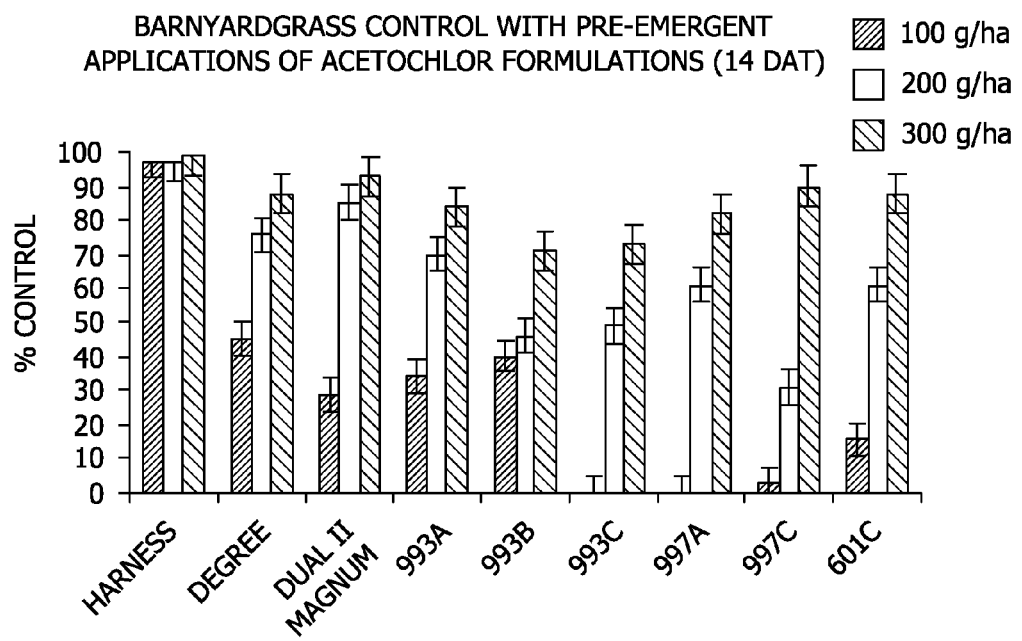
FIG. 64 is a graph depicting control of barnyard grass achieved with pre-emergent applications of various microencapsulated acetochlor formulations as described in Example 37.
Figure 65:
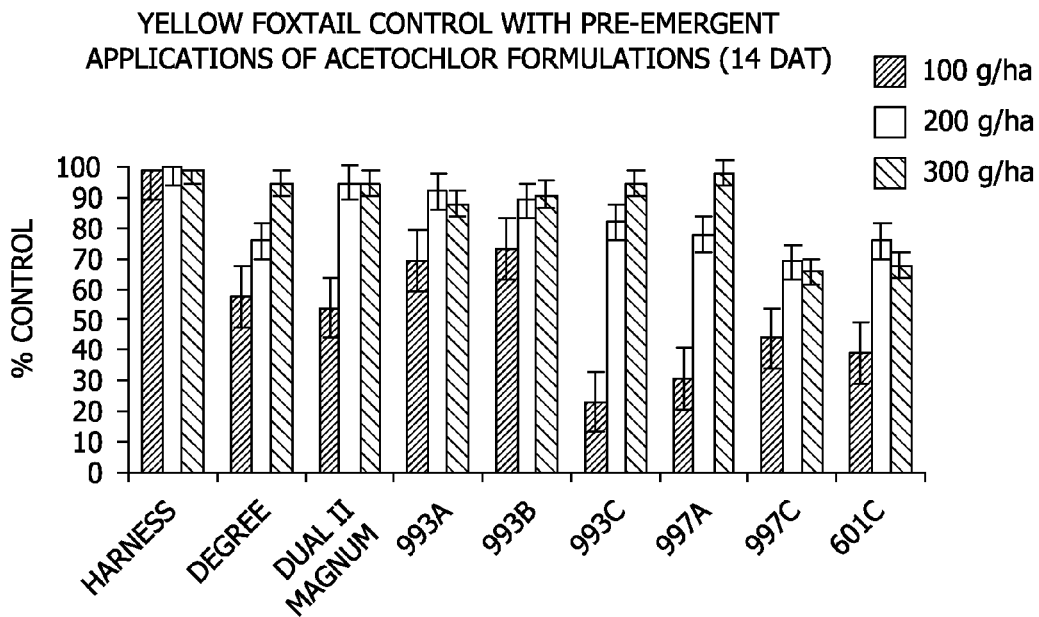
FIG. 65 is a graph depicting control of yellow foxtail achieved with pre-emergent applications of various microencapsulated acetochlor formulations as described in Example 37.

Formulations 993A, 993B, 993C, 997A, 997C, and 601C were also tested for weed control efficacy and compared to the weed control efficacy of DEGREE, HARNESS, and DUAL II MAGNUM. The weed species tested were Barnyardgrass (*Echinochloa crus-galli*) and Yellow foxtail (*Setaria lutescens*). The weed control efficacy data are presented in FIGS. 64 and 65.

Formulation 993A was the only formulation to provide barnyardgrass control that was equivalent to DEGREE at all application rates. See FIG. 64. Yellow foxtail control showed Formulations 993A and 993B to be equal to or better than DEGREE. See FIG. 65. Weakest activity across these two species was seen with Formulations 997C and 601C. There was a clear trend toward lower efficacy as capsule size increased.

Example 38

Preparation of Aqueous Dispersions of Microencapsulated Acetochlor

Three aqueous dispersions of microencapsulated acetochlor (designated formulation 609A, 609B, and 609C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. In these formulations, the acetochlor loading approximately 33% by weight, which is relatively lower than the acetochlor loading in DEGREE.

To prepare the formulation, large batches of each of the internal phase, the external phase, the amine solution, and the stabilizer solution were prepared containing the components and amounts shown in the following table:

| Component | Form. 609A | Form. 609B | Form. 609C |
|---|---|---|---|
| | Weight of Component (g) | | |
| Internal Phase | | | |
| Acetochlor | | 418.10 | |
| NORPAR 15 | | 21.70 | |
| MISTAFLEX H9915 | | 30.56 | |
| External Phase | | | |
| Glycerin | | 123.10 | |
| SOKALAN CP9 | | 36.32 | |
| Ammonium Caseinate | | 0.74 | |
| Acid | | 2.84 | |
| Water | | 443.6 | |
| TETA, 50% solution | 5.12 | 5.11 | 5.13 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

Particle Size Parameters

| Formulations | Mean Particle size (μm) | Standard Deviation (μm) |
|---|---|---|
| 609A | 3.28 | 2.63 |
| 609B | 11.61 | 7.22 |
| 609C | 12.65 | 7.66 |

Example 39

Figure 66:
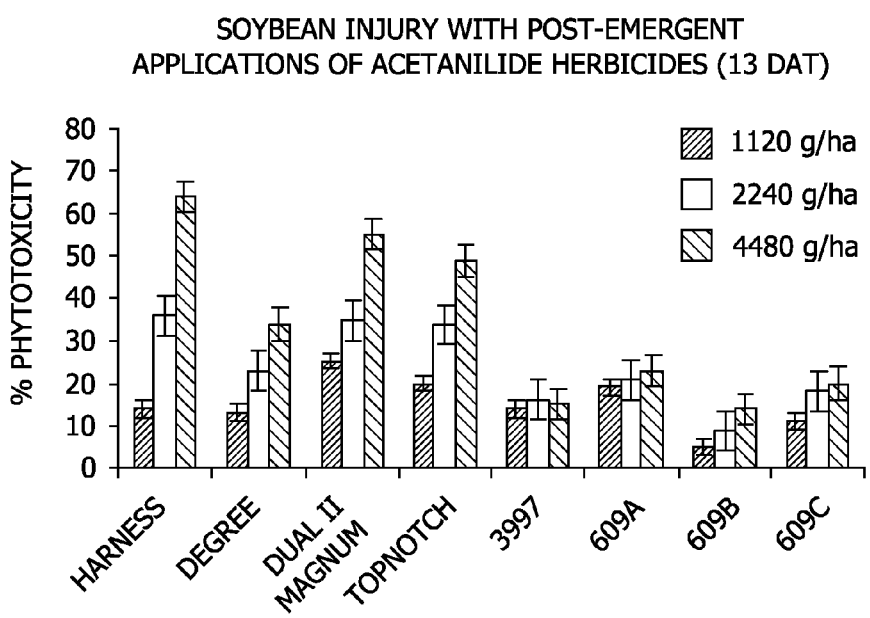
FIG. 66 is a graph depicting soybean injury that occurred with post-emergent applications of various microencapsulated acetochlor formulations as described in Example 39.
Figure 67:
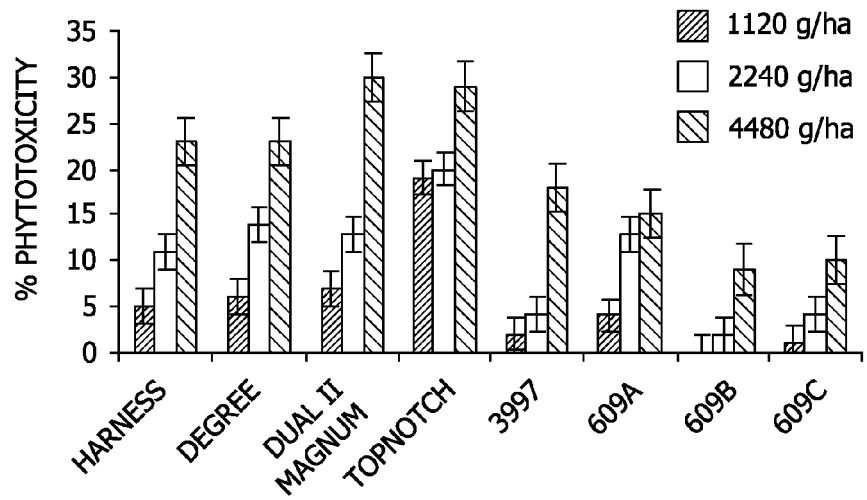
FIG. 67 is a graph depicting cotton injury that occurred with post-emergent applications of various microencapsulated acetochlor formulations as described in Example 39.

Study of Soybean and Cotton Crop Safety and Post-emergence Weed Control Efficacy Using Microencapsulated Acetochlor Formulations of the Invention Formulations 609A, 609B and 609C (prepared according to the methods described in Example 38) were applied to glyphosate-tolerant (ROUNDUP READY) soybean (AG 4403) and glyphosate-tolerant (ROUNDUP READY) cotton (RR Flex—short to mid-season variety) crops under greenhouse conditions. These formulations were tested against commercial formulations HARNESS, DEGREE, DUAL II MAGNUM, and TOPNOTCH. The formulations were applied to post-emergent soybean and cotton plants and measured for phytotoxicity 13 DAT. The results are shown in FIG. 66 (soybean injury) and FIG. 67 (cotton injury). Formulations 609B and 609C provided the best crop safety among experimental formulations.

Figure 68:
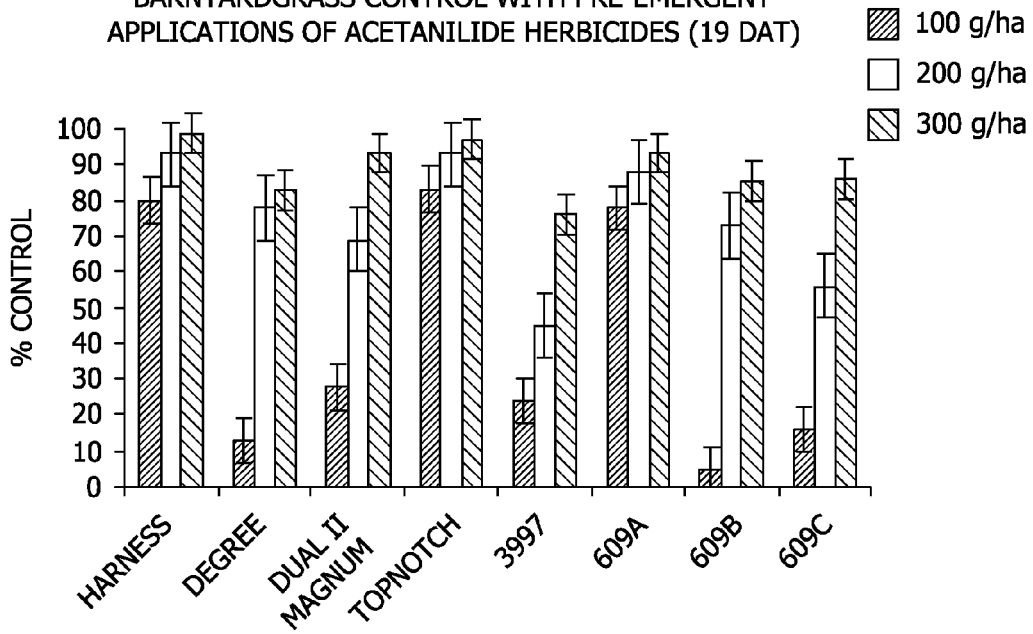
FIG. 68 is a graph depicting control of barnyard grass achieved with pre-emergent applications of various microencapsulated acetochlor formulations as described in Example 39.
Figure 69:
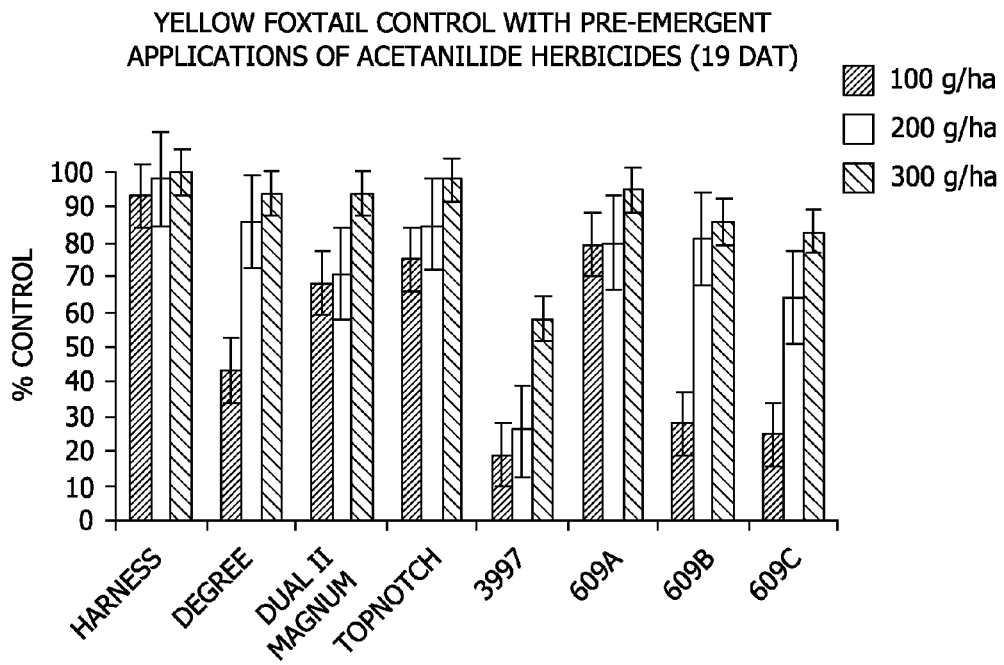
FIG. 69 is a graph depicting control of yellow foxtail achieved with pre-emergent applications of various microencapsulated acetochlor formulations as described in Example 39.

Formulations 609A, 609B and 609C were also tested for weed control efficacy and compared to the weed control efficacy of DEGREE, HARNESS, DUAL II MAGNUM, and TOPNOTCH. The weed species tested were Barnyardgrass (*Echinochloa crus-galli*) and Yellow foxtail (*Setaria lutescens*). The weed control efficacy data are presented in FIGS. 68 and 69.

Formulation 609A provided the highest levels of weed control among the experimental formulations. See FIGS. 68 and 69. Since this formulation had the smallest capsule size this result is not surprising. While the other two formulations were less efficacious, they still provided weed control that was comparable to DEGREE.

Example 40

Preparation of Aqueous Dispersions of Microencapsulated Acetochlor

Three aqueous dispersions of microencapsulated acetochlor (designated formulation 613A, 613B, and 613C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 613A, 613B, and 613C were prepared using a higher proportion of shell wall components compared to commercially available DEGREE. The formulation for DEGREE employs about 8% by weight shell wall components compared to the acetochlor loading. By comparison, formulations 613A, 613B, and 613C were prepared with 16% by weight shell wall components compared to the acetochlor loading.

To prepare the formulation, large batches of each of the internal phase, the external phase, the amine solution, and the stabilizer solution were prepared containing the components and amounts shown in the following table:

| Component | Form. 613A | Form. 613B | Form. 613C |
|---|---|---|---|
| | Weight of Component (g) | | |
| Internal Phase | | | |
| Acetochlor | | 507.0 | |
| NORPAR 15 | | 26.30 | |
| MISTAFLEX H9915 | | 81.01 | |
| External Phase | | | |
| Glycerin | | 88.81 | |
| SOKALAN CP9 | | 26.2 | |
| Ammonium Caseinate | | 0.52 | |
| Acid | | 1.96 | |
| Water | | 320.0 | |
| TETA, 50% solution | 13.56 | 13.56 | 13.57 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 613A | 3.24 | 3.37 |
| 613B | 7.73 | 5.18 |
| 613C | 10.90 | 7.88 |

Example 41

Preparation of Aqueous Dispersions of Microencapsulated Acetochlor

Three aqueous dispersions of microencapsulated acetochlor (designated formulation 617A, 617B, and 617C) were prepared. These formulations were prepared using the MISTAFLEX blend comprising DES N3200 and DES W and a single amine, TETA. The molar equivalents ratio of amine molar equivalents to isocyanate molar equivalents was approximately 1.25:1. Formulations 617A, 617B, and 617C were prepared using a similar relative proportion of shell wall components compared to DEGREE.

To prepare the formulation, large batches of each of the internal phase, the external phase, the amine solution, and the stabilizer solution were prepared containing the components and amounts shown in the following table:

| Component | Form. 617A | Form. 617B | Form. 617C |
|---|---|---|---|
| | Weight of Component (g) | | |
| Internal Phase | | | |
| Acetochlor | | 506.78 | |
| NORPAR 15 | | 26.33 | |
| MISTAFLEX H9915 | | 35.48 | |

-continued

| Component | Form. 617A | Form. 617B | Form. 617C |
|---|---|---|---|
| | Weight of Component (g) | | |
| External Phase | | | |
| Glycerin | | 102.2 | |
| SOKALAN CP9 | | 31.1 | |
| Ammonium Caseinate | | 0.62 | |
| Acid | | 2.85 | |
| Water | | 368.3 | |
| TETA, 50% solution | 6.20 | 6.20 | 6.21 |
| Stabilizer | | | |
| Invalon | | 71.83 | |
| Kelzan CC | | 0.64 | |
| Antifoam | | 0.01 | |
| Glycerin | | 48.15 | |
| Proxel GXL | | 0.64 | |
| Caustic | | 0.22 | |
| Buffer | | 1.43 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 617A | 7.10 | 4.67 |
| 617B | 8.93 | 5.75 |
| 617C | 11.23 | 6.86 |

Example 42

Preparation of Aqueous Dispersions of Microencapsulated Acetochlor

Four aqueous dispersions of microencapsulated acetochlor (designated formulation 621A, 621B, 621C, and 621D) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 621A, 621B, 621C, and 621D were prepared using a higher proportion of shell wall components compared to DEGREE but a lower proportion compared to the formulations described above in Example 40. Formulations 621A, 621B, 621C, and 621D were prepared with 12% by weight shell wall components compared to the acetochlor loading.

To prepare the formulation, large batches of each of the internal phase, the external phase, the amine solution, and the stabilizer solution were prepared containing the components and amounts shown in the following table:

| Component | Form. 621A | Form. 621B | Form. 621C | Form. 621D |
|---|---|---|---|---|
| | Weight of Component (g) | | | |
| Internal Phase | | | | |
| Acetochlor | | 675.72 | | |
| NORPAR 15 | | 35.10 | | |
| MISTAFLEX H9915 | | 77.3 | | |
| External Phase | | | | |
| Glycerin | | 127.6 | | |
| SOKALAN CP9 | | 37.90 | | |
| Ammonium Caseinate | | 0.25 | | |
| Acid | | 3.0 | | |
| Water | | 461.0 | | |
| TETA, 50% solution | 9.72 | 9.72 | 9.72 | 9.73 |
| Stabilizer | | | | |
| Invalon | | 95.77 | | |
| Kelzan CC | | 0.86 | | |
| Antifoam | | 0.02 | | |
| Glycerin | | 64.20 | | |
| Proxel GXL | | 0.86 | | |
| Caustic | | 0.29 | | |
| Buffer | | 1.91 | | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Four separate amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 621A | 6.70 | 4.42 |
| 621B | 8.88 | 5.89 |
| 621C | 2.48 | 2.43 |
| 621D | 11.53 | 7.02 |

Example 43

Figure 70:
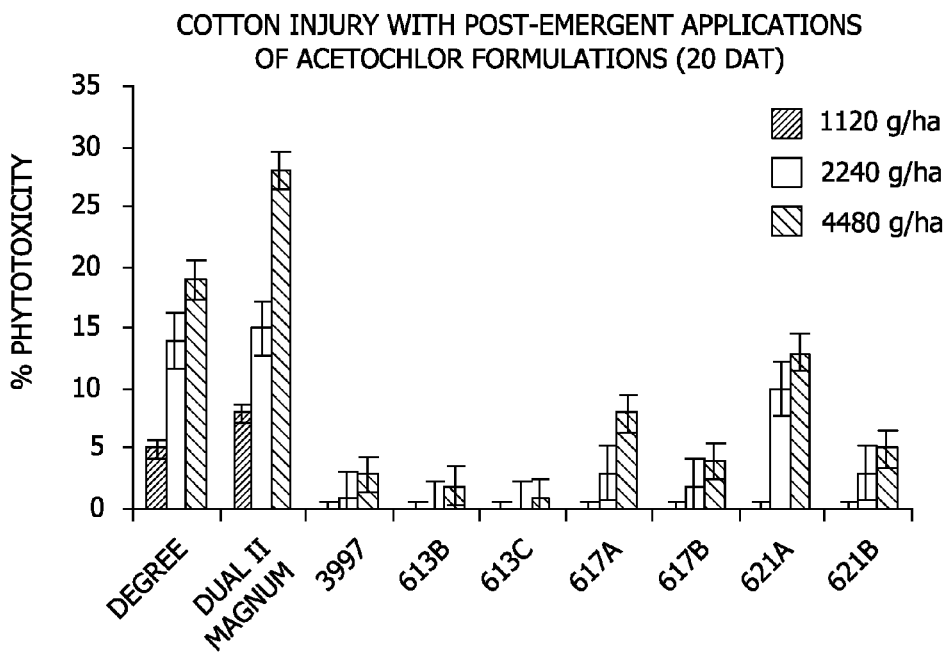
FIG. 70 is a graph depicting cotton injury that occurred with post-emergent applications of various microencapsulated acetochlor formulations as described in Example 43.

St.udy of Soybean and Cotton Crop Safety and Post-emergence Weed Control Efficacy Using Microencapsulated Acetochlor Formulations of the Invention Formulations 613B, 613C, 617A, 617B, 621A, and 621B (prepared according to the methods described in Examples 40 through 42) were applied to and cotton (RR Flex—short to mid-season variety) crops under greenhouse conditions. These formulations were tested against commercial formulations DEGREE and DUAL II MAGNUM and against formulation 3997. The formulations were applied to post-emergent cotton plants and measured for phytotoxicity 20 DAT. The results are shown in FIG. 70.

Formulations 617B, 621B, 613B, and 613C provided post emergent ("POE") cotton safety that was equivalent to formulation 3997. See FIG. 70. The least injury among the experimental formulations was shown by formulations 613B and 613C, both of which had the highest percentage of shell wall component. Formulations 617A and 621A showed significantly greater injury than formulation 3997, but less than that seen with DEGREE and DUAL II MAGNUM. Both formulations have smaller capsule size, thus demonstrating once again the importance of capsule size to crop safety. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 613B | 52 | 65 |
| 613C | 45 | 55 |
| 617A | 77 | 97 |
| 617B | 79 | 95 |
| 621A | 100 | 123 |
| 621B | 65 | 82 |
| DEGREE | 127 | 182 |
| DEGREE | 118 | 174 |

Figure 71:
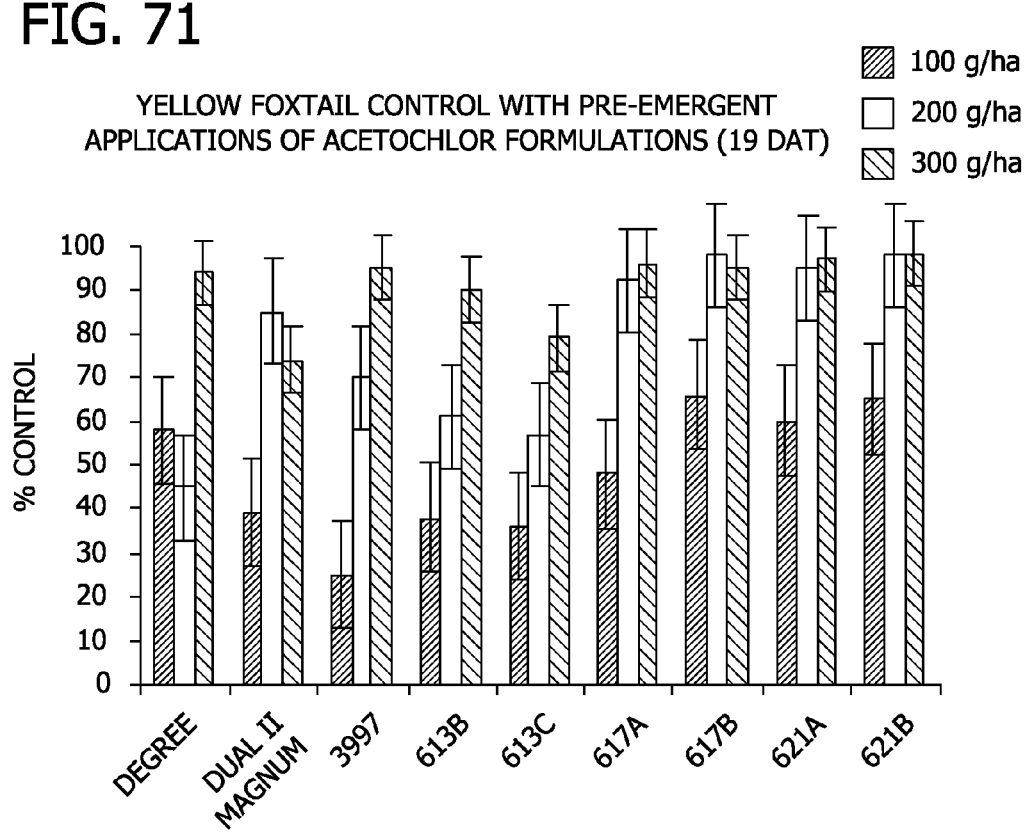
FIG. 71 is a graph depicting control of yellow foxtail achieved with pre-emergent applications of various microencapsulated acetochlor formulations as described in Example 43.
Figure 72:
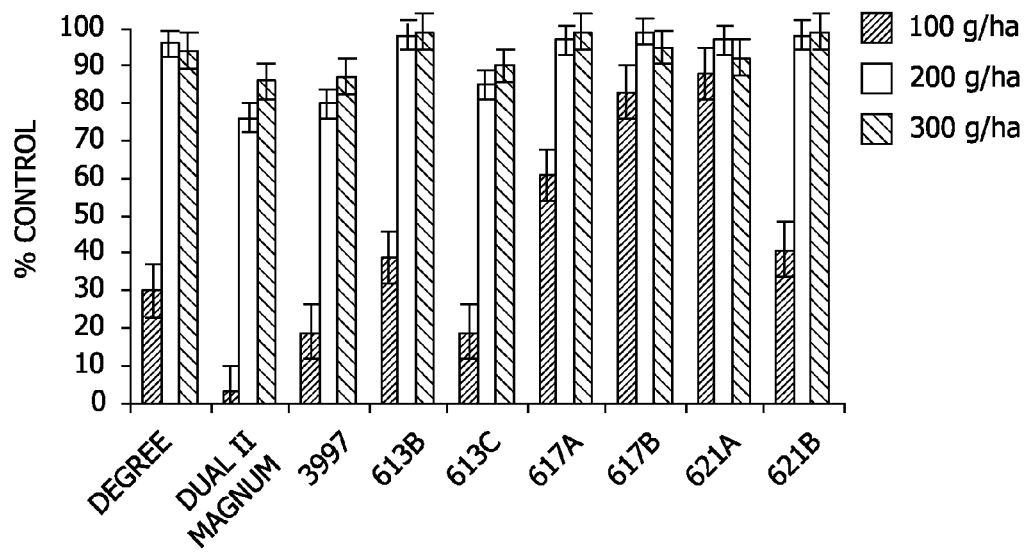
FIG. 72 is a graph depicting control of barnyard grass achieved with pre-emergent applications of various microencapsulated acetochlor formulations as described in Example 43.

Formulations 613B, 613C, 617A, 617B, 621A, and 621B were also tested for weed control efficacy and compared to the weed control efficacy of DEGREE and DUAL II MAGNUM. The weed species tested were Barnyardgrass (*Echinochloa crus-galli*) and Yellow foxtail (*Setaria lutescens*). The weed control efficacy data are presented in FIGS. 71 and 72.

Weed control data showed Formulations 613B and 613C to be least effective among the experimental formulations in the control of yellow foxtail, although control was similar to the standards. See FIG. 71. This would suggest that the thickest shell wall with these two formulations is slowing the release of acetochlor. This was evident to a lesser degree in the control of barnyardgrass. See FIG. 72.

Example 44

Preparation of Aqueous Dispersions of Microencapsulated Acetochlor

Three aqueous dispersions of microencapsulated acetochlor (designated formulations 660A, 660B, and 660C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 660A, 660B, and 660C were prepared having an acetochlor loading of about 33% by weight, which is a relatively lower proportion of acetochlor compared to DEGREE.

To prepare the formulation, large batches of each of the internal phase, the external phase, the amine solution, and the stabilizer solution were prepared containing the components and amounts shown in the following table:

| Component | Form. 660A | Form. 660B | Form. 660C |
|---|---|---|---|
| | Weight of Component (g) | | |
| Internal Phase | | | |
| Acetochlor | | 524.1 | |
| NORPAR 15 | | 27.0 | |
| MISTAFLEX H9915 | | 38.32 | |

-continued

| Component | Form. 660A | Form. 660B | Form. 660C |
|---|---|---|---|
| | Weight of Component (g) | | |
| External Phase | | | |
| Glycerin | | 146.40 | |
| SOKALAN CP9 | | 43.22 | |
| Ammonium Caseinate | | 0.88 | |
| Acid | | 3.15 | |
| Water | | 527.40 | |
| TETA, 50% solution | 6.43 | 6.42 | 6.45 |
| Stabilizer | | | |
| Invalon | | 108.38 | |
| Kelzan CC | | 0.97 | |
| Antifoam | | 0.02 | |
| Glycerin | | 72.65 | |
| Proxel GXL | | 0.97 | |
| Caustic | | 0.33 | |
| Buffer | | 2.16 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three amine solutions were used to initiate polymerization. During emulsification, the mixer speed was varied by controlling the blender to achieve mean particle sizes as shown in the table:

TABLE

| | Particle Size Parameters | |
|---|---|---|
| Formulations | Mean Particle size (μm) | Standard Deviation (μm) |
| 660A | 12.50 | 8.59 |
| 660B | 10.13 | 7.69 |
| 660C | 6.83 | 4.77 |

Example 45

Preparation of Aqueous Dispersions of Microencapsulated Acetochlor

Three aqueous dispersions of microencapsulated acetochlor (designated formulations 664A, 664B, and 664C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 664A, 664B, and 664C were prepared to have an acetochlor loading of about 33% by weight, which is a relatively lower proportion of acetochlor compared to DEGREE. Additionally, formulations 664A, 664B, and 664C were prepared using a different internal phase solvent, ISOPAR L, compared to NORPAR as used in above Example 44.

To prepare the formulation, large batches of each of the internal phase, the external phase, the amine solution, and the stabilizer solution were prepared containing the components and amounts shown in the following table:

| Component | Form. 664A | Form. 664B | Form. 664C |
|---|---|---|---|
| | Weight of Component (g) | | |
| Internal Phase | | | |
| Acetochlor | | 524.10 | |
| ISOPAR L | | 54.10 | |
| MISTAFLEX H9915 | | 40.15 | |
| External Phase | | | |
| Glycerin | | 140.40 | |
| SOKALAN CP9 | | 41.40 | |
| Ammonium Caseinate | | | |
| Acid | | 3.10 | |
| Water | | 506.0 | |
| TETA, 50% solution | 6.75 | 6.75 | 6.74 |
| Stabilizer | | | |
| Invalon | | 108.38 | |
| Kelzan CC | | 0.97 | |
| Antifoam | | 0.02 | |
| Glycerin | | 72.65 | |
| Proxel GXL | | 0.97 | |
| Caustic | | 0.33 | |
| Buffer | | 2.16 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three amine solutions were used to initiate polymerization. During emulsification, the mixer speed was varied by controlling the blender to achieve mean particle sizes as shown in the table:

TABLE

Particle Size Parameters

| Formulation | Mean Particle size (µm) | Standard Deviation (µm) |
|---|---|---|
| 664A | 6.84 | 5.24 |
| 664B | 8.27 | 5.47 |
| 664C | 9.35 | 5.95 |

Example 46

Preparation of Aqueous Dispersions of Microencapsulated Acetochlor

Three aqueous dispersions of microencapsulated acetochlor (designated formulations 668A, 668B, and 668C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 668A, 668B, and 668C were prepared to have an acetochlor loading of about 33% by weight, which is a relatively lower proportion of acetochlor compared to DEGREE. Additionally, formulations 668A, 668B, and 668C were prepared using a different internal phase solvent, Exxsol D-110, compared to NOR-PAR as used in above Example 44.

To prepare the formulation, large batches of each of the internal phase, the external phase, the amine solution, and the stabilizer solution were prepared containing the components and amounts shown in the following table:

| Component | Forms. 668A, 668B, 668C |
|---|---|
| | Weight of Component (g) |
| Internal Phase | |
| Acetochlor | 524.10 |
| Exxsol D-110 | 54.10 |
| MISTAFLEX H9915 | 40.15 |
| External Phase | |
| Glycerin | 140.30 |
| SOKALAN CP9 | 41.40 |
| Ammonium Caseinate | 0.85 |
| Acid | 3.05 |
| Water | 506.0 |
| TETA, 50% solution | 20.36 |
| Stabilizer | |
| Invalon | 108.38 |
| Kelzan CC | 0.97 |
| Antifoam | 0.02 |
| Glycerin | 72.65 |
| Proxel GXL | 0.97 |
| Caustic | 0.33 |
| Buffer | 2.16 |

The aqueous dispersions of microcapsules were prepared substantially as described above in Example 1. To prepare each formulation, the large internal phase, external phase, amine, and stabilizer batches were divided into smaller approximately equal weight batches and combined as described in Example 1. During emulsification, the mixer speed was varied by controlling the blender to achieve mean particle sizes as shown in the table:

TABLE

Particle Size Parameters

| Formulation | Mean Particle size (µm) | Standard Deviation (µm) |
|---|---|---|
| 668A | 6.75 | 4.55 |
| 668B | 7.02 | 4.75 |
| 668C | 9.75 | 6.16 |

Example 47

Preparation of Aqueous Dispersions of Microencapsulated Acetochlor

Three aqueous dispersions of microencapsulated acetochlor (designated formulations 672A, 672B, and 672C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 672A, 672B, and 672C were prepared having an acetochlor loading of about 33% by weight, which is a relatively lower proportion of acetochlor compared to DEGREE. Additionally, formulations 672A, 672B, and 672C were prepared using a different internal phase solvent, ISOPAR V, compared to NORPAR as used in above Example 44.

To prepare the formulation, large batches of each of the internal phase, the external phase, the amine solution, and the stabilizer solution were prepared containing the components and amounts shown in the following table:

| Component | Form. 672A | Form. 672B | Form. 672C |
|---|---|---|---|
| | Weight of Component (g) | | |
| Internal Phase | | | |
| Acetochlor | | 524.1 | |
| ISOPAR V | | 27.1 | |
| MISTAFLEX H9915 | | 38.3 | |
| External Phase | | | |
| Glycerin | | 146.4 | |
| SOKALAN CP9 | | 43.2 | |
| Ammonium Caseinate | | 0.88 | |
| Acid | | 3.25 | |
| Water | | 521.4 | |
| TETA, 50% solution | 6.40 | 6.42 | 6.43 |
| Stabilizer | | | |
| Invalon | | 108.38 | |
| Kelzan CC | | 0.97 | |
| Antifoam | | 0.02 | |
| Glycerin | | 72.65 | |
| Proxel GXL | | 0.97 | |
| Caustic | | 0.33 | |
| Buffer | | 2.16 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

| Particle Size Parameters | | |
|---|---|---|
| Formulation | Mean Particle size (μm) | Standard Deviation (μm) |
| 672A | 8.13 | 5.35 |
| 672B | 8.82 | 5.71 |
| 672C | 10.82 | 7.59 |

Example 48

Figure 73:
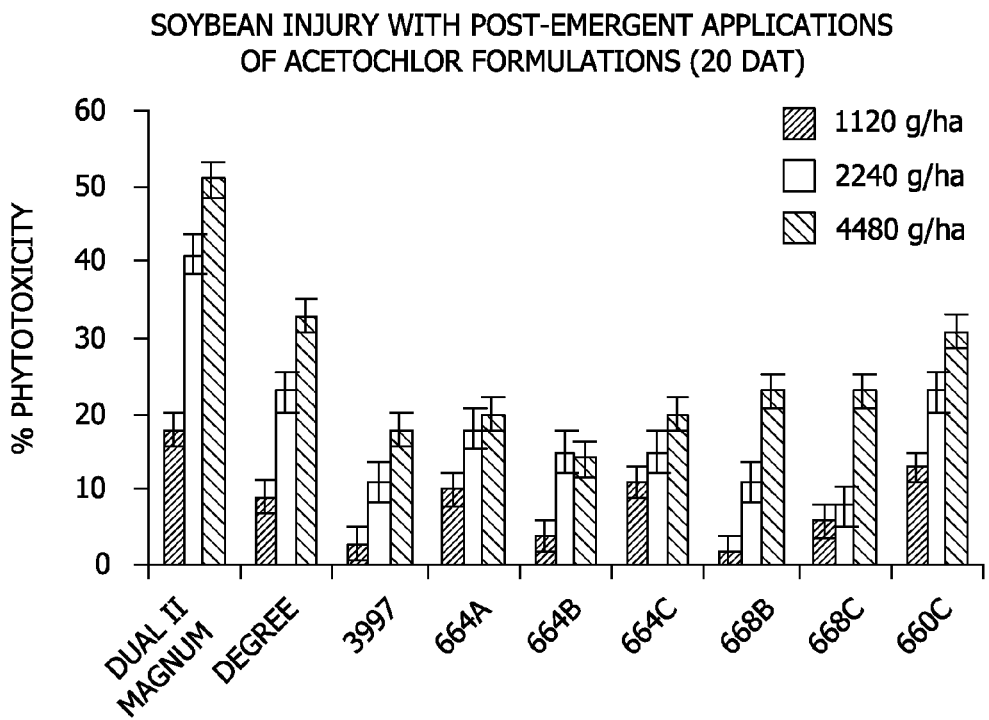
FIG. 73 is a graph depicting soybean injury that occurred with post-emergent applications of various microencapsulated acetochlor formulations as described in Example 48.
Figure 74:
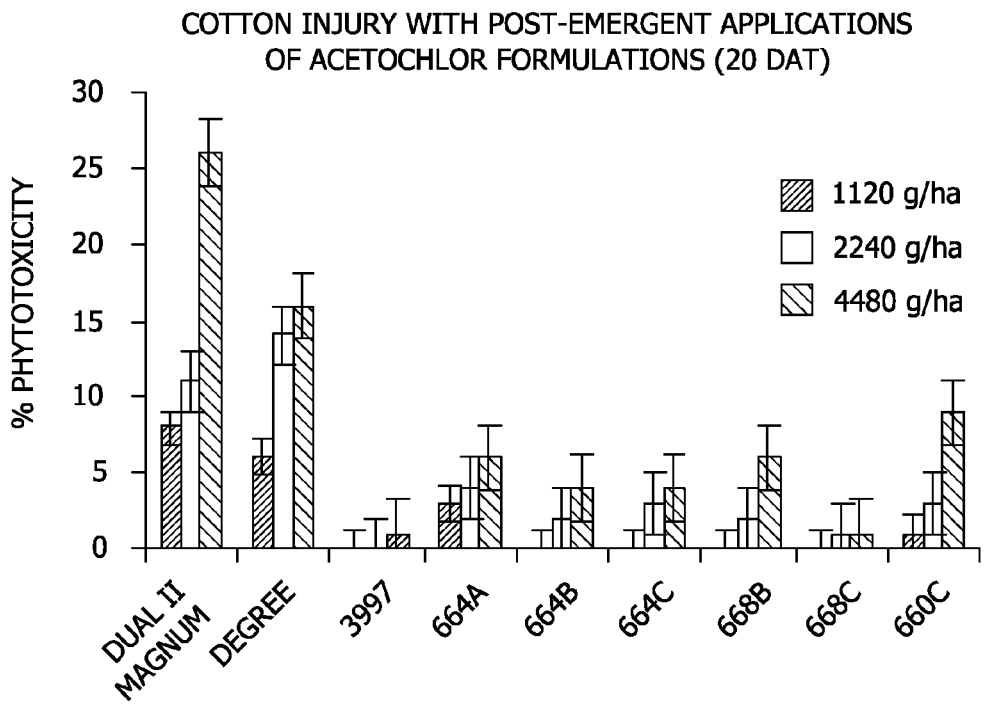
FIG. 74 is a graph depicting cotton injury that occurred with post-emergent applications of various microencapsulated acetochlor formulations as described in Example 48.

Study of Soybean and Cotton Crop Safety and Post-emergence Weed Control Efficacy Using Microencapsulated Acetochlor Formulations of the Invention Formulations 664A, 664B, 664C, 668B, 668C, and 660C (prepared according to the methods described in Examples 44 through 47) were applied to glyphosate-tolerant (ROUNDUP READY) soybeans and glyphosate-tolerant (ROUNDUP READY) cotton (RR Flex—short to mid-season variety) crops under greenhouse conditions. These formulations were tested against commercial formulations DEGREE and DUAL II MAGNUM and against formulation 3997. The formulations were applied to post-emergent cotton plants and measured for phytotoxicity 20 DAT. The results are shown in FIG. 73 (soybean injury) and FIG. 74 (cotton injury).

Formulation 664B showed the best crop safety in soybeans and along with formulations 668B and 668C showed better crop safety than DEGREE at all application rates. See FIG. 73. Formulation 660C provided soybean safety that was no better than that found with DEGREE. Formulations 664B, 664C, and 668C showed the best crop safety in cotton, although all experimental formulations provided significantly better crop safety than DEGREE. See FIG. 74. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 664A | 98 | 118 |
| 664B | 75 | 89 |
| 664C | 68 | 83 |
| 668B | 81 | 94 |
| 668C | 59 | 69 |
| 660C | 118 | 144 |

Figure 77:
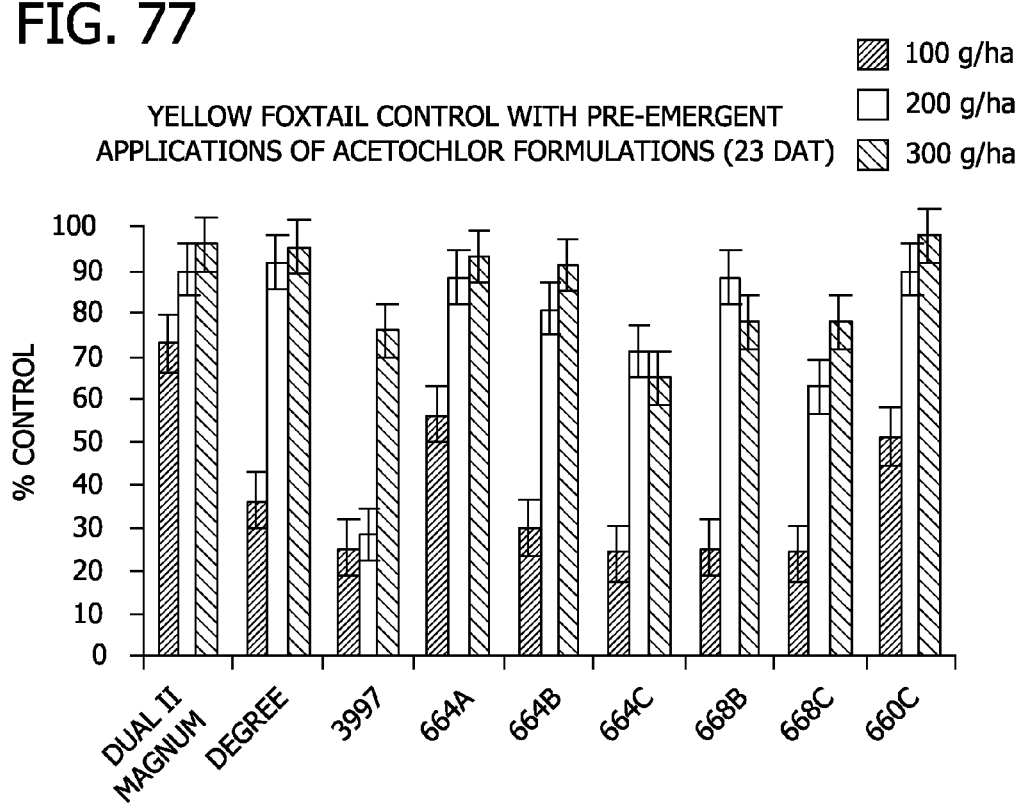
FIG. 77 is a graph depicting control of yellow foxtail achieved with pre-emergent applications of various microencapsulated acetochlor formulations as described in Example 48.

Formulations 664A, 664B, 664C, 668B, 668C, and 660C were also tested for weed control efficacy and compared to the weed control efficacy of DEGREE, DUAL II MAGNUM, and formulation 3997. The weed species tested were Crabgrass (*Digitaria sanguinalis*), Barnyardgrass (*Echinochloa crus-galli*) and Yellow foxtail (*Setaria lutescens*). The weed control efficacy data are presented in FIGS. 75, 76, and 77.

Formulations 664A and 660C consistently provided the best weed control efficacy across species among the experimental formulations. Both formulations were comparable to the standards, DEGREE and DUAL II MAGNUM in the control of crabgrass. See FIG. 75. All other formulations were less effective with Formulation 664C and 668B showing the poorest performance. A similar response was seen in the control of barnyardgrass with formulations 664A and 660C providing control equal to the standards. See FIG. 76. Formulation 664B was slightly less effective and formulation 664C gave the weakest control. Formulations 664A and 660C again showed the best control of yellow foxtail and were closely similar to DUAL1 II MAGNUM. See FIG. 77. Formulation 664B was slightly less effective, but comparable to DEGREE. As seen with crabgrass formulations 664C and 668B gave the weakest control. Based upon crop safety and weed control efficacy the best formulation tested in this group was formulation 664B.

Example 49

Figure 78:
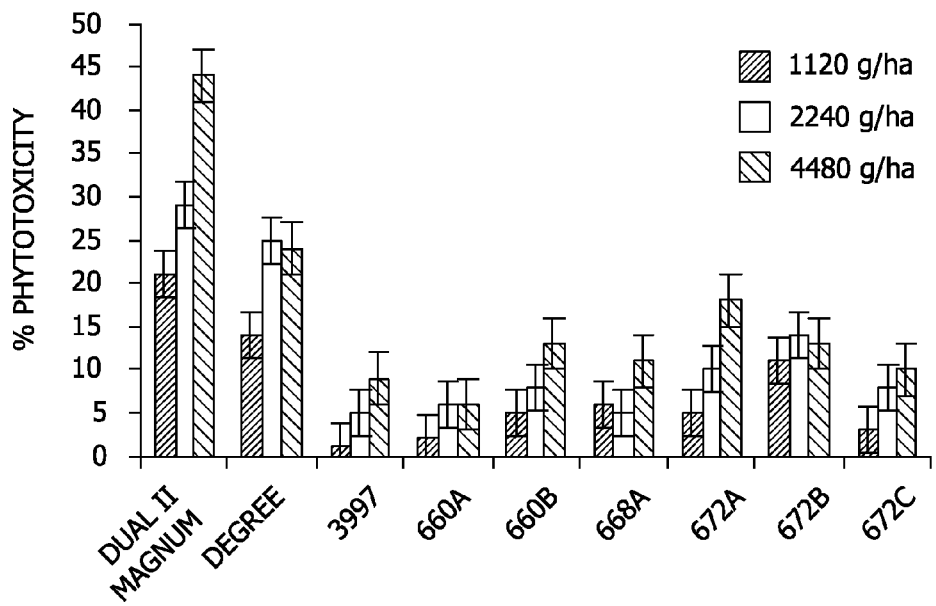
FIG. 78 is a graph depicting soybean injury that occurred with post-emergent applications of various microencapsulated acetochlor formulations as described in Example 49.
Figure 79:
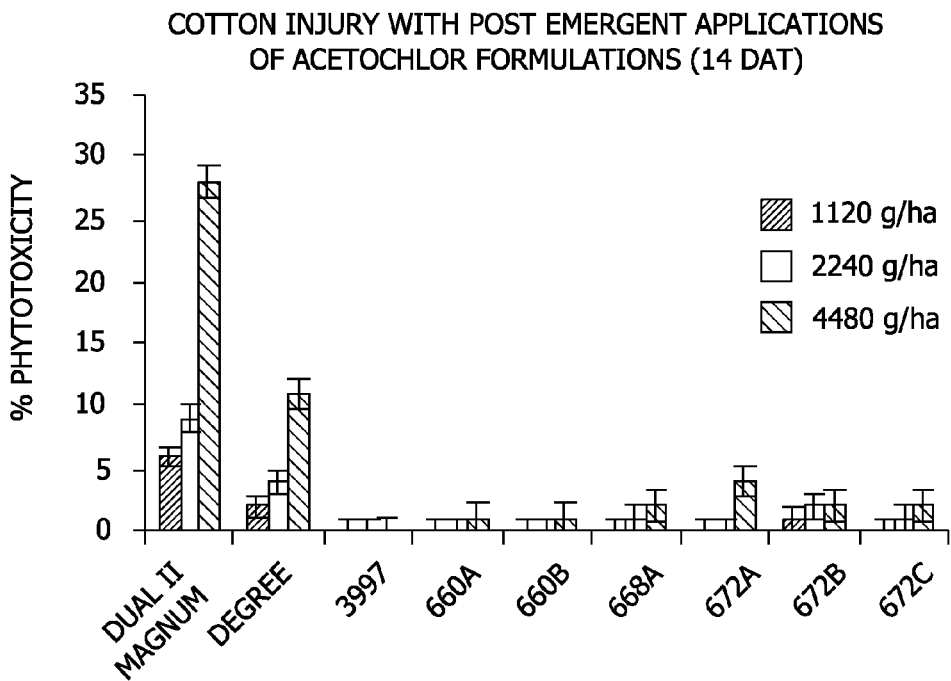
FIG. 79 is a graph depicting cotton injury that occurred with post-emergent applications of various microencapsulated acetochlor formulations as described in Example 49.

Study of Soybean and Cotton Crop Safety and Post-emergence Weed Control Efficacy Using Microencapsulated Acetochlor Formulations of the Invention Formulations 660A, 660B, 668A, 672A, 672B and 672C (prepared according to the methods described in Examples 44 through 47) were applied to glyphosate-tolerant (ROUNDUP READY) soybeans and glyphosate-tolerant (ROUNDUP READY) cotton (RR Flex—short to mid-season variety) crops under greenhouse conditions. These formulations were tested against commercial formulations DEGREE and DUAL II MAGNUM and against formulation 3997. The formulations were applied to post-emergent cotton plants and measured for phytotoxicity 14 DAT. The results are shown in FIG. 78 (soybean injury) and FIG. 79 (cotton injury).

Post-emergence applications to soybeans show all formulations to be safer than DUAL II MAGNUM at all rates and safer than DEGREE at most rates. See FIG. 78. Overall crop injury appeared to be somewhat higher with formulations 972A and 972B. An identical response was seen with post-emergence applications in cotton, although overall crop injury was lower than that seen in soybeans. See FIG. 79.

Figure 80:
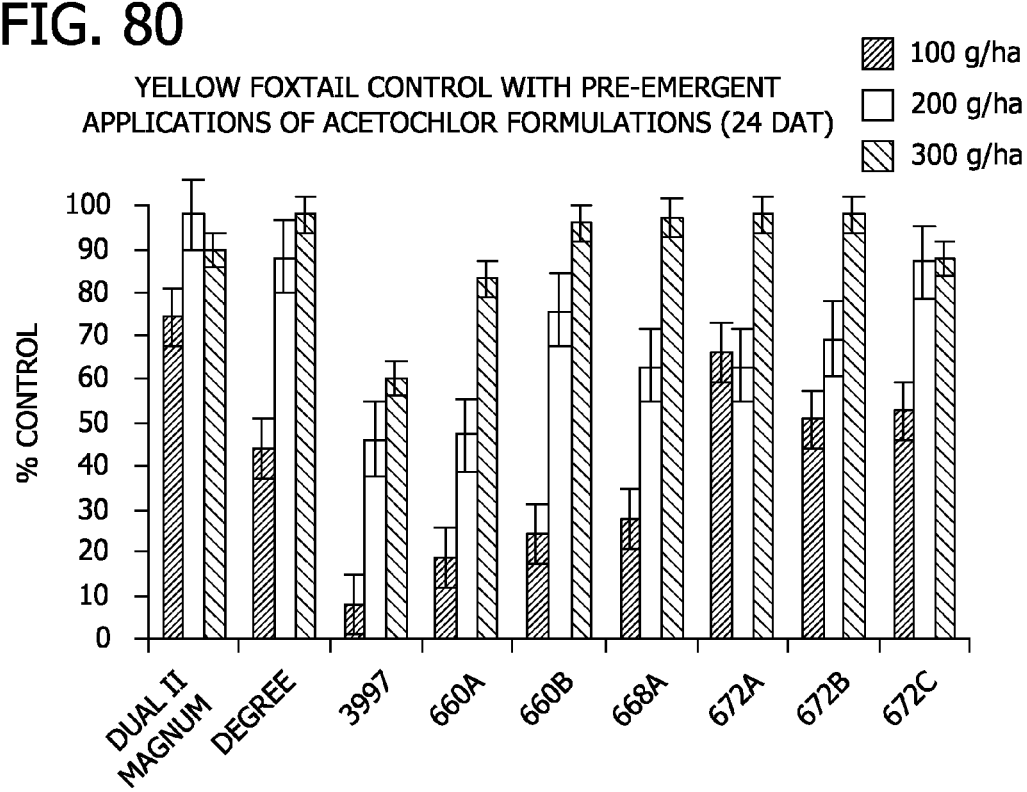
FIG. 80 is a graph depicting control of yellow foxtail achieved with pre-emergent applications of various microencapsulated acetochlor formulations as described in Example 49.
Figure 81:
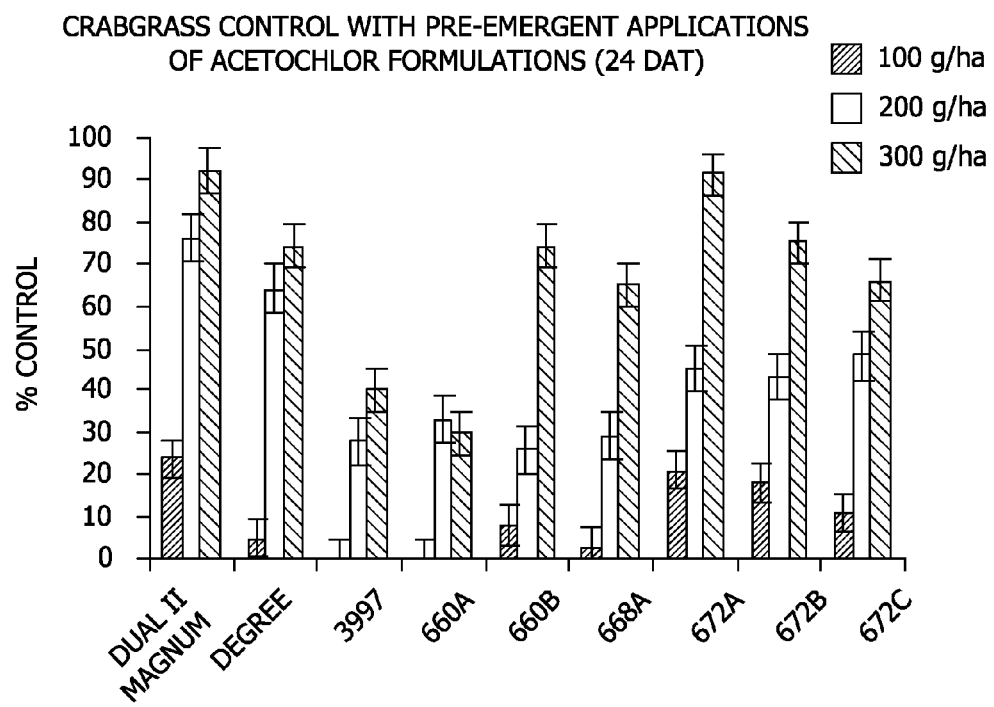
FIG. 81 is a graph depicting control of crabgrass achieved with pre-emergent applications of various microencapsulated acetochlor formulations as described in Example 49.
Figure 82:
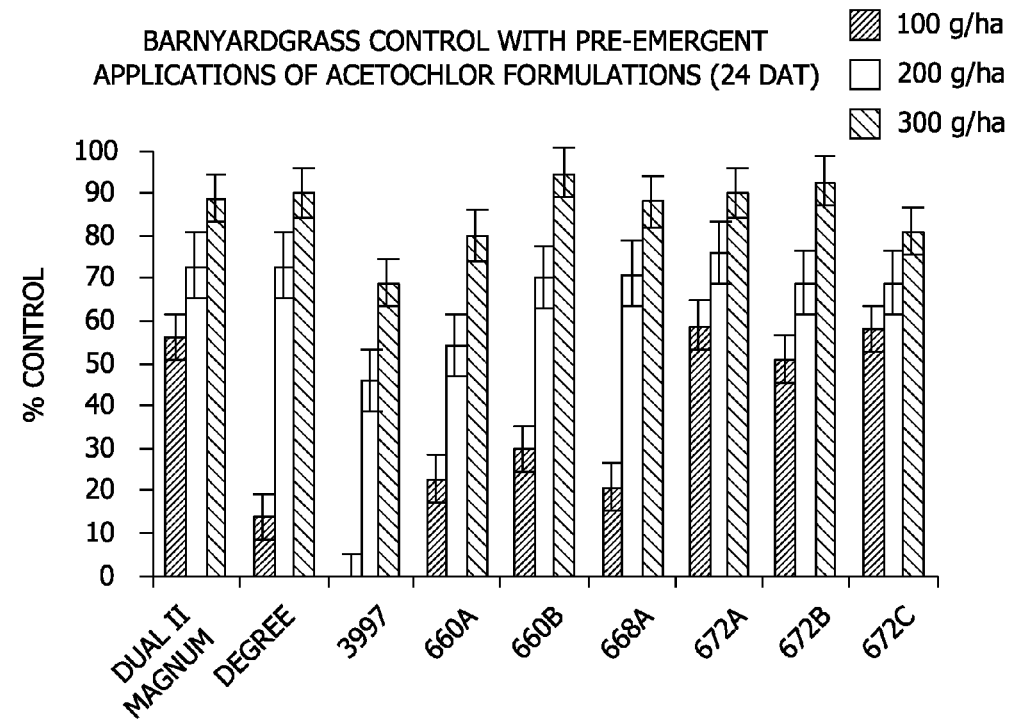
FIG. 82 is a graph depicting control of barnyard grass achieved with pre-emergent applications of various microencapsulated acetochlor formulations as described in Example 49.

Formulations 660A, 660B, 668A, 672A, 672B and 672C were also tested for weed control efficacy and compared to the weed control efficacy of DEGREE, DUAL II MAGNUM, and formulation 3997. The weed species tested were Crabgrass (*Digitaria sanguinalis*), Barnyardgrass (*Echinochloa crus-galli*) and Yellow foxtail (*Setaria lutescens*). The weed control efficacy data are presented in FIGS. 80, 81, and 82.

Formulations 672A, 672B, and 672C consistently provided the best weed control efficacy across species among the experimental formulations. These three formulations along with formulations 660B and 668A were all comparable to DEGREE in terms of yellow foxtail control. See FIG. 80. Formulations 672A, 672B, and 672C were closest to DUAL II MAGNUM across all application rates, while formulations 660B and 668A were weaker at the lowest rate. Formulation 660A provided the poorest yellow foxtail control. Formulations 672A, 672B, and 672C were again closest to the standards for crabgrass control. See FIG. 81. Formulation 660B and 668A were less effective, with formulation 660A again showing the poorest control. Barnyardgrass control showed formulations 672A, 672B, and 672C to be comparable to DUAL II MAGNUM across application rates and better than Degree at the lowest rate. See FIG. 82. Formulations 660B and 668A were similar to DEGREE and formulation 660A was again the weakest performer.

Example 50

Preparation of Aqueous Dispersions of Microencapsulated Acetochlor

Three aqueous dispersions of microencapsulated acetochlor (designated formulations 680A, 680B, and 680C) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 680A, 680B, and 680C were prepared having an acetochlor loading of about 33% by weight, which is a relatively lower proportion of acetochlor compared to DEGREE.

To prepare the formulation, large batches of each of the internal phase, the external phase, the amine solution, and the stabilizer solution were prepared containing the components and amounts shown in the following table:

| Component | Form. 680A | Form. 680B | Form. 680C |
|---|---|---|---|
| | Weight of Component (g) | | |
| Internal Phase | | | |
| Acetochlor | | 524.10 | |
| NORPAR 15 | | 27.10 | |
| MISTAFLEX H9915 | | 38.3 | |
| External Phase | | | |
| Glycerin | | 146.4 | |
| SOKALAN CP9 | | 43.20 | |
| Ammonium Caseinate | | 0.88 | |
| Acid | | 3.50 | |
| Water | | 527.40 | |
| TETA, 50% solution | 6.42 | 6.43 | 6.42 |
| Stabilizer | | | |
| Invalon | | 108.38 | |
| Kelzan CC | | 0.97 | |
| Antifoam | | 0.02 | |
| Glycerin | | 72.65 | |
| Proxel GXL | | 0.97 | |
| Caustic | | 0.33 | |
| Buffer | | 2.16 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

Particle Size Parameters

| Formulation | Mean Particle size (μm) | Standard Deviation (μm) |
|---|---|---|
| 680A | 9.29 | 6.08 |
| 680B | 7.60 | 5.04 |
| 680C | 6.70 | 4.51 |

Example 51

Preparation of Aqueous Dispersions of Microencapsulated Acetochlor

Four aqueous dispersions of microencapsulated acetochlor (designated formulations 684A, 684B, 684C, and 684D) were prepared. These formulations were prepared using the MISTAFLEX blend comprising DES N3200 and DES W and a single amine, TETA. The molar equivalents ratio of amine molar equivalents to isocyanate molar equivalents was approximately 1.2:1. Formulations 684A, 684B, 684C, and 684D were prepared having an acetochlor loading of about 33% by weight, which is a relatively lower proportion of acetochlor compared to DEGREE. Additionally, formulations 684A, 684B, and 684C were prepared using a higher relative concentration of NORPAR solvent as compared to the formulations described in above Example 49. The proportion of NORPAR solvent in formulations 684A, 684B, 684C, and 684D was about 2.14% by weight, compared to 1.8% by weight in the formulations prepared in Example 50. Accordingly, the ratio of weight of acetochlor to weight of NORPAR 15 diluent was approximately 16:1, compared to about 19:1 in the formulations 680A, 680B, and 680C of Example 50.

To prepare the formulation, large batches of each of the internal phase, the external phase, the amine solution, and the stabilizer solution were prepared containing the components and amounts shown in the following table:

| Component | Form. 684A | Form. 684B | Form. 684C |
|---|---|---|---|
| | Weight of Component (g) | | |
| Internal Phase | | | |
| Acetochlor | | 524.10 | |
| NORPAR 15 | | 32.50 | |
| MISTAFLEX H9915 | | 38.60 | |
| External Phase | | | |
| Glycerin | | 145.2 | |
| SOKALAN CP9 | | 42.90 | |
| Ammonium Caseinate | | 0.88 | |
| Acid | | 3.30 | |
| Water | | 523 | |
| TETA, 50% solution | 6.49 | 6.48 | 6.49 |
| Stabilizer | | | |
| Invalon | | 108.38 | |
| Kelzan CC | | 0.97 | |
| Antifoam | | 0.02 | |
| Glycerin | | 72.65 | |
| Proxel GXL | | 0.97 | |
| Caustic | | 0.33 | |
| Buffer | | 2.16 | |

The aqueous dispersions of microcapsules were prepared substantially as described above in Example 1. To prepare each formulation, the large internal phase, external phase, and stabilizer batches were divided into smaller approximately equal weight batches and combined as described in Example 1. Three separate amine solutions were used to initiate polymerization. During emulsification, the mixer speed was varied by controlling the blender to achieve mean particle sizes as shown in the table:

TABLE

Particle Size Parameters

| Formulation | Mean Particle size (μm) | Standard Deviation (μm) |
|---|---|---|
| 684A | 8.36 | 5.59 |
| 684B | 7.04 | 4.78 |
| 684C | 6.33 | 4.35 |
| 684D | 10.3 | — |

Example 52

Figure 83:
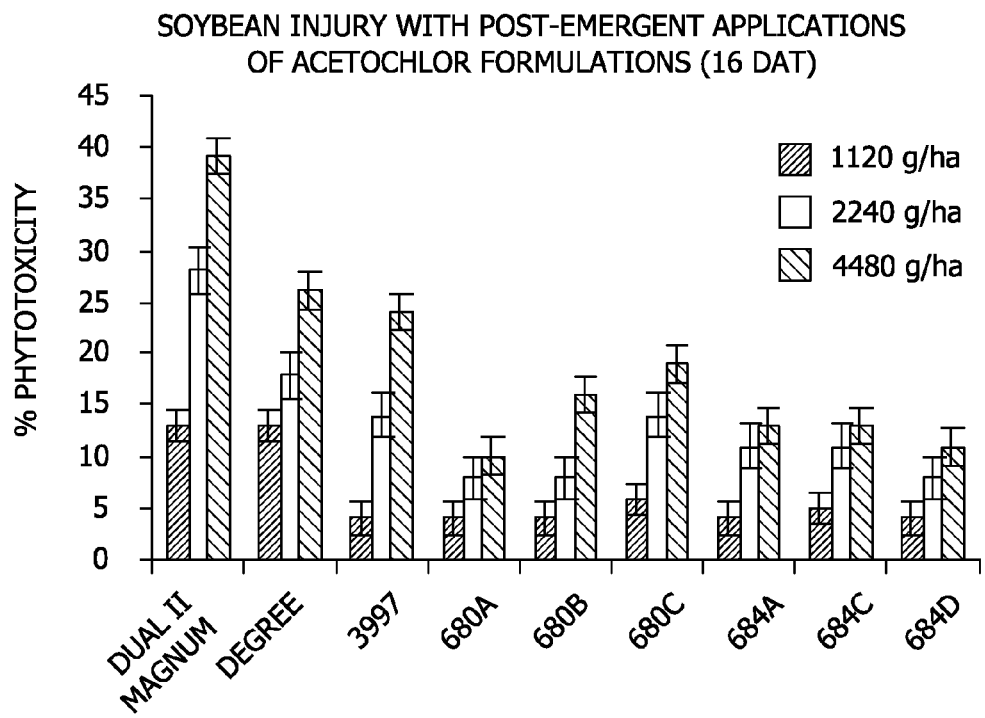
FIG. 83 is a graph depicting soybean injury that occurred with post-emergent applications of various microencapsulated acetochlor formulations as described in Example 52.
Figure 84:
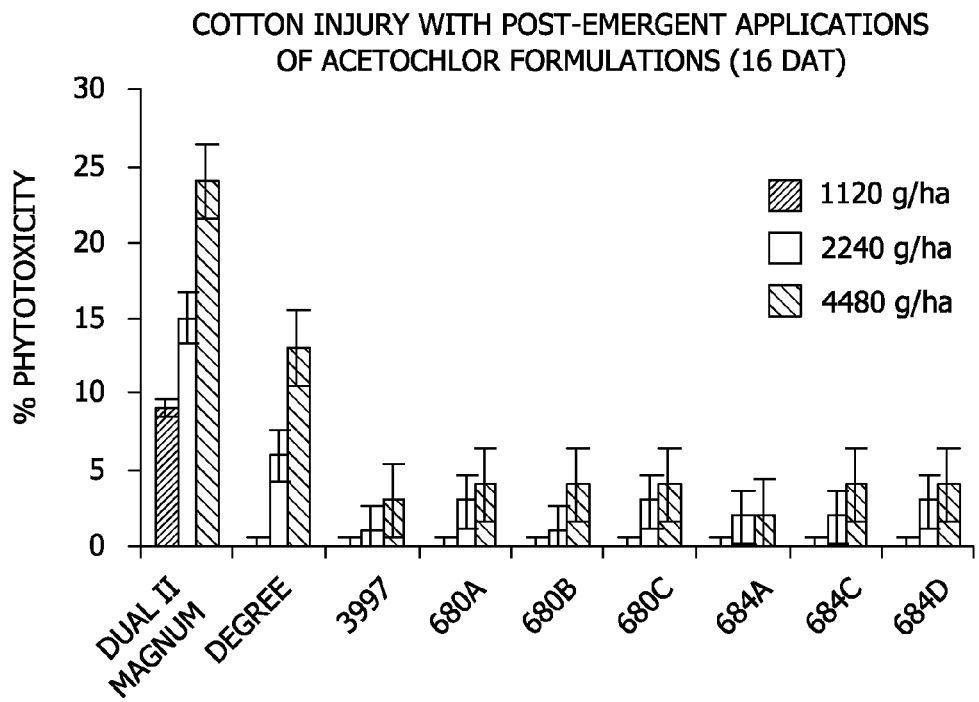
FIG. 84 is a graph depicting cotton injury that occurred with post-emergent applications of various microencapsulated acetochlor formulations as described in Example 52.
Figure 85:
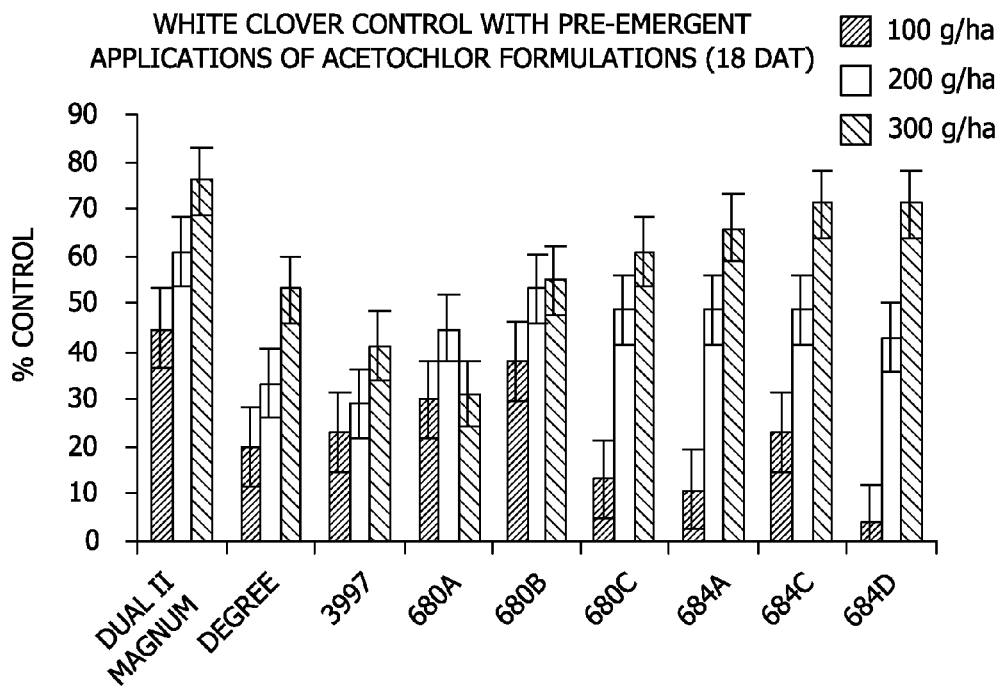
FIG. 85 is a graph depicting control of white clover achieved with pre-emergent applications of various microencapsulated acetochlor formulations as described in Example 52.
Figure 86:
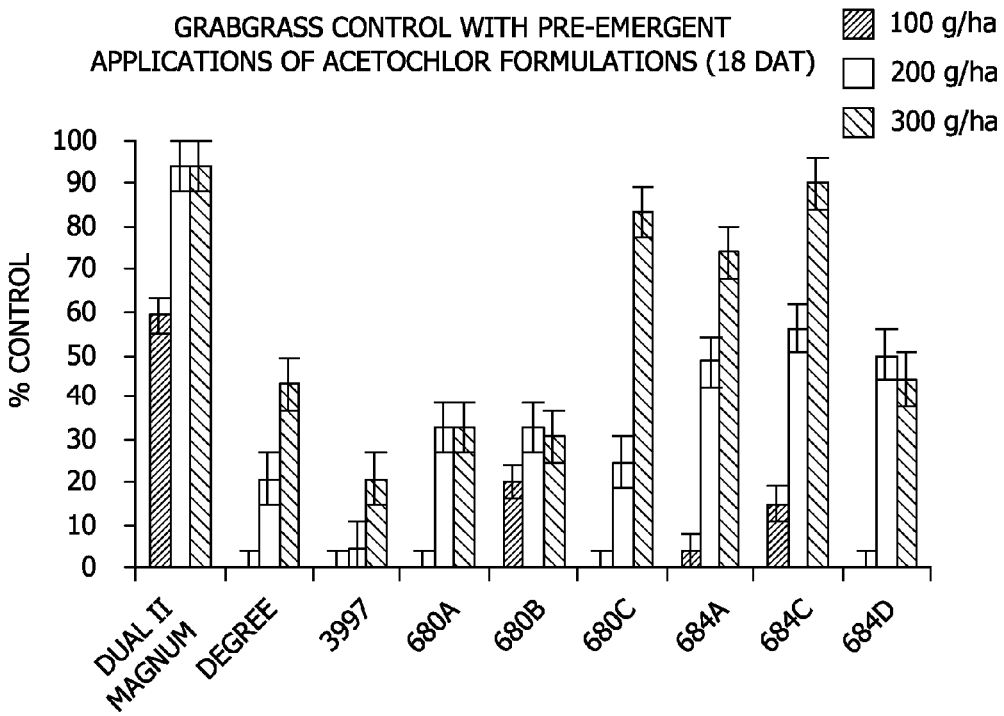
FIG. 86 is a graph depicting control of crabgrass achieved with pre-emergent applications of various microencapsulated acetochlor formulations as described in Example 52.
Figure 87:
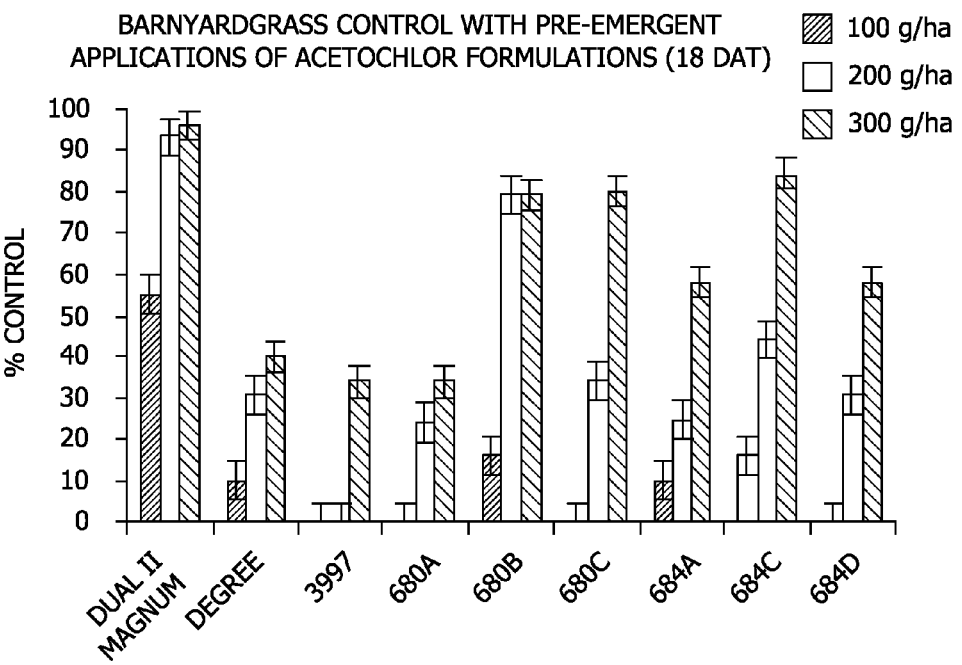
FIG. 87 is a graph depicting control of barnyard grass achieved with pre-emergent applications of various microencapsulated acetochlor formulations as described in Example 52.
Figure 88:
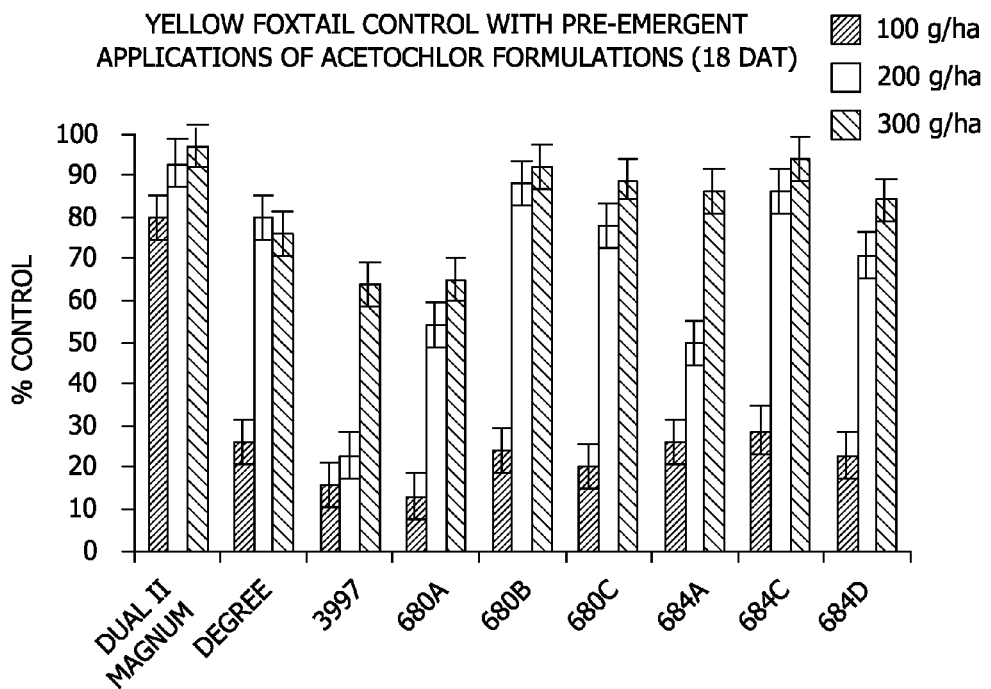
FIG. 88 is a graph depicting control of yellow foxtail achieved with pre-emergent applications of various microencapsulated acetochlor formulations as described in Example 52.

Study of Soybean and Cotton Crop Safety and Post-emergence Weed Control Efficacy Using Microencapsulated Acetochlor Formulations of the Invention Formulations 680A, 680B, 680C, 684A, 684C, and 684D (prepared according to the methods described in Examples 50 and 51) were applied to glyphosate-tolerant (ROUNDUP READY) soybeans and glyphosate-tolerant (ROUNDUP READY) cotton (RR Flex—short to mid-season variety) crops under greenhouse conditions. These formulations were tested against commercial formulations DEGREE and DUAL II MAGNUM and against formulation 3997. The formulations were applied to post-emergent cotton plants and measured for phytotoxicity 16 DAT. The results are shown in FIG. 83 (soybean injury) and FIG. 84 (cotton injury).

All experimental formulations provided better soybean safety than DUAL II MAGNUM at all application rates. See FIG. 83. Comparisons to DEGREE showed the same relationship except for formulation 680C, which showed similar injury at the middle application rate. A surprisingly high level of injury was observed with formulation 3997. All experimental formulations and formulation 3997 also showed significantly less cotton injury than DUAL II MAGNUM at all rates. See FIG. 84. Comparisons to DEGREE showed all formulations to be less injurious at the highest application rate. Release rates were measured in a SOTAX AT-7 dissolution test apparatus according to the method described herein. See the following table for the release rates of the tested formulations.

| Formulation | Release at 6 hours (ppm) | Release at 24 hours (ppm) |
|---|---|---|
| 680A | 67 | 79 |
| 680B | 82 | 106 |
| 680C | 78 | 103 |
| 684A | 69 | 92 |
| 684C | 62 | 78 |
| 684D | 80 | 104 |

Formulations 680A, 680B, 680C, 684A, 684C, and 684D were also tested for weed control efficacy and compared to the weed control efficacy of DEGREE, DUAL II MAGNUM, and formulation 3997. The weed species tested were White Clover (*Trifolium repens*), Crabgrass (*Digitaria sanguinalis*), Barnyardgrass (*Echinochloa crus-galli*) and Yellow foxtail (*Setaria lutescens*). The weed control efficacy data are presented in FIGS. 85 through 88.

Formulations 684A, 684C, and 680C all showed efficacy versus white clover that was equivalent to DUAL1 II MAGNUM at the two highest application rates. See FIG. 85. Formulation 680B was nearly equivalent to the standard at all application rates. The weakest efficacy was seen with formulation 680A and low levels of control were also seen with DEGREE and formulation 3997. Crabgrass control showed formulations 680C and 684C to be equivalent to DUAL II MAGNUM at the highest application rate. See FIG. 86. Very low levels of control were seen with DEGREE, 3997, 680A, and 680B. Barnyardgrass control showed all encapsulated formulations to be less effective than DUAL II MAGNUM at all application rates. See FIG. 87. The best level of control among experimental formulations was seen with 680B, 680C, and 684C. Formulations 680B and 684C provided yellow foxtail control that was equivalent to DUAL II MAGNUM at the two highest application rates. See FIG. 88. Formulations 680B, 680C, 684C, and 684D all showed efficacy that was equal to or better than DEGREE. Poor control was seen with 3997 and 680A. The uneven efficacy with encapsulated formulations and substantially better control observed with DUAL II MAGNUM suggests that this efficacy may have received overhead irrigation immediately after application rather than three days later as specified in the protocol. Delayed overhead irrigation is necessary to achieve results in the greenhouse with encapsulated formulations that more accurately reflect results in the field. Immediate irrigation greatly magnifies differences between emulsified formulations such as DUAL II MAGNUM and encapsulated formulations that are not reflective of actual field results. One might also expect the "680" series of formulations to be more efficacious than the "684" series, because higher levels of Norpar in the "684" series should inhibit release of acetochlor to a greater extent.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying figures shall be interpreted as illustrative and not in a limiting sense.

What is claimed is:

1. A particulate microencapsulated acetamide herbicide comprising:
   a water-immiscible core material comprising the acetamide herbicide, wherein the acetamide herbicide comprises acetochlor and
   microcapsules having a shell wall comprising a polyurea, the microcapsules containing the core material,
   wherein the shell wall is formed in a polymerization medium by a polymerization reaction between a polyisocyanate component comprising a polyisocyanate or mixture of polyisocyanates and a polyamine component comprising a polyamine or mixture of polyamines to form the polyurea,
   wherein the ratio of amine molar equivalents contained in the polyamine component to isocyanate molar equivalents contained in the polyisocyanate component is from 1.15:1 to about 1.4:1, and
   wherein the microcapsules have a mean particle size range from about 7 μm to about 15 μm.

2. The microencapsulated acetamide herbicide of claim 1 wherein the microcapsules have a mean particle size range of from about 8 μm to about 12 μm.

3. The microencapsulated acetamide herbicide of claim 1 wherein the molar equivalents ratio is from 1.15:1 to about 1.3:1.

4. The microencapsulated acetamide herbicide of claim 1 wherein the shell wall is of limited permeability, and the nature and composition of said shell wall and encapsulated acetamide is such that, when an aqueous slurry consisting of 1% by weight of the encapsulated acetamide herbicide in an aqueous medium consisting of deionized water is subjected to agitation at a rate sufficient to maintain the particles in suspension without mechanical rupturing, the acetamide content of the aqueous medium remains less than 100 ppm after agitation for 6 hours at 25° C., and less than 150 ppm acetamide after agitation for 24 hours at 25° C.

5. The microencapsulated acetamide herbicide of claim 1 wherein the weight to weight ratio of acetamide herbicide to the shell wall is from about 6:1 to about 10:1.

6. The microencapsulated acetamide herbicide of claim 1 wherein the polyisocyanate component has a minimum average of 2.5 reactive groups per polyisocyanate molecule and the polyamine component has an average of at least three reactive groups per polyamine molecule.

7. The microencapsulated acetamide herbicide of claim 1 wherein the polyisocyanate component is a blend of a triisocyanate and a diisocyanate wherein the ratio of the triisocyanate to the diisocyanate, on an isocyanate equivalent basis, is between about 90:10 and about 30:70.

8. The microencapsulated acetamide herbicide of claim 1 wherein the core material further comprises from about 1% to about 10% by weight of a water-insoluble organic solvent.

9. The microencapsulated acetamide herbicide of claim 8 wherein the water-insoluble solvent is a paraffinic hydrocarbon.

10. The microencapsulated acetamide herbicide of claim 1 wherein the core further comprises a water-insoluble solvent at a weight ratio of the acetamide herbicide to the solvent of from 15 to 1 to 20 to 1.

11. The microencapsulated acetamide herbicide of claim 1 wherein the polyamine is of the structure $NH_2(CH_2CH_2NH)_mCH_2CH_2NH_2$ where m is from 1 to 5.

12. The microencapsulated acetamide herbicide of claim 1 where more than 50% by weight of the polyisocyanate component is a trimer of 1,6-hexamethylene diisocyanate.

13. The microencapsulated acetamide herbicide of claim 1 wherein the polyisocyanate component comprises an aliphatic polyisocyanate or mixture of aliphatic polyisocyanates.

14. The microencapsulated acetamide herbicide of claim 13 wherein the molar equivalents ratio is from 1.15:1 to about 1.3:1.

15. The microencapsulated acetamide herbicide of claim 1 wherein the polyisocyanate component comprises an aliphatic polyisocyanate or mixture of aliphatic polyisocyanates and wherein the microcapsules have a mean particle size from 9 μm to about 12 μm.

16. The microencapsulated acetamide herbicide of claim 15 wherein the molar equivalents ratio is from about 1.2:1 to about 1.4:1.

17. The microencapsulated acetamide herbicide of claim 1 wherein the molar equivalents ratio is from about 1.2:1 to about 1.3:1.

18. The microencapsulated acetamide herbicide of claim 1 wherein the molar equivalents ratio is from about 1.2:1 to about 1.4:1.

19. The microencapsulated acetamide herbicide of claim 18 wherein:
the polyisocyanate component comprises an aliphatic polyisocyanate or mixture of aliphatic polyisocyanates;
the polyamine component comprises a polyamine of the structure $NH_2(CH_2CH_2NH)_mCH_2CH_2NH_2$ where m is from 1 to 5;
the weight ratio of acetamide herbicide to the shell wall is from 6:1 to 13:1; and
the microcapsules have a mean particle size from 9 μm to about 12 μm.

20. The microencapsulated acetamide herbicide of claim 19 wherein more than 50% by weight of the polyisocyanate component is a trimer of 1,6-hexamethylene diisocyanate.

21. The microencapsulated acetamide herbicide of claim 20 wherein the core material further comprises from about 1% to about 10% by weight of a water-insoluble paraffinic hydrocarbon solvent.

22. The microencapsulated acetamide herbicide of claim 1 wherein the weight to weight ratio of acetamide herbicide to the shell wall is from about 13:1 to about 6:1.

23. The microencapsulated acetamide herbicide of claim 1 wherein the weight to weight ratio of acetamide herbicide to the shell wall is from about 13:1 to about 8:1.

24. An aqueous mixture comprising the microencapsulated acetamide herbicide of claim 1, the aqueous mixture in the form of a concentrate or diluted spray application mixture.

25. The aqueous mixture of claim 24 further comprising one or more co-herbicides selected from acetyl CoA carboxylase inhibitors, organophosphorus herbicides, auxins, photosystem II inhibitors, ALS inhibitors, protoporphyrinogen oxidase inhibitors and carotenoid biosynthesis inhibitors, salts and esters thereof, and mixtures thereof.

26. The aqueous mixture of claim 25 wherein the co-herbicide is the photosystem II inhibitor atrazine.

27. The aqueous mixture of claim 24 wherein the concentration of the acetamide herbicide microcapsules is at least about 30 weight percent but less than about 62.5 weight percent.

28. The aqueous mixture of claim 27 wherein the concentration of acetochlor is at least about 25 weight percent.

29. The aqueous mixture of claim 28 wherein the concentration of acetochlor is less than about 55 weight percent.

30. A method of controlling weeds in a field of crop plants, the method comprising:
forming an application mixture comprising the particulate microencapsulated acetamide herbicide as set forth in claim 1 and
applying the application mixture in a herbicidally effective amount post-emergent to the crop plants.

31. The method of claim 30 wherein the application mixture is applied pre-emergent to the weeds.

32. The method of claim 30 wherein the crop plant is selected from the group consisting of corn, peanuts, potatoes, soybeans, canola, sugarbeets and cotton.

33. The method of claim 30 wherein the crop plants have one or more herbicide tolerant traits.

34. The method of claim 30 wherein the application mixture further comprises glyphosate co-herbicide and the crop plants are transgenic glyphosate-tolerant crop plants, the application mixture further comprises dicamba co-herbicide and the crop plants are transgenic dicamba-tolerant crop plants or the application mixture further comprises glufosinate co-herbicide and the crop plants are transgenic glufosinate-tolerant crop plants.

35. The method of claim 34 wherein the application mixture further comprises glyphosate co-herbicide and the crop plants comprise transgenic glyphosate-tolerant cotton plants having increased glyphosate tolerance in vegetative and reproductive tissues such that application of the herbicidal glyphosate application mixture to said crop and weeds in said field when at least five leaf nodes are present on a cotton plant of said crop does not incur significant glyphosate-mediated reproductive injury to said plant of said crop.

36. The method of claim 35 wherein the genome of the transgenic glyphosate-tolerant cotton plants comprises one or more DNA molecules selected from the group consisting of SEQ ID NO:1, SEQ ID NO:2, SEQ ID NO:3, and SEQ ID NO:4; or
the genome of the transgenic glyphosate-tolerant cotton plants in a DNA amplification method produces an amplicon comprising SEQ ID NO:1 or SEQ ID NO:2; or
the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2.

37. The method of claim 35 wherein the crop of transgenic glyphosate-tolerant cotton plants comprises cotton plants grown from seed of cotton event designated MON 88913 and having representative seed deposited with American Type Culture Collection (ATCC) with Accession No. PTA-4854 or glyphosate-tolerant progeny thereof.

38. The method of claim 35 wherein the crop plants comprise transgenic glyphosate-tolerant cotton plants grown from seed of cotton event designated 1445 or glyphosate-tolerant progeny thereof.

39. The method of claim 30 wherein a rate of crop injury of no more than 20% is maintained for the time period of from 1 day to 28 days after applying the application mixture to crop plants in the growth stage range of from crop emergence to the six-leaf growth stage; and a rate of weed control of at least 60% is achieved for the time period of from application of the application mixture to 12 weeks after application of the application mixture.

40. The method of claim 39 wherein the rate of weed control is at least 70% and the rate of crop injury is no more than 5%.

41. The method of claim 30 wherein the weeds comprise one or more glyphosate resistant species, 2,4-D resistant species, dicamba resistant species and/or ALS inhibitor herbicide resistant species.

42. The method of claim 41 wherein the weeds comprise one or more glyphosate resistant species.

43. The method of claim 42 where the glyphosate-resistant weed species is selected from the group consisting of *Amaranthus palmeri, Amaranthus rudis, Ambrosia artemisiifolia, Ambrosia trifida, Conyza bonariensis, Conyza canadensis, Digitaria insularis, Echinochloa colona, Eleusine indica, Euphorbia heterophylla, Lolium multiflorum, Lolium rigidum, Plantago lanceolata, Sorghum halepense*, and *Urochloa panicoides*.

44. The method of claim 30 wherein the application mixture further comprises one or more co-herbicides selected from acetyl CoA carboxylase inhibitors, organophosphorus herbicides, auxins, photosystem II inhibitors, ALS inhibitors, protoporphyrinogen oxidase inhibitors and carotenoid biosynthesis inhibitors, salts and esters thereof, and mixtures thereof.

45. The method of claim 44 wherein the co-herbicide is the photosystem II inhibitor atrazine.

\* \* \* \* \*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 1
attcaatgta gtcaaacact                                                     20

<210> SEQ ID NO 2
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 2
ttgaatatat attacaaagc                                                     20

<210> SEQ ID NO 3
<211> LENGTH: 2880
<212> TYPE: DNA
<213> ORGANISM: Artificial sequence
<220> FEATURE:
<223> OTHER INFORMATION: Chimeric DNA of cotton genomic DNA and
      transgene insert DNA

<400> SEQUENCE: 3
gcttggtacc gagctcggat ccactagtaa cggccgccag tgtgctggaa ttcgcccttt         60
tttactacga tgttaagtcc tattttacac agtttcttta agacagattt gaccgctcct       120
acgatacttg gagaaacgtt ggtcgaatgt ctcttagaat acaacaacac gatgatcaaa       180
gcagtagcac ctctgtagtg attaacgaac aagcgttgtc ttttctatc accaaaacat        240 tggaaaacat ggagaggaaa agagtagaat tttggaaaga aaataatctt ggtatgagag       300
agtgagattg agcaaaaaat tttgaagagg tcttagcctt ttatatgcgt tcaaagtgga       360
ggaattttgg aaatatccat gtataatgag acaaaatctg catttaaaat ggcatttcgc       420
gtcgcctgcg tcgtgcgagt gcgccccaac cctgacgggt ttggacttac accctcatac       480
acgcgaggca ggattccaag tttagtcatt caatcactct taaagtgagc ttcaagctta       540
gacattacaa attaaattaa ataatataag ataattgcgc taaataaaca aacattttt        600 ttgtgatcct gaacgtaatc aacgagggta tgatggttat gattcacgga aagagcgaga       660
gaagagaacc gtcgctcgaa gaggatgatg attcatccta ttcatgcacg actgtccaac       720
tccccaccca atcaaattcc aaattatgac atgagaagaa catcatccca cgtggtctgt       780
gcttcacgcc accatgtccc acgtgggctc cattttggtg gggcccttcc ccaccgccca       840
agctgatccc gggttggcca tccctacttt taattatcag agccacctcc ccaatctgca       900
aaacgacgga aatggaaaac tataattttc ttttttttca acgtacttat aaaatatttt       960
tcaaaaaagt atgaataaaa ttgtgatatt gcttggccta agaggccaat cttttgcaaa      1020
```

```
tctcgaagtc gggaggcaca ataaaaactt ggaaagtttt ttcaagtgtc tgctttataa    1080
aattattgaa atgcatgtat tcgtacttgc cttatttatc gacaatttaa acattattat    1140
ttcatgaaaa tgtccttcca ccgatttcaa tgacaaaacc ataattact acttttttatt    1200 ttcaattatg tcacggttca catgtttatt agggtttagg ttgaggttaa aactttcgac    1260
tctctattcg taacgcttaa agatgtaggg tttaggttga ggttaaaaca atcatgtaat    1320
gtaaggatac ctgaaaagct gtcattagtg taagtgttta ttactagggt tgtttaaatt    1380
catgttgatg tcaagcttgg ataacccatt ttactaaaaa aataaatgaa gtcccaaagg    1440
gcattgggca tcctatcaaa gatgggaaat ttttcaaaa ttttaaccta aaaagaggt     1500 ggaaagtctt agtccaaata atcagccaca tcagaatttg attcgtttct ttcaagcaaa    1560
ttatacctat tggctgcaat atctttaagt ggaatggtcg gccaaacttt tccatatcag    1620
cttgattcat ctctaaactt gattattctt ttttattaat attaaattcc acaacttgaa    1680
ctttaatttt tttaattaat taaaaaaatt gtcaccttt caagctgaaa agaaaaaga     1740 aaccttaatt attatcacta gtattaaatt tcaaacttg atttgtccta aatttgaaaa    1800
ggggtctcct tcaattcata tatgtagtca tgaagattat aacttagctg aaaatggcct   1860
ccattatttg gcttattcaa tcaaaagttt acaaaactag tgcaaattta atatgataat    1920
gtctacaaga accaaatacg aattgagtaa atttttttgg ctaaaataaa ttacgaattg    1980
atgaattatc attttaaaaa gttctttttta accatttctt ttactgaatt aaaaaaaggt  2040
tttattaatc atatatatta caaattaccc attaagtagc caaattacaa attttaattc    2100
aatgtagtca aacactgata gtttaaacat gactctctta aggtagccaa agcccgggct    2160
taattaaggc gcgccggcca gtcggccgc ggccgcgtta tcaagcttct gcaggtcctg    2220
ctcgagtgga agctaattct cagtccaaag cctcaacaag gtcagggtac agagtctcca    2280
aaccattagc caaagctac aggagatcaa tgaagaatct tcaatcaaag taaactactg    2340
ttccagcaca tgcatcatgg tcagtaagtt tcagaaaaag acatccaccg aagacttaaa    2400
gttagtgggc atctttgaaa gtaatcttgt caacatcgag cagctggctt gtggggacca    2460
gacaaaaaag gaatggtgca gaattgttag gcgcacctac caaaagcatc tttgcccttta   2520 ttgcaaagat aaagcagatt cctctagtac aagtggggaa caaaataacg tggaaaagag    2580
ctgtcctgac agcccactca ctaatgcgta tgacgaacgc agtgacgacc acaaaagaat    2640
tagcttgagc tcaggattta gcagcattcc agattgggtt caatcaacaa ggtacgagcc    2700
atatcacttt attcaaattg gtatcgccaa aaccaagaag gaactcccat cctcaaaggt    2760
ttgtaaggaa gaattcgata tcaagcttga tatcggaagt ttctctcttg agggaggttg    2820
ctcgtggaat gggacacata tggttgttat aataaaccat ttccattgtc atgagatttt    2880
```

<210> SEQ ID NO 4
<211> LENGTH: 1675
<212> TYPE: DNA
<213> ORGANISM: Artificial sequence
<220> FEATURE:
<223> OTHER INFORMATION: Chimeric DNA of cotton genomic DNA and
      transgene insert DNA

<400> SEQUENCE: 4

```
tgaccgaagt taatatgagg agtaaaacac ttgtagttgt accattatgc ttattcacta      60
ggcaacaaat atattttcag acctagaaaa gctgcaaatg ttactgaata caagtatgtc    120
ctcttgtgtt ttagacattt atgaactttc ctttatgtaa ttttccagaa tccttgtcag    180
```

-continued

```
attctaatca ttgctttata attatagtta tactcatgga tttgtagttg agtatgaaaa      240
tattttttaa tgcattttat gacttgccaa ttgattgaca acatgcatca atcgacctgc      300
agccactcga gtggaggcct catctaagcc cccatttgga cgtgaatgta gacacgtcga      360
aataaagatt tccgaattag aataaatttgt ttattgcttt cgcctataaa tacgacggat      420
cgtaatttgt cgttttatca aaatgtactt tcattttata ataacgctgc ggacatctac      480
attttttgaat tgaaaaaaaa ttggtaatta ctctttcttt ttctccatat tgaccatcat      540
actcattgct gatccatgta gatttcccgg acatgaagcc atttacaatt gaatatatat      600
tacaaagcta tttgcttata acatatgcga aaaattttgt actataatca ggggtaaatt      660
taggaggggg cttgtaggtc tcgcttctct taaaatgaaa aattttctat ttagttattt      720
aaaattttaa aagtaaaata taaaaatttc atttaatcct ttaaaaatta taagatata      780
gactattaaa atgatgaaat tacaattta ttatcataaa aattataatt taatttcgac      840
ccctaacaaa attttctgat tttgcccta actgtaatat ttgtataaaa acattttctt      900
tttgcattta atgatttctt taattcagtc caagaaagaa atttattaat tgcatatgcg      960
aaagttagtc cttgcctagt gatattaaag gaaagaaaca taaatcaat aaattaattt     1020
ttaaagcaaa tagtaaaaat aaggaaaaac tttctacgat agtctataat tcaaaaaaag     1080
aaataataat ctttaaccat tgaattttaa aataacatca gaataatcta tttatttaat     1140
ttaataaata ataataacat atatattaat attaaaattt ttattgagct tagtgtcaca     1200
aatcaataaa aaatttctta caaaataaat tatattattt tgagggtgtt ttattatttt     1260
atatattta tacagacata tagaaatata aatacacata ataaaatttg aatccaaatt     1320
tttaattttt aacatttata atttactatt caaccaaaat tttatttatt atttatatca     1380
aatttttata aatatattta tcagataatg cgattttttt tacctatata tagatgacat     1440
aatctacttt aaattaagtc ctaaaaataa tatatcatac caaaaaaatt cttaaaatga     1500
atctgataat acttaaccccc ttttataaaa caatcttaac cccttatata ttttaatatt     1560
aatatcatta taaatataaa tctattgagc atatgtttta aaccaagtaa tgttgagtgc     1620
ggtagtaaaa ctcattacac attttaagta gaacgtagtt cgaaccttgg agaag          1675
```